(12) United States Patent
Sudo et al.

(10) Patent No.: US 11,535,654 B2
(45) Date of Patent: Dec. 27, 2022

(54) FUSION PROTEIN OR CONJUGATED PROTEIN, INTRACELLULAR DELIVERY CARRIER, PARTIAL PEPTIDE, CELL MEMBRANE PERMEATION ENHANCER, DNA, AND VECTOR

(71) Applicant: Keio University, Tokyo (JP)

(72) Inventors: Kei Sudo, Yokohama (JP); Keisuke Niikura, Yokohama (JP); Nobuhide Doi, Yokohama (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 15/735,108

(22) PCT Filed: Jun. 2, 2016

(86) PCT No.: PCT/JP2016/066455
§ 371 (c)(1),
(2) Date: Dec. 8, 2017

(87) PCT Pub. No.: WO2016/199674
PCT Pub. Date: Dec. 15, 2016

(65) Prior Publication Data
US 2018/0237482 A1 Aug. 23, 2018

(30) Foreign Application Priority Data
Jun. 11, 2015 (JP) .............................. JP2015-118432

(51) Int. Cl.
| | |
|---|---|
| *A61K 38/16* | (2006.01) |
| *A61K 38/10* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 39/00* | (2006.01) |
| *A61K 39/385* | (2006.01) |
| *C07K 14/47* | (2006.01) |
| *C12N 15/09* | (2006.01) |
| *A61K 39/395* | (2006.01) |
| *A61K 47/42* | (2017.01) |
| *C07K 19/00* | (2006.01) |
| *A61K 47/50* | (2017.01) |
| *C07K 7/08* | (2006.01) |
| *C07K 14/005* | (2006.01) |
| *C07K 14/705* | (2006.01) |
| *C12N 7/00* | (2006.01) |
| *C07K 7/06* | (2006.01) |

(52) U.S. Cl.
CPC .............. *C07K 14/47* (2013.01); *A61K 38/16* (2013.01); *A61K 39/395* (2013.01); *A61K 47/42* (2013.01); *A61K 47/50* (2017.08); *C07K 7/08* (2013.01); *C07K 14/005* (2013.01); *C07K 14/70596* (2013.01); *C07K 19/00* (2013.01); *C12N 7/00* (2013.01); *C12N 15/09* (2013.01); *C07K 7/06* (2013.01); *C07K 16/00* (2013.01); *C07K 2319/02* (2013.01); *C07K 2319/03* (2013.01); *C07K 2319/21* (2013.01); *C07K 2319/43* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 2002/0102530 A1 | 8/2002 | Keith et al. | |
| 2007/0249808 A1* | 10/2007 | Conrad | ................ C07K 14/005 530/324 |
| 2008/0008683 A1* | 1/2008 | Renard | ................... A61P 31/12 514/21.7 |
| 2009/0325188 A1 | 12/2009 | Glass | |

FOREIGN PATENT DOCUMENTS

| | | |
|---|---|---|
| EP | 2038652 B1 | 9/2013 |
| JP | H10-033186 A | 2/1998 |
| JP | 2009-539410 A | 11/2009 |
| WO | WO 94/04686 A1 | 3/1994 |

(Continued)

OTHER PUBLICATIONS

Inoue et al., Nature, vol. 434, pp. 234-238 (2005) (Year: 2005).*

(Continued)

*Primary Examiner* — Thea D' Ambrosio
(74) *Attorney, Agent, or Firm* — Wolf, Greenfield & Sacks, P.C.

(57) ABSTRACT

The present invention addresses the problem of providing: a fusion protein or conjugated protein having excellent cell membrane permeability, containing a partial peptide derived from human, and suitable for intracellular delivery; an intracellular delivery carrier comprising such a fusion protein or conjugated protein; a partial peptide; a cell membrane permeation enhancer comprising the partial peptide; DNA; and a vector. The fusion protein or conjugated protein has a partial peptide comprising at least seven consecutive amino acid residues of an amino acid sequence encoded by a predetermined DNA, and a ligand directly or indirectly bound to the partial peptide and having the capability of binding to cell surfaces. The ligand is preferably an antibody. The intracellular delivery carrier comprises the fusion protein or conjugated protein. The cell membrane permeation enhancer comprises the partial peptide.

20 Claims, 12 Drawing Sheets
Specification includes a Sequence Listing.

(56) References Cited

FOREIGN PATENT DOCUMENTS

| WO | WO 02/04678 A2 | 1/2002 |
| WO | WO 2007/146702 A2 | 12/2007 |

OTHER PUBLICATIONS

"Conjugated protein", Merriam-Webster, available online at https://www.merriam-webster.com/dictionary/conjugated%20protein, 10 pages (accessed on Apr. 1, 2019) (Year: 2019).*

"Fusion Protein Nomenclature", American Medical Association, available online at https://www.ama-assn.org/about/united-states-adopted-names/fusion-protein-nomenclature, 6 pages (accessed on Apr. 1, 2019) (Year: 2019).*

UniProt Accession No. Q96TB5, 4 pages (2001) (Year: 2001).*

European Nucleotide Archive, Accession No. AB051004, 2 pages (2000) (Year: 2000).*

Wang et al., Frontiers in Psychiatry 9:1-9 (2018) (Year: 2018).*

UniProt Accession No. Q8MIQ0, 3 pages (2002) (Year: 2002).*

Dinca et al., Int. J. Mol. Sci. 17:13 pages (Feb. 2016) (Year: 2016).*

Munyendo et al., Biomolecules 2:187-202 (2012) (Year: 2012).*

Murriel et al., Expert Opin. Drug Deliv. 3:739-746 (2006) (Year: 2006).*

Hakansson et al., Prot. Sci. 10:2138-2139 (2001) (Year: 2001).*

The Protein Man, "8 Protein Tags Explained," available online at https://info.gbiosciences.com/blog/bid/198500/8-protein-tags-explained, 6 pages (2014) (Year: 2014).*

"Ligand", available online at http://kolibri.teacherinabox.org.au/modules/en-boundless/www.boundless.com/biology/definition/ligand/index.html, 3 pages (accessed on 2021) (Year: 2021).*

"Ligand", BiologyOnline, available online at https://www.biologyonline.com/dictionary/ligand, 2 pages (accessed on 2021) (Year: 2021).*

Zhao et al., Nat. Commun. 10:16 pages (2019) (Year: 2019).*

He et al., Appl. Environ. Microbiol. 71:3753-3760 (2005) (Year: 2005).*

Partial Supplementary European Search Report dated Jan. 7, 2019 in connection with EP Patent Application No. 16807381.5.

International Search Report dated Aug. 30, 2016, in connection with International Application No. PCT/JP2016/066455.

De Coupade et al., Novel human-derived cell-penetrating peptides for specific subcellular delivery of therapeutic biomolecules. Biochem J. Sep. 1, 2005;390(Pt 2):407-18.

Inoue et al., The immunoglobulin superfamily protein Izumo is required for sperm to fuse with eggs. Nature. Mar. 10, 2005;434(7030):234-8.

Salomone et al., A novel chimeric cell-penetrating peptide with membrane-disruptive properties for efficient endosomal escape. J Control Release. Nov. 10, 2012;163(3):293-303. doi: 10.1016/j.jconrel.2012.09.019. Epub Oct. 2, 2012. PubMed PMID: 23041543.

Shrestha et al., Evaluation of recombinant fusion protein comprising dog zona pellucida glycoprotein-3 and Izumo and individual fragments as immunogens for contraception. Vaccine. Jan. 23, 2014;32(5):564-71. doi: 10.1016/j.vaccine.2013.11.078. Epub Dec. 13, 2013.

Sudo et al., Human-derived fusogenic peptides for the intracellular delivery of proteins. J Control Release. Jun. 10, 2017;255:1-11. doi: 10.1016/j.jconrel.2017.03.398. Epub Apr. 4, 2017.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Wang et al., Recent progress of cell-penetrating peptides as new carriers for intracellular cargo delivery. J Control Release. Jan. 28, 2014;174:126-36. doi: 10.1016/j.jconrel.2013.11.020. Epub Dec. 1, 2013. Review.

Gerbaud et al., Review: An overview of molecular events occurring in human trophoblast fusion. Placenta. Apr. 2015;36 Suppl 1:S35-42. doi: 10.1016/j.placenta.2014.12.015. Epub Dec. 24, 2014. PMID: 25564303.

\* cited by examiner

FIG. 2A

| | | | |
|---|---|---|---|
| eGFP | 6xHis | FLAG | TCS | eGFP |
| eGFP-B55 | 6xHis | FLAG | TCS | eGFP | B55 |
| eGFP-IZUMO1$_{57-113}$ | 6xHis | FLAG | TCS | eGFP | IZUMO1$_{57-113}$ |
| eGFP-CD9$_{113-194}$ | 6xHis | FLAG | TCS | eGFP | CD9$_{113-194}$ |
| eGFP-Syncytin1$_{345-422}$ | 6xHis | FLAG | TCS | eGFP | Syncytin1$_{345-422}$ |

FIG. 2B

| | | | | |
|---|---|---|---|---|
| eGFP-Syncytin1(FP) | 6xHis | FLAG | TCS | eGFP | (G$_4$S)$_3$ | FP |
| eGFP-Syncytin1(NHR) | 6xHis | FLAG | TCS | eGFP | NHR |
| eGFP-Syncytin1(CHR) | 6xHis | FLAG | TCS | eGFP | CHR |
| eGFP-Syncytin1(FP-NHR) | 6xHis | FLAG | TCS | eGFP | (G$_4$S)$_3$ | FP | NHR |
| eGFP-Syncytin1(NHR-CHR) | 6xHis | FLAG | TCS | eGFP | NHR | CHR |
| eGFP-Syncytin1(FP-NHR-CHR) | 6xHis | FLAG | TCS | eGFP | (G$_4$S)$_3$ | FP | NHR | CHR |

FIG. 3A

| | | | | |
|---|---|---|---|---|
| 6xHis | FLAG | TCS | eGFP | TAT | eGFP-TAT

| | | | | | |
|---|---|---|---|---|---|
| 6xHis | FLAG | TCS | eGFP | HA2 | TAT | eGFP-HA2-TAT

| | | | | | |
|---|---|---|---|---|---|
| 6xHis | FLAG | TCS | eGFP | IZUMO$_{157-113}$ | TAT | eGFP-IZUMO$_{157-113}$-TAT

| | | | | | |
|---|---|---|---|---|---|
| 6xHis | FLAG | TCS | eGFP | CD9$_{113-194}$ | TAT | eGFP-CD9$_{113-194}$-TAT

FIG. 3B

| | | | | | |
|---|---|---|---|---|---|
| 6xHis | FLAG | TCS | eGFP | (G4S)$_3$ | FP | TAT | eGFP-Syncytin1(FP)-TAT

| | | | | | |
|---|---|---|---|---|---|
| 6xHis | FLAG | TCS | eGFP | NHR | TAT | eGFP-Syncytin1(NHR)-TAT

| | | | | | |
|---|---|---|---|---|---|
| 6xHis | FLAG | TCS | eGFP | CHR | TAT | eGFP-Syncytin1(CHR)-TAT

| | | | | | | |
|---|---|---|---|---|---|---|
| 6xHis | FLAG | TCS | eGFP | (G4S)$_3$ | FP | NHR | TAT | eGFP-Syncytin1(FP-NHR)-TAT

| | | | | | | |
|---|---|---|---|---|---|---|
| 6xHis | FLAG | TCS | eGFP | NHR | CHR | TAT | eGFP-Syncytin1(NHR-CHR)-TAT

| | | | | | | | |
|---|---|---|---|---|---|---|---|
| 6xHis | FLAG | TCS | eGFP | (G4S)$_3$ | FP | NHR | CHR | TAT | eGFP-Syncytin1(FP-NHR-CHR)-TAT

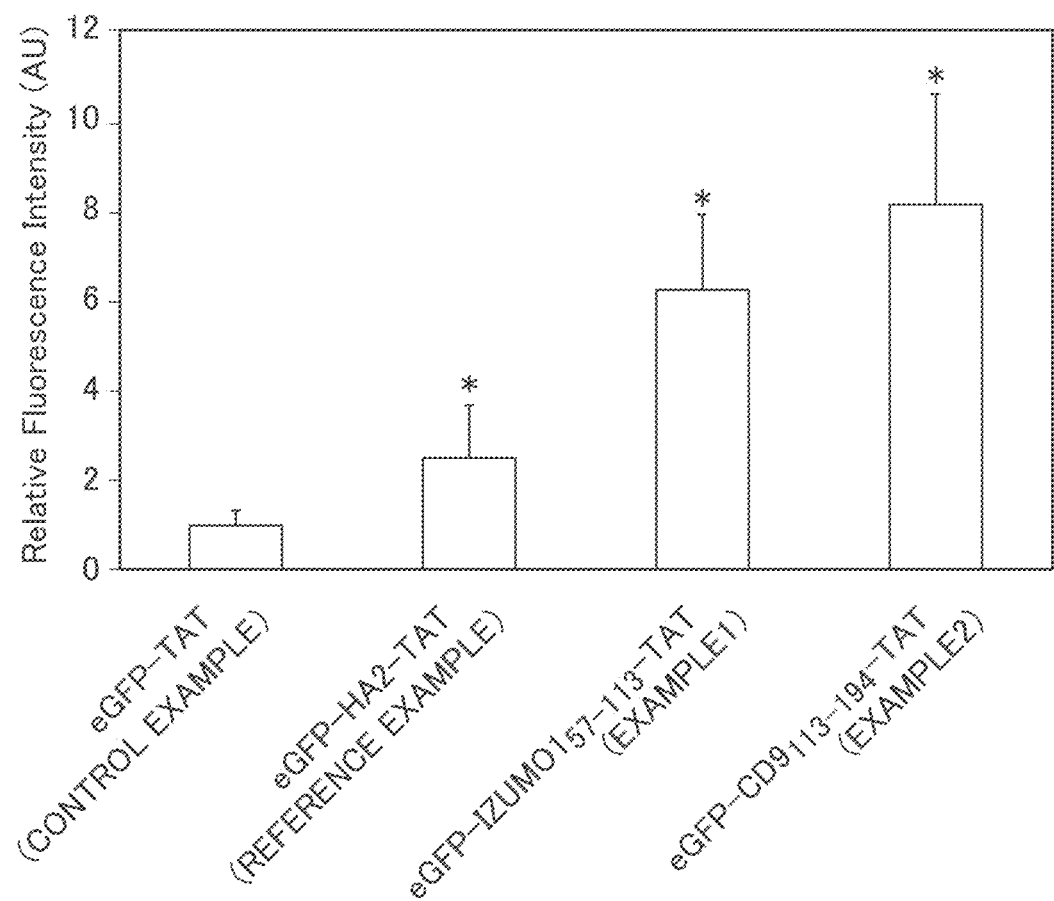

FIG. 9

IZUMO1

```
57---------67---------77--|------87---------97--------107----|
VDEATLQKGSWSLLKDLKRI TDSDVKGDLFVKELFWMLHLQKETFATYVARFQKEAY : OrigSeq (SEQ ID NO: 12)
----HHHHHHHHHHHHHHH--|-HHHHHHHHHHHHHHHHHHHHHHHHHHHHHH-----| : Jnet(SEQ ID NO: 50)
----HHHHHHHHHHHHHHHH-|-HHHHHHHHHHHHHHHHHHHHHHHHHHHHH------| : jhmm(SEQ ID NO: 51)
------HHHHHHHHHHHHHH-|-HHHHHHHHHHHHHHHHHHHHHHHHHHHHH------| : jpssm(SEQ ID NO: 52)
---------------------|--------------------------------------| : Lupas 14
---------------------|--------------------------------------| : Lupas 21
---------------------|--------------------------------------| : Lupas 28
----BB---BBB--BB---B-|-B----BB--BBBBB---BB---B--BB--B-------| : Jnet_25 (SEQ ID NO: 53)
---------B---B---B---|-B-------B---BB------B----B-----------| : Jnet_5 (SEQ ID NO: 54)
-----------------B---|-----------B--------------------------| : Jnet_0 (SEQ ID NO: 55)
```

CD9

```
113--------123--------133---------143----------153----------163----------173---------183---------193 :
HKDEVIKEVQEFYKDTYNKLKTK DEPQRETLKAIHYALNCCGLAGGVEQF ISDICPKKDVLET FTVKSCPDAI KEVFDNKFH : OrigSeq(SEQ ID NO: 2)
----HHHHHHHHHHHHHHHHH----HHHHHHHHHHHH------------------------------------HHHHHHHHHH---- : Jnet (SEQ ID NO: 56)
----HHHHHHHHHHHHHHHHH----HHHHHHHHHHHH-----------E------------------------HHHHHHHHHH--- : jhmm (SEQ ID NO: 57)
--HHHHHHHHHHHHHHHHHHH----HHHHHHHHHHHH------------------------------------HHHHHHHHHH--- : jpssm (SEQ ID NO: 58)
---------------------------------------------------------------------------------------- : Lupas 14
---------------------------------------------------------------------------------------- : Lupas 21
---------------------------------------------------------------------------------------- : Lupas 28
----BB--B--B--BB--B-------B-BBB-BBB--BB-BB-------BB--BBB-----BB---B---B---B-BB----B---- : Jnet_25 (SEQ ID NO: 59)
----B---B---B---B------------B-B-----B-B-----------B------------------B--BB------B----- : Jnet_5 (SEQ ID NO: 60)
---------------B------------B--------B-------------------------------------------------- : Jnet_0 (SEQ ID NO: 61)
```

Syncytin1

```
320---------330--|------340---------350---------360---------370---------:
ILPFVIGAGVLGALGTGIGG ITTSTQFYYK LSQELNGDMERVADSLVTLQ DQLNSLAAVV : OrigSeq
---HHHHHHHHHHHHH-|--HHHHHHHH---HHHHHHHHHHHHHHHHHHHHHHHHHHHH-- : Jnet
----HHHHHHHHHHHH-|--HHHH--HHHHHHHHHHHHHHHHHHHHHHHHHHHHHHH---- : jhmm
-----HHHHHHHHHHH-|--HHHHHHHHHHHHHHHHHHHHHHHHHHHHH----HHHHHHH- : jpssm
-----------------|--------------------cccccccccccc----------- : Lupas 14
-----------------|-------------------cccccccccccccccccccc---- : Lupas 21
-----------------|------------ccccccccccccccccccccccccccccccc : Lupas 28
----B---B-BBBBB-BB--BBB BBB BB-BB--BB-BB--BB-BB-B---B--BB-BB : Jnet_25
----------B------|---B----B---B----B---B--------B----B----B- : Jnet_5
-----------------|-------------------------------------------- : Jnet_0
```

```
380--------390--------400---------410---------420---------430-----------:
LQNRRALDLL TAERGGTCLFLGE ECCYYVNQSGIVTEKVK EIRDRIQRRAEELRNTGPWGL : OrigSeq (SEQ ID NO: 18)
HHHHHH---HH-----EEEEE----EEEEE----HHHHHHHHHHHHHHHHHH--------- : Jnet (SEQ ID NO: 62)
HHHHHH---HHHH------EEEEE----EEEE----HHHHHHHHHHHHHHHH--------- : jhmm (SEQ ID NO: 63)
------EE--------EEEEE----EEEEE----HHHHHHHHHHHHHHHHHH--------- : jpssm (SEQ ID NO: 64)
------------------------------------------------------------- : Lupas 14 (SEQ ID NO: 65)
------------------------------------------------------------- : Lupas 21 (SEQ ID NO: 66)
CCCCCCCCCCCCCC----------------------------------------------- : Lupas 28 (SEQ ID NO: 67)
B-B--BBBBBBBB---BBBBBB-----BBBBB------B---BB--B--BB--B------B- : Jnet_25 (SEQ ID NO: 68)
B-----B-----------BB--B----BBB-B-----------B---B--B---B------- : Jnet_5 (SEQ ID NO: 69)
-------B----------------------B------------B------------------ : Jnet_0 (SEQ ID NO: 70)
```

FIG. 10

| Construct | Structure |
|---|---|
| eGFP-NLS | 6xHis \| FLAG \| TCS \| eGFP \| NLS |
| eGFP-TAT-NLS | 6xHis \| FLAG \| TCS \| eGFP \| TAT \| NLS |
| eGFP-HA2-TAT-NLS | 6xHis \| FLAG \| TCS \| eGFP \| HA2 \| TAT \| NLS |
| eGFP-IZUMO1$_{57-113}$-TAT-NLS | 6xHis \| FLAG \| TCS \| eGFP \| IZUMO1$_{57-113}$ \| TAT \| NLS |
| eGFP-Syncytin1(FP)-TAT-NLS | 6xHis \| FLAG \| TCS \| eGFP \| (G$_4$S)$_3$ \| FP \| TAT \| NLS |
| eGFP-Syncytin1(FP')-TAT-NLS | 6xHis \| FLAG \| TCS \| eGFP \| (G$_4$S)$_3$ \| FP' \| TAT \| NLS |

FUSION PROTEIN OR CONJUGATED PROTEIN, INTRACELLULAR DELIVERY CARRIER, PARTIAL PEPTIDE, CELL MEMBRANE PERMEATION ENHANCER, DNA, AND VECTOR

CROSS REFERENCE TO RELATED APPLICATIONS

This application is a National Stage filing under 35 U.S.C. § 371 of International PCT Application No. PCT/JP2016/066455, filed Jun. 2, 2016, which claims priority to Japanese Patent Application No. 2015-118432, filed Jun. 11, 2015, the entire contents of the aforementioned applications are hereby incorporated herein by reference.

TECHNICAL FIELD

The present invention relates to a fusion protein or conjugated protein, an intracellular delivery carrier, a partial peptide, a cell membrane permeation enhancer, DNA, and a vector.

BACKGROUND ART

In recent years, the drug delivery system (DDS) has been under extensive research and development as a means for performing safe and effective drug administration with reduced risk of overdose and side effects of a drug.

DDS has been used in attempts for delivering various drugs to cells, but some of the drugs, for example, biopolymers such as proteins, have low cell membrane permeability.

In view of the above, there have been demands for efficiently delivering such drugs having low cell membrane permeability into cells. In recent years, as a technology to satisfy the above demands, cell membrane permeable peptides have attracted attention.

For example, the TAT peptide as a transcription factor of HIV is known as a cell membrane permeable peptide (see Patent Document 1).

Patent Document 1: Japanese Unexamined Patent Application, Publication No. H10-33186

DISCLOSURE OF THE INVENTION

Problems to be Solved by the Invention

By the way, in endocytosis, which is one of the mechanisms of cell membrane permeation, a ligand first recognizes a receptor present on a cell surface to bind with the cell surface, and then is internalized into an endosome. After internalization into the endosome, the ligand is then released from the endosome and discharged into the cytoplasm of the cell. Thereby, the ligand is delivered into the cell.

The aforementioned TAT peptide suffers from low cell membrane permeability due to low releasability from endosomes (hereinafter may also be referred to as "endosomal escape ability" as used herein), and thus can not sufficiently release an active ingredient of interest into the inside of a cell.

Meanwhile, membrane fusion peptides HA2 (derived from virus), B18 (derived from sea urchin), and B55 (derived from sea urchin) are known. They are factors related to membrane fusion upon virus infection or fertilization. These peptides, which have superior endosomal escape ability, could be considered as candidate peptides for intracellular delivery with high cell membrane permeability.

However, a concern is that the non-human origin of the HA2, B18, and B55 peptides may generate immunogenicity when these peptides are used as DDS.

Therefore, there have been demands for a human-derived and less immunogenic peptide having excellent cell membrane permeability as a peptide for intracellular delivery.

The present invention is made in view of the above circumstances. An object of the present invention is to provide a fusion protein or conjugated protein suitable for intracellular delivery including a human-derived partial peptide having excellent cell membrane permeability. Further, another object of the present invention is to provide an intracellular delivery carrier including such a fusion protein or conjugated protein, a partial peptide, a cell membrane permeation enhancer including the partial peptide, DNA encoding the partial peptide, and a vector having the DNA incorporated therein.

Means for Solving the Problems

The present inventors found that a partial peptide consisting of a portion of the amino acid residues from human-derived membrane fusion-related proteins IZUMO 1, CD9, or Syncytin 1 has excellent endosomal escape ability. Thus the present invention has been completed. More specifically, the present invention can provide the following.

(1) A fusion protein or conjugated protein including a partial peptide consisting of at least seven consecutive amino acid residues of an amino acid sequence encoded by DNA set forth in any of (a) to (d), and
a ligand directly or indirectly attached to the partial peptide, the ligand having a binding capability to a cell surface:
(a) DNA having a base sequence encoding an amino acid sequence set forth in SEQ ID NO: 1, 2, or 3,
(b) DNA having a base sequence capable of hybridizing under stringent conditions with a base sequence complementary to a base sequence encoding an amino acid sequence set forth in SEQ ID NO: 1, 2, or 3,
(c) DNA having a base sequence encoding an amino acid sequence where one or more amino acids are substituted, deleted, and/or added to an amino acid sequence set forth in SEQ ID NO: 1, 2, or 3, and
(d) DNA consisting of a base sequence encoding an amino acid sequence having 90% or more homology with an amino acid sequence set forth in SEQ ID NO: 1, 2, or 3.

(2) The fusion protein or conjugated protein according to (1), wherein the ligand is an antibody.

(3) The fusion protein according to (1) or (2).

(4) An intracellular delivery carrier including the fusion protein or conjugated protein according to (1) or (2).

(5) A partial peptide consisting of at least seven consecutive amino acid residues of an amino acid sequence encoded by DNA set forth in any of (a) to (d):
(a) DNA having a base sequence encoding an amino acid sequence set forth in SEQ ID NO: 1, 2, or 3,
(b) DNA having a base sequence capable of hybridizing under stringent conditions with a base sequence complementary to a base sequence encoding an amino acid sequence set forth in SEQ ID NO: 1, 2, or 3,
(c) DNA having a base sequence encoding an amino acid sequence where one or more amino acids are substituted, deleted, and/or added to an amino acid sequence set forth in SEQ ID NO: 1, 2, or 3, and (d) DNA consisting of a base sequence encoding an amino acid sequence having 90% or more homology with an amino acid sequence set forth in SEQ ID NO: 1, 2, or 3.

(6) A cell membrane permeation enhancer including the partial peptide according to (5).

(7) DNA encoding the fusion protein according to (1) or (2) or the partial peptide according to (5).

(8) A vector having the DNA according to (7) incorporated therein.

Effects of the Invention

According to an embodiment of the present invention, a fusion protein or conjugated protein suitable for intracellular delivery including a human-derived partial peptide having excellent cell membrane permeability can be provided. Furthermore, according to other embodiments of the present invention, the followings can be provided: an intracellular delivery carrier including such a fusion protein or conjugated protein, a partial peptide, a cell membrane permeation enhancer including the partial peptide, DNA encoding the partial peptide, and a vector having the DNA incorporated therein.

BRIEF DESCRIPTION OF THE DRAWINGS

FIG. 2 schematically shows the DNA constructs of eGFP fusion proteins.

FIG. 3 schematically shows the DNA constructs of eGFP-TAT-containing fusion proteins.

FIG. 4 shows a graph of the fluorescence intensities for an eGFP-TAT fusion protein, an eGFP-HA2-TAT fusion protein, an eGFP-IZUMO $1_{57-113}$-TAT fusion protein, and an eGFP-CD9$_{113-194}$-TAT fusion protein.

FIG. 9 shows the secondary structure predictions of IZUMO $1_{57-113}$, CD9$_{113-194}$, and Syncytin $1_{320-440}$ which contain candidates for a human-derived cell membrane permeable peptide.

FIG. 10 schematically shows the DNA constructs of eGFP-TAT-NLS-containing fusion proteins.

PREFERRED MODE FOR CARRYING OUT THE INVENTION

Figure 1:
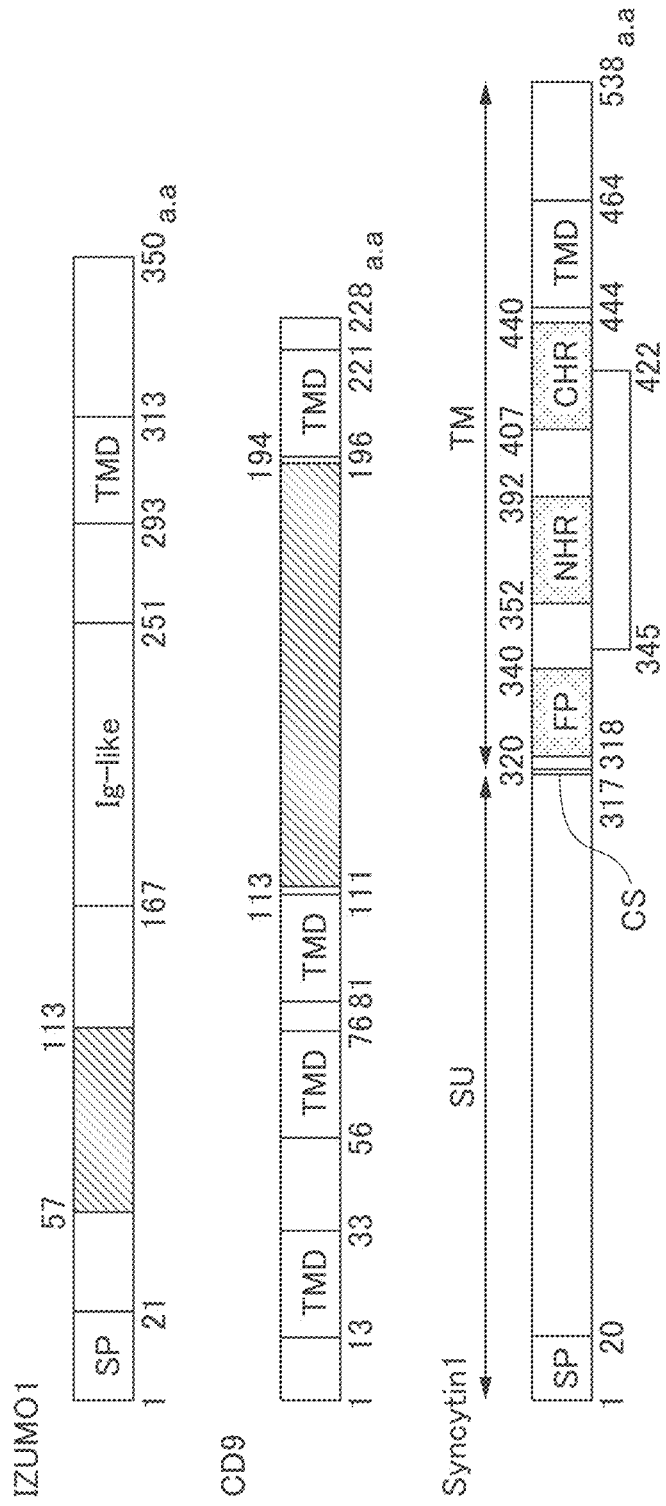
FIG. 1 shows the domain structures of "IZUMO 1," "CD9," and "Syncytin 1."

Below, the specific embodiments of the present invention will be described in detail, but the present invention shall not be limited to the following embodiments in any sense. The present invention can be implemented with modifications appropriately made thereto within the scope of the object of the present invention.

<Fusion Protein or Conjugated Protein>

The fusion protein or conjugated protein according to an embodiment of the present invention includes a partial peptide consisting of at least seven consecutive amino acid residues of an amino acid sequence encoded by DNA set forth in any of the following (a) to (d), and a ligand attached directly or indirectly to the partial peptide, the ligand having a binding capability to a cell surface:

(a) DNA having a base sequence encoding an amino acid sequence set forth in SEQ ID NO: 1, 2, or 3, (b) DNA having a base sequence capable of hybridizing under stringent conditions with a base sequence complementary to a base sequence encoding an amino acid sequence set forth in SEQ ID NO: 1, 2, or 3, (c) DNA having a base sequence encoding an amino acid sequence where one or more amino acids are substituted, deleted, and/or added to an amino acid sequence set forth in SEQ ID NO: 1, 2, or 3, and (d) DNA consisting of a base sequence encoding an amino acid sequence having 90% or more homology with an amino acid sequence set forth in SEQ ID NO: 1, 2, or 3.

The fusion protein or conjugated protein according to an embodiment of the present invention has high endosomal escape ability by virtue of the presence of the partial peptide configured as described above, and thus can show excellent cell membrane permeability. It is noted that the "fusion protein" according to an embodiment of the present invention refers to a protein in which the partial peptide is attached to one or more other types of proteins. Further, the "conjugated protein" according to an embodiment of the present invention refers to a complex in which the partial peptide is attached to a component other than a protein (for example, a low molecular weight compound, nucleic acid, a carbohydrate chain, a nanoparticle, and the like).

(Partial Peptide)

The partial peptide in the fusion protein or conjugated protein according to an embodiment of the present invention consists of at least seven consecutive amino acid residues of an amino acid sequence encoded by DNA set forth in any of the above (a) to (d).

The amino acid sequence set forth in SEQ ID NO: 1 is a portion of a fusion core helix peptide near the N-terminus of a human-derived and membrane fusion-related protein IZUMO 1, the portion corresponding to amino acid residues from position 76 to position 113 numbered from the side of the N-terminus of IZUMO 1.

Within the amino acid sequence set forth in SEQ ID NO: 1, particularly preferred are an amino acid sequence (SEQ ID NO: 4) corresponding to amino acid residues from position 76 to position 94 numbered from the side of the N-terminus of IZUMO 1, an amino acid sequence (SEQ ID NO: 5) corresponding to amino acid residues from position 81 to position 113 numbered from the side of the N-terminus of IZUMO 1, or an amino acid sequence (SEQ ID NO: 6) corresponding to amino acid residues from position 95 to position 113 numbered from the side of the N-terminus of IZUMO 1. This is in particular because the resulting partial peptides will have high endosomal escape ability, and thus show excellent cell membrane permeability.

The amino acid sequence set forth in SEQ ID NO: 2 is a portion of the second extracellular loop peptide near the C-terminus of a human-derived and membrane fusion-related protein CD9, the portion corresponding to amino acid residues from position 113 to position 194 numbered from the side of the N-terminus of CD9.

Within the amino acid sequence set forth in SEQ ID NO: 2, particularly preferred are an amino acid sequence (SEQ ID NO: 7) corresponding to amino acid residues from position 115 to position 133 numbered from the side of the N-terminus of CD9, an amino acid sequence (SEQ ID NO: 8) corresponding to amino acid residues from position 138 to position 151 numbered from the side of the N-terminus of CD9, or an amino acid sequence (SEQ ID NO: 9) corresponding to amino acid residues from position 182 to position 190 numbered from the side of the N-terminus of CD9. This is in particular because the resulting partial peptides will have high endosomal escape ability, and thus show excellent cell membrane permeability.

The amino acid sequence set forth in SEQ ID NO: 3 represents an amino acid sequence of the membrane fusogenic FP peptide of the TM domain at the C-terminus side of a human-derived and membrane fusion-related protein Syncytin 1, and corresponds to amino acid residues from position 320 to position 340 numbered from the side of the N-terminus of Syncytin 1.

Within the amino acid sequence set forth in SEQ ID NO: 3, preferred is an amino acid sequence (SEQ ID NO: 44) corresponding to amino acid residues from position 322 to position 340 numbered from the side of the N-terminus of Syncytin 1, and particularly preferred is an amino acid sequence (SEQ ID NO: 10) corresponding to amino acid residues from position 321 to position 334 numbered from the side of the N-terminus of Syncytin 1. This is in particular because the resulting partial peptides will have high endosomal escape ability, and thus show excellent cell membrane permeability.

There is no particular limitation for the number of amino acid residues of the partial peptide according to an embodiment of the present invention as long as the peptide consists of at least seven consecutive amino acid residues of an amino acid sequence encoded by DNA set forth in any of the above (a) to (d). It can be appropriately selected, for example, according to the number of amino acid residues encoded by SEQ ID NOs: 1 to 3 and other factors. For example, the partial peptide according to an embodiment of the present invention may be composed of at least 10, 12, 15, 18, 20, 30, 40, 50, 60, 70, or so on of consecutive amino acid residues of an amino acid sequence encoded by DNA set forth in any of the above (a) to (d). Further, there is no particular limitation for the upper limit of the number. The partial peptide according to an embodiment of the present invention may be composed of 75 or less, 65 or less, 55 or less, 45 or less, 35 or less, 25 or less, 22 or less, 17 or less, 16 or less, 14 or less, 13 or less, or so on of consecutive amino acid residues of an amino acid sequence encoded by DNA set forth in any of the above (a) to (d).

Variants or homologues of DNA having a base sequence encoding an amino acid sequence set forth in any of SEQ ID NOs: 1 to 10 include DNA having a base sequence capable of hybridizing under stringent conditions with a base sequence complimentary to a base sequence encoding an amino acid sequence set forth in any of SEQ ID NOs: 1 to 10; and DNA consisting of a base sequence having 90% or more (preferably 92% or more, more preferably 95% or more, and even more preferably 99% or more) homology to a base sequence encoding an amino acid sequence set forth in any of SEQ ID NOs: 1 to 10. The "stringent conditions" which allow hybridization with a base sequence complementary to a base sequence set forth in any of SEQ ID NOs: 1 to 10 include, for example, a condition where a reaction is performed in a common hybridization buffer at 40 to 70° C. (preferably 50 to 67° C., more preferably 60 to 65° C.), and then washing is performed in a wash liquid having a salt concentration of 15 to 300 mM (preferably 15 to 150 mM, more preferably 15 to 60 mM, and even more preferably 30 to 50 mM).

Examples of DNA encoding the amino acid sequence of the partial peptide according to an embodiment of the present invention include DNA having a base sequence encoding an amino acid sequence in which one or more amino acids are substituted, deleted, and/or added to an amino acid sequence set forth in any of SEQ ID NOs: 1 to 10. The term "one or more" as used herein usually refers to 3 amino acids or less, and preferably 2 amino acids or less. In order to maintain the cell membrane permeation effect of the partial peptide, a target amino acid residue is desirably mutated to another amino acid so that the properties of the side chain of the target amino acid residue are conserved. In particular, when the number of amino acid residues in the partial peptide is small (for example, when the number of amino acid residues in the partial peptide is 7 to 10) and when the number of mutated amino acids is large (for example, 3 amino acids or less), the cell membrane permeation effect of the partial peptide tends to be maintained after mutation with another amino acid so that the properties of the side chain of a target amino acid are conserved. The properties of an amino-acid side chain include, for example, hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxy group-containing side chain (S, T, Y), amino acids having a sulfur atom-containing side chain (C, M), amino acids having a carboxylic-acid and amide-containing side chain (D, N, E, Q), amino acids having a base-containing side chain (R, K, H), and amino acids having an aromatic-containing side chain (H, F, Y, W) (it is noted that the alphabetical characters in the parentheses are each in accordance with one-letter code of amino acid).

The amino acid sequence of the partial peptide according to an embodiment of the present invention preferably has higher homology with an amino acid sequence set forth in any of SEQ ID NOs: 1 to 10. For example, the amino acid sequence of the partial peptide according to an embodiment of the present invention preferably has 90% or more, more preferably 92% or more, and even more preferably 95% or more (96% or more, 97% or more, 98% or more, 99% or more) homology with an amino acid sequence set forth in any of SEQ ID NOs: 1 to 10. Meanwhile, it is already known that a protein having a modified amino acid sequence in which one or more amino acid residues are deleted, added, and/or substituted with other amino acids in a certain amino acid sequence can maintain its biological activity (Mark, D. F. et al., Proc. Natl. Acad. Sci. USA (1984) 81, 5662-5666; Zoller, M. J. & Smith, M., Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413). Further, an amino acid sequence in which one or more amino acid residues are substituted, deleted, and/or added to an amino acid sequence set forth in any of SEQ ID NOs: 1 to 10 preferably has higher homology with the corresponding amino acid sequence set forth in any of SEQ ID NOs: 1 to 10. For example, the homology between an amino acid sequence in which one or more amino acid residues are substituted, deleted, and/or added to an amino acid sequence set forth in any of SEQ ID NOs: 1 to 10 and the corresponding amino acid sequence set forth in any of SEQ ID NOs: 1 to 10 is preferably 85% or more, more preferably 90% or more, and even more preferably 95% or more (96% or more, 97% or more, 98% or more, 99% or more).

Homology among amino acid sequences or base sequences may be determined using an algorithm BLAST by Karlin and Altschul (Proc. Natl. Acad. Sci. USA 90:5873-5877, 1993). Programs called BLASTN and BLASTX have been developed based on the above algorithm (Altschul et al., J. Mol. Biol. 215:403-410, 1990). When analyzing a base sequence with BLASTN based on BLAST, parameters are set as follows: for example, score=100 and wordlength=12. Further, when analyzing an amino acid sequence with BLASTX based on BLAST, parameters are set as follows: for example, score=50 and wordlength=3. When using BLAST and Gapped BLAST programs, the default parameters are used for each program. Specific approaches for these analysis methods are known (ncbi.nlm.nih.gov.).

The term "DNA" as used in the present invention may be either a sense strand or an antisense strand (for example, it can be used as a probe), and may be in a form of either a single strand or a double strand. Moreover, it may be genomic DNA, cDNA, or synthesized DNA.

In the present invention, there is no particular limitation for a method of obtaining DNA, but examples thereof include known methods such as a method of obtaining cDNA from mRNA by reverse transcription (for example, the RT-PCR method), a method of preparation from genomic DNA, a method of synthesis by chemical synthesis, and a method of isolation from a genomic DNA library or a cDNA library (for example, see Japanese Unexamined Patent Application, Publication No. H11-29599).

The partial peptide according to an embodiment of the present invention may be chemically synthesized, for example, by a known solid-phase peptide synthesis method such as the Fmoc synthesis method. Alternatively, it may also be prepared using a transformant into which an expression vector having DNA encoding the amino acid sequence of the partial peptide has been introduced. That is, the above transformant is first cultured under appropriate conditions to allow a protein (partial peptide) encoded by that DNA to be synthesized.

Any host may be used for obtaining a transformant as long as it is compatible with a vector, and can be transformed with that vector. Examples of the host include known natural cells or artificially established cells of bacteria, yeast, animal cells, insect cells, and the like (see Japanese Unexamined Patent Application, Publication No. H11-29599). An expression vector for obtaining a transformant may be prepared by introducing the aforementioned DNA into a suitable vector. The "suitable vector" may be any one which can be duplicated and maintained or can self-propagate in various prokaryote and/or eukaryote hosts, and can be appropriately selected according to the intended use. The method of introducing a vector can be appropriately selected according to the types of the vector and a host, and the like. There is no particular limitation for the method, but specific examples thereof include known methods such as the protoplast method and the competent method (for example, see Japanese Unexamined Patent Application, Publication No. H11-29599). Further, DNA may be constructed, if desired, so that a tag (6×His, FLAG, and the like) or a thrombin recognition sequence (TCS) for facilitating purification is included in a protein to be synthesized.

In order to obtain a partial peptide easily in a large quantity, a transformant can be cultured in a known nutrient medium appropriately selected according to the type of the transformant at an appropriately adjusted temperature and an appropriately adjusted pH of the nutrient medium for an appropriately adjusted culture duration (for example, see Japanese Unexamined Patent Application, Publication No. H11-29599). Then, a protein synthesized by the transformant in this way may be collected from the transformant or culture solution to obtain the partial peptide according to an embodiment of the present invention. It is noted that there is no particular limitation for the method of isolating and purifying the partial peptide, but examples thereof include known methods such as a method using solubility, a method using difference in molecular weights, and a method using electric charges (for example, see Japanese Unexamined Patent Application, Publication No. H11-29599).

(Ligand)

A ligand in the fusion protein or conjugated protein according to an embodiment of the present invention has a binding capability to a cell surface.

Ligands having a binding capability to a cell surface include molecular recognition elements showing a specific interaction with a specific substance (receptor and the like) on the cell surface, such as a carbohydrate chain, a protein, and an antigen as cell selective markers, and more specifically include antibodies, lectins, cytokines, hormones, neurotransmitters, peptides (TAT, polyarginine, and the like), and carbohydrate chains (chitin, chitosan, hyaluronic acid, and the like). In particular, an antibody is preferably used in view of its high cell selectivity. With regard to an antibody, for example, antibody fragments (for example, an antibody having a molecular weight of 10 to 100 kDa) such as a single-chain antibody fragment (scFv), Fab, a domain antibody, and a diabody may be preferably used.

The ligand is directly or indirectly attached to the aforementioned partial peptide. The mode of attachment can be suitably selected according to the type of the ligand, and other factors. For example, when the ligand is an antibody, a fusion protein of the aforementioned partial peptide and the antibody can be prepared by a genetic engineering approach as in the partial peptide as described above. In that case, the partial peptide may be indirectly attached to the antibody through a linker by arranging the amino acid sequence of the linker between the partial peptide and the antibody, or the partial peptide may be directly attached to the antibody without via a linker. There is no particular limitation for the number of amino acid residues of a linker, but it may be, for example, 1 to 100 amino acid residues, considering the number of amino acid residues of the entire protein and other factors. Examples of the amino acid sequence of a linker include a flexible linker having 3 repeat units of GGGGS (SEQ ID NO: 11) and others. Further, a peptide itself encoded by the amino acid sequence of a linker may be designed so as to have high cell membrane permeability. This can further improve the cell membrane permeability of a fusion protein. In order to design the peptide itself encoded by the amino acid sequence of a linker so as to have high cell membrane permeability, it may be designed to have higher homology with an amino acid sequence set forth in any of SEQ ID NOs: 1 to 10, for example, may be designed to have homology of 70% or more, 80% or more, 90% or more, 95% or more, or so on.

When the ligand is not a protein such as an antibody (for example, when the ligand is a low-molecular weight compound or a carbohydrate chain), the ligand can be directly attached to the partial peptide via chemical bonding by taking advantage of a functional group(s) present at the termini or in the internal portion of the partial peptide (for example, a carboxyl group, an amino group, a sulfhydryl group, and the like). Examples of the mode of chemical bonding in that case include, for example, amide bonding, thioether bonding, ester bonding, and the like. Further, indirect attachment of a ligand with the partial peptide is mainly used when direct attachment is difficult, or indirect attachment is preferred. Indirect attachment may be achieved through a linker. There is no particular limitation for the linker used in this case (that is, a linker when the ligand is not a protein) as long as it has a structure having reactive groups at each end to enable two molecules to be connected. Reactive groups include, for example, a maleimide group, an aldehyde group, an NHS ester, and the like. Further, specific examples of the linker when the ligand is not a protein include a polyethylene glycol and the like.

As described above, a suitable attachment mode for a given combination of the partial peptide according to an embodiment of the present invention and a ligand can be selected from among known attachment modes, considering the properties, structural relatedness, and others of the partial peptide and the ligand.

OTHER CONSIDERATIONS

The fusion protein or conjugated protein according to an embodiment of the present invention may intramolecularly include an active ingredient having a physiological activity (hereinafter, may also be referred to as an "active ingredient" as used herein). Alternatively, the fusion protein or conjugated protein according to an embodiment of the present invention need not include an active ingredient in a molecule. In that case, for example, a complex of the fusion protein or conjugated protein according to an embodiment of the present invention and an active ingredient (for example, nucleic acid and others) may be formed for intracellular delivery.

When the active ingredient is a protein, a fusion protein of the aforementioned partial peptide, an active ingredient, and, if desired, a protein (an antibody and the like) serving as a ligand can be prepared by a genetic engineering approach as in the partial peptide as described above. In that case, these peptides may be indirectly attached together through a linker by arranging the amino acid sequence of the linker between these peptides, or may be directly attached together without via a linker as described for the case of the ligand. The peptide encoded by the amino acid sequence of a linker may be similar to the linker to be arranged between the above ligand and the partial peptide. Further, there is no particular limitation for a region in which each peptide is located in a fusion protein. For example, a fusion protein may be designed to have a partial peptide, an active ingredient, and a ligand in this order from the side of the N-terminus, or may be designed to have an active ingredient, a ligand, and a partial peptide in this order from the side of the N-terminus, or may be designed to have an active ingredient, a partial peptide, and a ligand in this order from the side of the N-terminus. A fusion protein may be appropriately designed so as to show a desired effect depending on the properties of each protein. It is noted that the active ingredient may also act as a ligand. In that case, the fusion protein according to an embodiment of the present invention may be composed of only a ligand and a partial peptide.

When the active ingredient is a protein, examples of the active ingredient include, antibodies (scFv, Fab, domain antibodies, diabodies, and the like), cytotoxic protein toxins (*Pseudomonas* exotoxin, ribonuclease, and the like), reporter enzymes (fluorescent proteins, luciferase, β-galactosidase, horseradish peroxidase, and the like), biologically active peptides, and the like. When the active ingredient is a protein, there is no particular limitation for the molecular weight of the active ingredient, and it may be suitably selected according to the types, molecular weights, and the like of other peptides, and may be selected from, for example, the range of 1 to 1000 kDa.

When the active ingredient is not a protein, the active ingredient may be directly or indirectly attached to a partial peptide or a ligand. The active ingredient may be directly attached to a partial peptide or a ligand via chemical bonding by taking advantage of a functional group(s) present at the termini or in the internal portion of the partial peptide or the ligand. The mode of chemical bonding used in that case is selected according to the type(s) of the functional group(s) which will react with an active ingredient. Further, non-covalent bonding between avidin and biotin may also be used to attach a biotin-labelled active ingredient to a fusion protein of a partial peptide and avidin. Indirect attachment with a partial peptide or a ligand is mainly used when direct attachment is difficult, or indirect attachment is preferred. Indirect attachment may be achieved through a linker. A linker used in this case (that is, a linker when the active ingredient is not a protein) may be similar to the aforementioned linker between a partial peptide and a ligand.

Examples the active ingredient which is not a protein include low-molecular weight compounds (drugs such as anticancer agents and antibiotics used in antibody-drug conjugates ADCs; fluorescent dyes such as FITC and TAMRA; reporter units for MRI and PET; and the like), nucleic acid (DNA and mRNA which encode a suicide gene or a reporter gene, siRNA, shRNA, antisense oligonucleotides, aptamers, and the like), carbohydrate chains, radioactive isotopes, and the like.

The conjugated protein according to an embodiment of the present invention refers to a complex in which a partial peptide is attached to a non-protein component as described above, and, for example, may be a complex in which the aforementioned fusion protein is chemically attached to a non-protein component, a complex itself in which a partial peptide is attached to a non-protein component and/or an active ingredient, or a complex in which the above partial peptide is attached to a non-protein component other than a linker and an active ingredient.

When a non-protein component is attached to the conjugated protein according to an embodiment of the present invention, examples of that component include, for example, the aforementioned non-protein ligand, active ingredient, linker between them, and the like as well as, for example, lipids (phospholipid and the like) and natural polysaccharides (chitin, chitosan, hyaluronic acid, chondroitin sulfuric acid, and the like). Here, it is known that a nanoparticle such as a liposome and a natural polysaccharide complex may be used as a carrier for DDS. The conjugated protein according to an embodiment of the present invention can be used as a carrier which encapsulates the aforementioned non-protein active ingredient therein for intracellularly delivering an active ingredient by using, for example, a lipid or a natural polysaccharide capable of forming a nanoparticle. A conventionally known lipid or natural polysaccharide can be used for the lipid or natural polysaccharide capable of forming a nanoparticle, and can be appropriately selected according to types of the active ingredient, the ligand, and the like. Further, these non-protein components may be directly each attached to a partial peptide, a ligand, or an active ingredient, or may be indirectly attached via a linker.

In particular, a biopolymer such as a fusion protein has low cell membrane permeability. However, the fusion protein according to an embodiment of the present invention, which is fused with the aforementioned partial peptide, has high endosomal escape ability and shows excellent cell membrane permeability. In view of the above, a fusion protein is particularly suitable for an embodiment of the present invention.

There is no particular limitation for the molecular weight and size of the fusion protein or conjugated protein according to an embodiment of the present invention, and the molecular weight of the fusion protein or conjugated protein may be 100 to 1000 kDa, or the size (particle diameter) of the fusion protein or conjugated protein may be 1 to 200 nm.

The fusion protein or conjugated protein according to an embodiment of the present invention may also include a cationic peptide (for example, a TAT peptide, polyarginine, polylysine, polyhistidine) in the molecule thereof in order to improve cell membrane permeability. However, since cationic peptides interact electrostatically with anionic cell membranes, cell membrane permeability is increased, but cell uptake due to non-specific cell interaction occurs. Therefore, a cationic peptide is not preferred in view of delivery into a specific cell. In contrast, when an antibody, which has low cell membrane permeability, is used as a ligand, a cationic peptide such as a TAT peptide is required to be fused with the antibody to increase cell membrane permeability. On the other hand, the fusion protein or conjugated protein according to an embodiment of the present invention has superior cell membrane permeability. Therefore, high cell membrane permeability can be obtained even when a cationic peptide is not included in the molecule thereof. Rather, when a highly cell-selective ligand such as an antibody is used, a cationic peptide is preferably not included in order to prevent decreased cell selectivity. If a cationic peptide were included, cell selectivity would be decreased.

<Intracellular Delivery Carrier>

The intracellular delivery carrier according to an embodiment of the present invention includes the above fusion protein or conjugated protein.

There is no particular limitation for target cells, but the followings can be a target for delivery: for example, cells such as lung cells, colon cells, rectum cells, anus cells, bile duct cells, small intestine cells, gastric cells, esophagus cells, gallbladder cells, liver cells, pancreatic cells, appendix cells, breast cells, ovarian cells, cervical cells, prostate cells, kidney cells, glial cells, skin cells, lymph cells, villous cells, cervicofacial cells, osteogenic cells, and blood cells or cancer cells thereof (cervical cancer cells, lung cancer cells, colon cancer cells, rectum cancer cells, anus cancer cells, bile duct cancer cells, small intestine cancer cells, gastric cancer cells, esophagus cancer cells, gallbladder cancer cells, liver cancer cells, pancreatic cancer cells, appendix cancer cells, breast cancer cells, ovarian cancer cells, prostate cancer cells, kidney cancer cells, cancer cells of the central nervous system, glioblastoma cells, neuroblastoma cells, skin cancer cells, lymphoma cells, villous cancer cells, cervicofacial cancer cells, osteogenic sarcoma cells, blood cancer cells, and the like).

The intracellular delivery carrier according to an embodiment of the present invention can be intracellularly delivered by a conventionally known method. For example, the intracellular delivery carrier according to an embodiment of the present invention can be delivered to isolated cells by mixing the intracellular delivery carrier with the cells in vitro and performing culture. Alternatively, the intracellular delivery carrier according to an embodiment of the present invention can be delivered to an animal (non-human animal) in vivo via the mode of administration of oral administration or injection (intravenous, subcutaneous, or intramuscular injection, or the like).

<Cell Membrane Permeation Enhancer>

The present invention encompasses a cell membrane permeation enhancer including the aforementioned partial peptide. The term "cell membrane permeation enhancement" as used in the present invention includes enhancement of endosomal escape.

<DNA>

The prevent invention encompasses a fusion protein having a partial peptide consisting of at least seven consecutive amino acid residues of an amino acid sequence encoded by DNA set forth in any of the above (a) to (d) and a ligand attached directly or indirectly to the partial peptide, the ligand having a binding capability to a cell surface; or DNA encoding the partial peptide.

DNA encoding the above fusion protein can be prepared as in the DNA used for synthesis of the partial peptide.

<Vector>

The present invention encompasses a fusion protein having a partial peptide consisting of at least seven consecutive amino acid residues of an amino acid sequence encoded by DNA set forth in any of the above (a) to (d) and a ligand attached directly or indirectly to the partial peptide, the ligand having a binding capability to a cell surface; or a vector incorporating DNA encoding the partial peptide.

The vector according to an embodiment of the present invention may be similar to a suitable vector which can be used for synthesizing the aforementioned partial peptide.

EXAMPLES

<Selection of Candidates of Human-Derived Partial Peptide Having Cell Membrane Permeability>

As candidates of a human-derived partial peptide having cell membrane permeability (hereinafter, may also be referred to as a "human-derived cell membrane permeable peptide" as used herein), the following were selected: "IZUMO $1_{57-113}$" (SEQ ID NO: 12) which is a fusion core helix peptide near the N-terminus of a protein IZUMO 1 as a sperm-side factor related to recognition and fusion of a gamete upon fertilization; "CD9$_{113-194}$" (SEQ ID NO: 2) which is the second extracellular loop peptide including a 3-amino acid sequence (CCG) characteristic of the tetraspanin family near the C-terminus of a protein CD9 as an egg-side factor; and "Syncytin $1_{345-422}$" (SEQ ID NO: 13) which is a partial peptide of a coiled coil structure including the heptad repeat structure of a protein Syncytin 1 related to formation of a syncytial trophoderm cell in placenta; "Syncytin $1_{320-340}$ (FP)" (hereinafter, may also be referred to "Syncytin 1 (FP)" as used herein) (SEQ ID NO: 3); "Syncytin $1_{352-392}$ (NHR) (hereinafter, may also be referred to as "Syncytin 1 (NHR)" as used herein) (SEQ ID NO: 14); and "Syncytin $1_{407-440}$ (CHR)" (hereinafter, may also be referred to as "Syncytin 1 (CHR)" as used herein) (SEQ ID NO: 15). Further, "Syncytin 1 (FP-NHR)" (SEQ ID NO: 16), "Syncytin 1 (NHR-CHR)" (SEQ ID NO: 17), and "Syncytin 1 (FP-NHR-CHR)" (SEQ ID NO: 18) were selected as candidates of a human-derived cell membrane permeable peptide. It is noted that numbering in a subscript position indicated at the name of each peptide represents amino acid residues constituting the corresponding peptide when numbered from the side of the N-terminus of the original protein.

Further, a partial peptide B55 (SEQ ID NO: 19) derived from sea urchin was selected as a positive control of a cell membrane permeable peptide. The domain structures of the proteins including these peptides are shown in FIG. 1, and the amino acid sequences of these peptides are shown in Table 1. In FIG. 1, "SP" in "IZUMO 1" represents a signal peptide sequence (SP) at the N-terminus, and "TMD" in "IZUMO 1" represents a transmembrane domain at the side of the C-terminus, and "Ig-like" in "IZUMO 1" represents an Ig-like domain which is one of the extracellular domains. "TMD" in "CD9" represents each of the 4 transmembrane domains. "SU" and "TM" indicated above "Syncytin 1" represent two domains which constitute "Syncytin 1", and "CS" represents a cleavage site between these.

"SP" in "Syncytin 1" represents a signal peptide sequence at the N-terminus, and "TMD" represents a transmembrane domain at the side of the C-terminus. Moreover, as shown in FIG. 1, "FP (320 to 340 a. a.)" as a fusion peptide related to membrane fusion; "NHR" (352 to 392 a. a.) as a heptad repeat sequence at the N-terminus; and "CHR (407 to 440 a. a.)" as a heptad repeat sequence at the C-terminus in "Syncytin 1" each represent 3 motif sequences included in the TM domain. The numbers indicated at each domain in FIG. 1 represent the numbering of amino acid residues constituting the corresponding peptide when numbered from the side of the N-terminus of the original protein. In FIG. 1, regions selected as candidates of a human-derived partial peptide having cell membrane permeability are indicated by hatched lines for "IZUMO 1" and "CD9," indicated by their designated names in alphabet for "Syncytin 1 (FP)," "Syncytin 1 (NHR)," and "Syncytin 1 (CHR)", and indicated by a numerical value in a subscript position for "Syncytin $1_{345-422}$."

TABLE 1

| Peptide Name | Amino acid sequence (N→C) |
| --- | --- |
| IZUMO$1_{57-118}$ | VDEATLQKGSWSLLKDLKRITDSDVKG DLFVKELFWMLHLQKETFATYVARFQK EAY |
| IZUMO$1_{57-75}$ | VDEATLQKGSWSLLKDLKR |
| IZUMO$1_{76-94}$ | ITDSDVKGDLFVKELFWML |
| IZUMO$1_{95-113}$ | HLQKETFATYVARFQKEAY |
| IZUMO$1_{81-113}$ | VKGDLFVKELFWMLHLQKETFATYVAR FQKEAY |
| CD$9_{113-194}$ | HKDEVIKEVQEFYKDTYNKLKTKDEPQ RETLKAIHYALNCCGLAGGVEQFISDI CPKKDVLETFTVKSCPDAIKEVFDNKF H |
| Syncytin$1_{945-422}$ | QFYYKLSQELNGDMERVADSLVTLQDQ LNSLAAVVLQNRRALDLLTAERGGTCL FLGEECCYYVNQSGIVTEKVKEIR |
| Syncytin1 (FP) | ILPFVIGAGVLGALGTGIGGI |
| Syncytin1 (NHR) | QELNGDMERVADSLVTLQDQLNSLAAV VLQNRRALDLLTAE |
| Syncytin1 (CHR) | YVNQSGIVTEKVKEIRDRIQRRAEELR NTGPWGL |
| Syncytin1 (FP-NHR) | ILPFVIGAGVLGALGTGIGGITTSTQF YYKLSQELNGDMERVADSLVTLQDQLN SLAAVVLQNRRALDLLTAE |
| Syncytin1 (NHR-CHR) | QELNGDMERVADSLVTLQDQLNSLAAV VLQNRRALDLLTAERGGTCLFLGEECC YYVNQSGIVTEKVKEIRDRIQRRAEEL RNTGPWGL |
| Syncytin1 (FP-NHR-CHR) | ILPFVIGAGVLGALGTGIGGITTSTQF YYKLSQELNGDMEKVADSLVTLQDQLN SLAAVVLQNRRALDLLTAERGGTCLFL GEECCYYVNQSGIVTEKVKEIRDRIQR RAEELRNTGPWGL |
| 6xHis | HHHHHH |
| FLAG | DYKDDDDK |
| TCS | LVPRGS |
| eGFP | MVSKGEELFTGVVPILVELDGDVNGII KFSVSGEGEGDATYGKLTLKFICTTGK LPVPWPTLVTTLTYGVQCFSRYPDHMK QHDFFKSAMPEGYVQERTIFFKDDGNY KTRAEVKFEGDTLVNRIELKGIDFKED GNILGHKLEYNYNSHNVYIMADKQKNG IKVNFKIRHNIEDGSVQLADHYQQNTP IGDGPVLLPDNHYLSTQSALSKDPNEK RDHMVLLEFVTAAGITLCMDELYKGS |
| B55 | KAVLGATKIDLPVDINDPYDLGLLLRH LRHHSNLLANIGDPAVREQVLSAMQEE E |
| HA2 | GLFEAIEGFIENGWEGMIDGWYG |
| TAT | YGRKKRRQRRR |

<Preparation of eGFP-Fused Proteins>

First, in order to confirm that a candidate of a human-derived cell membrane permeable peptide did not bind non-selectively to a cell membrane, a fusion protein of each of the aforementioned partial peptides and eGFP (enhanced green fluorescent protein) (hereinafter, a fusion protein including eGFP may also be referred to as an "eGFP-fused protein" as used herein) was expressed in E. coli, and purified. Then localization of eGFP after added to cultured cells was observed under a fluorescence microscope. Schematic diagrams of the DNA constructs of the produced various eGFP-fused proteins are shown in FIG. 2. FIG. 2(a) schematically shows the DNA constructs of eGFP-fused proteins of human-derived membrane-acting peptide candidates (an eGFP-fused protein of "Syncytin $1_{345-422}$" for a partial peptide of Syncytin 1). FIG. 2(b) schematically shows the DNA constructs of eGFP-fused proteins of the partial peptides from the domains of Syncytin 1. The terms "6×His" and "FLAG" refer to base sequences which encode tags used for purifying an eGFP-fused protein, and the term "TCS" refers to a thrombin cleavage sequence. The term "$(G_4S)_3$" refers to a flexible linker having a three-times repeated GGGGS-encoding base sequence arranged between eGFP and Syncytin 1 (FP). It is noted that a base sequence encoding "IZUMO $1_{57-113}$" is set forth in SEQ ID NO: 20, and a base sequence encoding "$CD9_{113-194}$" is set forth in SEQ ID NO: 21, and a base sequence encoding "Syncytin $1_{345-422}$" is set forth in SEQ ID NO: 22, and a base sequence encoding "Syncytin 1 (FP)" is set forth in SEQ ID NO: 23, and a base sequence encoding "Syncytin 1 (NHR)" is set forth in SEQ ID NO: 24, and a base sequence encoding "Syncytin 1 (CHR)" is set forth in SEQ ID NO: 25, and a base sequence encoding "Syncytin 1 (FP-NHR)" is set forth in SEQ ID NO: 26, and a base sequence encoding "Syncytin 1 (NHR-CHR)" is set forth in SEQ ID NO: 27, and a base sequence encoding "Syncytin 1 (FP-NHR-CHR)" is set forth in SEQ ID NO: 28.

A plasmid in which one of these DNA was inserted into pET20b (Novagen) was introduced into *E. coli* BL21-CodonPlus (DE3)-RIPL (Agilent Technologies), cultured at 20° C. for 3 days in a 2×YT medium, and then harvested. Harvested cells were suspended in 500 μL TBS (Tris-buffered saline) (1 mM PMSF), and sonicated with Sonifier® 250 (Branson) to collect a soluble fraction. The remaining pellet was suspended in 500 μL Urea-TBS (6 M Urea, in TBS) (1 mM PMSF), and then vortexed at 4° C. for 1 hour to collect an insoluble fraction. For eGFP, the eGFP-$CD9_{113-194}$ fusion protein, the eGFP-Syncytin $1_{345-422}$ fusion protein, the eGFP-Syncytin 1 (FP) fusion protein, the eGFP-Syncytin 1 (NHR) fusion protein, the eGFP-Syncytin 1 (CHR) fusion protein, the eGFP-Syncytin 1 (FP-NHR) fusion protein, the eGFP-Syncytin 1 (NHR-CHR) fusion protein, and the eGFP-Syncytin 1 (FP-NHR-CHR) fusion protein, the soluble fraction was further purified using COSMOGEL® His-Accept (Nacalai Tesque). For eGFP-B55 and eGFP-$CD9_{113-194}$, the insoluble fraction was purified and then refolded by dialysis using a Slide-A-Lyzer™ dialysis cassette (Thermo Scientific).

<Observation Tests of Cell-Membrane Binding Properties of eGFP-Fused Proteins>

Each of the eGFP-fused proteins obtained in the above "Preparation of eGFP-fused proteins" was added to HeLa cells. The cells were then fixed with 4% paraformaldehyde after 24 hours, and localization of eGFP was observed under a confocal microscope FV-1000 (Olympus Corporation). As a result, strong binding to a cell membrane was observed for the eGFP-B55 fusion protein and the eGFP-Syncytin $1_{345-422}$ fusion protein. Further, the eGFP-$CD9_{113-194}$ fusion protein, the eGFP-Syncytin 1 (FP) fusion protein, the eGFP-Syncytin 1 (CHR) fusion protein, and the eGFP-Syncytin 1 (NHR-CHR) fusion protein showed weak binding to a cell membrane. Other fusion proteins (eGFP-IZUMO $1_{57-113}$ fusion protein, the eGFP-Syncytin 1 (NHR) fusion protein, the eGFP-Syncytin 1 (FP-NHR) fusion protein, and the eGFP-Syncytin 1 (FP-NHR-CHR) fusion protein did not show any binding to a cell membrane at all.

<Preparation of eGFP-TAT-Containing Fusion Proteins>

In the observation tests of binding properties as described above, strong binding to a cell membrane was not observed for the fusion proteins of human-derived cell membrane permeable peptides other than eGFP-Syncytin $1_{345-422}$. In view of the above findings, an eGFP-fused protein in which the TAT peptide (SEQ ID NO: 29, YGRKKRRQRRR) as a cationic peptide capable of interacting with a cell membrane was added to the C-terminus (hereinafter, the eGFP-containing fusion protein in which TAT was added to the C terminus as used herein may also be referred to the "eGFP-TAT-containing fusion protein.") was prepared to investigate whether the human-derived peptide would promote endosomal escape of eGFP unselectively incorporated into the cell through TAT. It is noted that an HA2 peptide from influenza virus (SEQ ID NO: 30, GLFEAIEGFIENGWEG-MIDGWYG) was prepared as a positive control of a cell membrane permeable peptide. Schematic diagrams of the DNA constructs of the various eGFP-TAT-containing fusion proteins prepared are shown in FIG. 3. FIG. 3(a) schematically shows the DNA constructs of the eGFP-TAT fusion protein and eGFP-TAT-containing fusion proteins each including HA2 or a candidate of a human-derived cell membrane permeable peptide (except Syncytin 1). FIG. 3(b) schematically shows the DNA constructs of eGFP-TAT-containing fusion proteins of the partial peptides from the domains of Syncytin 1. The terms "6×His" and "FLAG" in FIG. 3 refer to base sequences which encode tags used for purifying an eGFP fusion protein, and the term "TCS" refers to a thrombin cleavage sequence. The term "$(G_4S)_3$" refers to a flexible linker having a three-times repeated GGGGS-encoding base sequence arranged between eGFP and Syncytin 1 (FP). These eGFP-TAT-containing fusion proteins were expressed under the same conditions as described in the above "Preparation of eGFP-fused proteins." Then, for the eGFP-TAT fusion protein, the eGFP-HA2-TAT fusion protein, the eGFP-$CD9_{113-194}$-TAT fusion protein, the eGFP-Syncytin 1 (NHR)-TAT fusion protein, and the eGFP-Syncytin 1 (CHR)-TAT fusion protein, a soluble fraction was purified under the same conditions as used for "eGFP" in the above "Preparation of eGFP-fused proteins." Further, for the eGFP-IZUMO $1_{57-113}$-TAT fusion protein and the eGFP-Syncytin 1 (FP)-TAT fusion protein, an insoluble fraction was purified under the same conditions as used for "eGFP-B55" in the above "Preparation of eGFP-fused proteins." It is noted that in the present description and drawings, the eGFP-TAT fusion protein may be referred to as Control Example, and the eGFP-HA2-TAT fusion protein may be referred to as Reference Example, and the eGFP-IZUMO $1_{57-113}$-TAT fusion protein may be referred to as Example 1, and the eGFP-$CD9_{113-194}$-TAT fusion protein may be referred to as Example 2, and the eGFP-Syncytin 1 (FP)-TAT fusion protein may be referred to as Example 3, and the eGFP-Syncytin 1 (NHR)-TAT fusion protein may be referred to as Comparative Example 1, and the eGFP-Syncytin 1 (CHR)-TAT fusion protein may be referred to as Comparative Example 2. Further, the amino acid sequence of the eGFP-TAT fusion protein (Control Example) is set forth SEQ ID NO: 31, and the amino acid sequence of the eGFP-HA2-TAT fusion protein (Reference Example) is set forth in SEQ ID NO: 32, and the amino acid sequence of the eGFP-IZUMO $1_{57-113}$-TAT fusion protein (Example 1) is set forth in SEQ ID NO: 33, and the amino acid sequence of the eGFP-$CD9_{113-194}$-TAT fusion protein (Example 2) is set forth in SEQ ID NO: 34, and the amino acid sequence of the eGFP-Syncytin 1 (FP)-TAT fusion protein (Example 3) is set forth in SEQ ID NO: 35, and the amino acid sequence of the eGFP-Syncytin 1 (NHR)-TAT fusion protein (Comparative Example 1) is set forth in SEQ ID NO: 36, and the amino acid sequence of the eGFP-Syncytin 1 (CHR)-TAT fusion protein (Comparative Example 2) is set forth in SEQ ID NO: 37.

<Observation Under Confocal Microscope and Measurement of Fluorescence Intensity of Intracellularly Delivered eGFP-TAT-Containing Fusion Proteins>

The eGFP-TAT-containing fusion proteins prepared in the above "Preparation of eGFP-TAT-containing fusion proteins" were each added to HeLa cells, and then fixed after one hour. The fluorescence on the surface of a cell membrane was then quenched with trypan blue to perform observation under a confocal microscope. Here, the eGFP-TAT fusion protein was added to HeLa cells to give a final concentration of 10 µM, and the eGFP-HA2-TAT fusion protein was added to HeLa cells to give a final concentration of 10 µM, and the eGFP-IZUMO $1_{57-113}$-TAT fusion protein was added to HeLa cells to give a final concentration of 0.2 µM, and the eGFP-CD9$_{113-194}$-TAT fusion protein was added to HeLa cells to give a final concentration of 5 µM, and the eGFP-Syncytin 1 (FP)-TAT fusion protein was added to HeLa cells to give a final concentration of 10 µM, and the eGFP-Syncytin 1 (NHR)-TAT fusion protein was added to HeLa cells to give a final concentration of 10 µM, and the eGFP-Syncytin 1 (CHR)-TAT fusion protein was added to HeLa cells to give a final concentration of 10 µM.

Observation under a confocal microscope after nucleus labelling with Hoechst® revealed that the eGFP-IZUMO $1_{57-113}$-TAT fusion protein (Example 1), the eGFP-CD9$_{113-194}$-TAT fusion protein (Example 2), and the eGFP-Syncytin 1 (FP)-TAT fusion protein (Example 3) showed eGFP fluorescence throughout the cytoplasm as in the eGFP-HA2-TAT fusion protein (Reference Example) as a positive control. In contrast, inspection of the confocal microscope images revealed that the eGFP-Syncytin 1 (NHR)-TAT fusion protein (Comparative Example 1) and the eGFP-Syncytin 1 (CHR)-TAT fusion protein (Comparative Example 2) merely showed fluorescence comparable to that of the eGFP-TAT fusion protein (Control Example). These results suggested that the partial peptides IZUMO $1_{57-113}$, CD9$_{113-194}$, and Syncytin 1 (FP) promoted endosomal escape. Further, the eGFP-Syncytin 1 (FP-NHR)-TAT fusion protein and the eGFP-Syncytin 1 (FP-NHR-CHR)-TAT fusion protein also showed similar localization as in the eGFP-Syncytin 1 (FP). This is likely due to an effect of Syncytin 1 (FP) for promoting cell membrane permeation. It is noted that the eGFP-Syncytin 1 (NHR-CHR)-TAT fusion protein showed promoted uptake into endosome, but not localization of eGFP throughout the cytoplasm. This suggested that endosomal escape did not occur.

Figure 5:
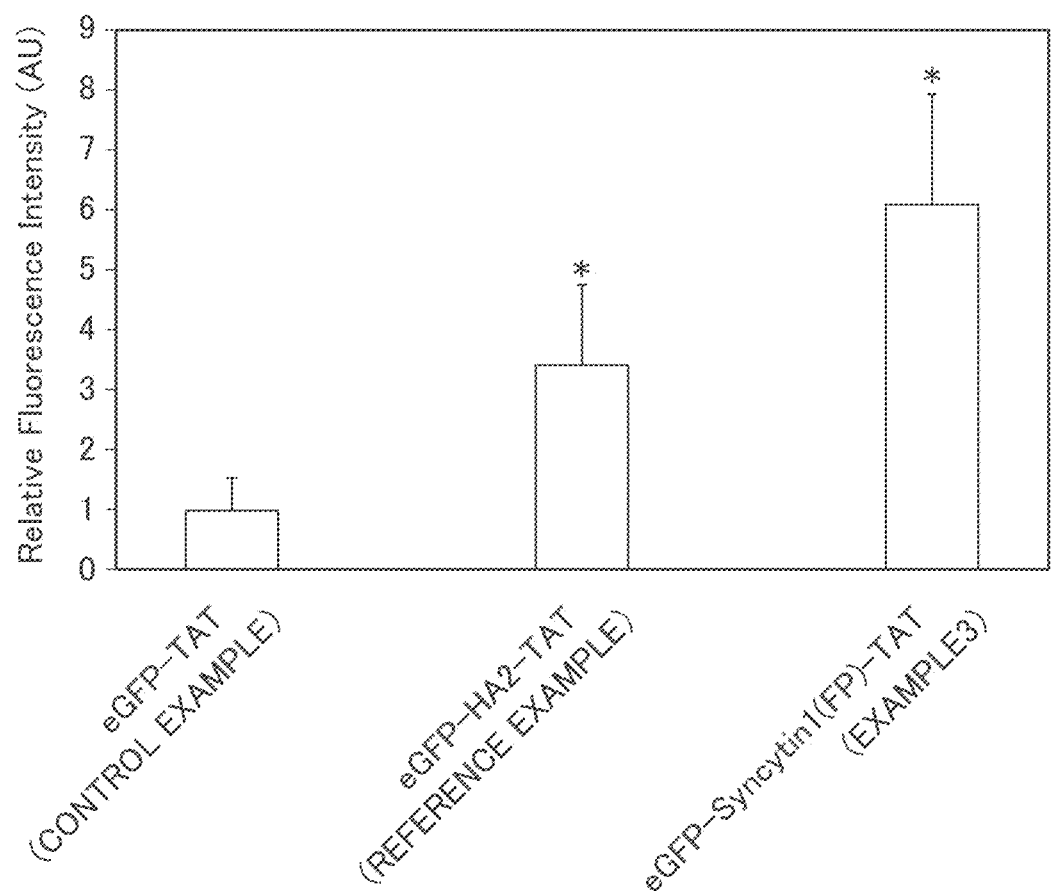
FIG. 5 shows a graph of the fluorescence intensities for the eGFP-TAT fusion protein, the eGFP-HA2-TAT fusion protein, and an eGFP-Syncytin 1 (FP)-TAT fusion protein.

After delivery of each fusion protein into HeLa cells, the region of interest (ROI) was taken per cell, and the fluorescence intensity of eGFP was quantified. Results are shown in FIGS. 4 and 5. FIG. 4 shows a graph of the fluorescence intensities for the eGFP-TAT fusion protein, the eGFP-HA2-TAT fusion protein, the eGFP-IZUMO $1_{57-113}$-TAT fusion protein, and the eGFP-CD9$_{113-194}$-TAT fusion protein. FIG. 5 shows a graph of the fluorescence intensities for the eGFP-TAT fusion protein, the eGFP-HA2-TAT fusion protein, and the eGFP-Syncytin 1 (FP)-TAT fusion protein. It is noted that the fluorescence intensities shown in FIGS. 4 and 5 are relative fluorescence intensities of each fusion protein relative to the fluorescence intensity of "eGFP-TAT." The results revealed that the eGFP-IZUMO $1_{57-113}$-TAT fusion protein, the eGFP-CD9$_{113-194}$-TAT fusion protein, and the eGFP-Syncytin 1 (FP)-TAT fusion protein showed a significantly increased amount of intracellular localization as compared with the eGFP-TAT fusion protein. Further, the results revealed that the eGFP-IZUMO $1_{57-113}$-TAT fusion protein, the eGFP-CD9$_{113-194}$-TAT fusion protein, and the eGFP-Syncytin 1 (FP)-TAT fusion protein each showed an increased amount of intracellular localization as compared with the eGFP-HA2-TAT fusion protein. Therefore, these results demonstrated that IZUMO $1_{57-113}$, CD9$_{113-194}$, and Syncytin 1 (FP) had a higher cell membrane permeability effect than the HA2 peptide as a virus-derived cell membrane permeable peptide. In particular, these results revealed that the eGFP-IZUMO $1_{57-113}$-TAT fusion protein showed a higher amount of intracellular fluorescence even at a concentration as low as 0.2 µM than the eGFP-HA2-TAT fusion protein at 10 µM. This suggests that use of IZUMO $1_{57-113}$ as a human-derived cell membrane permeation enhancing peptide can likely provide a more efficient drug delivery system.

<Study of Endosomal Escape Ability>

The results from "Observation under confocal microscope and measurement of fluorescence intensity of intracellularly delivered eGFP-TAT-containing fusion proteins" suggested that IZUMO $1_{57-113}$, CD9$_{113-194}$, and Syncytin 1 (FP) had a function as a cell membrane permeation enhancing peptide. In order to study whether these eGFP-TAT-containing fusion proteins were released from endosome, endosome was stained with LysoTracker® Red DND-99 (Life Technologies), and co-localization with each eGFP-TAT-containing fusion protein was analyzed. It is noted that if quenching were performed with trypan blue, the entire cell would show red fluorescence, preventing labeling of endosome with LysoTracker®. Therefore, the eGFP-TAT-containing fusion protein on the surface of a cell membrane was removed by washing with heparin/PBS. Detailed procedures will be described below.

First, the eGFP-TAT fusion protein, the eGFP-HA2-TAT fusion protein, the eGFP-IZUMO $1_{57-113}$-TAT fusion protein, the eGFP-CD9$_{113-194}$-TAT fusion protein, and the eGFP-Syncytin 1 (FP)-TAT fusion protein purified after the above "Preparation of eGFP-TAT-containing fusion proteins" were each introduced into HeLa cells for one hour, and then washed with heparin/PBS. The cells were then fixed, and observed under a confocal microscope. Here, the eGFP-TAT fusion protein was added to HeLa cells to give a final concentration of 10 µM, and the eGFP-HA2-TAT fusion protein was added to HeLa cells to give a final concentration of 10 µM, and the eGFP-IZUMO $1_{57-113}$-TAT fusion protein was added to HeLa cells to give a final concentration of 1 µM, and the eGFP-CD9$_{113-194}$-TAT fusion protein was added to HeLa cells to give a final concentration of 5 µM, and the eGFP-Syncytin 1 (FP)-TAT fusion protein was added to HeLa cells to give a final concentration of 5 µM. It is noted that nuclei were labelled with Hoechst®, and endosome was labelled with LysoTracker®. The results revealed that the GFP-TAT fusion protein showed eGFP fluorescence which was mostly consistent with LysoTracker® fluorescence while the other proteins showed more eGFP fluorescence which was not consistent with LysoTracker® fluorescence.

Figure 6:
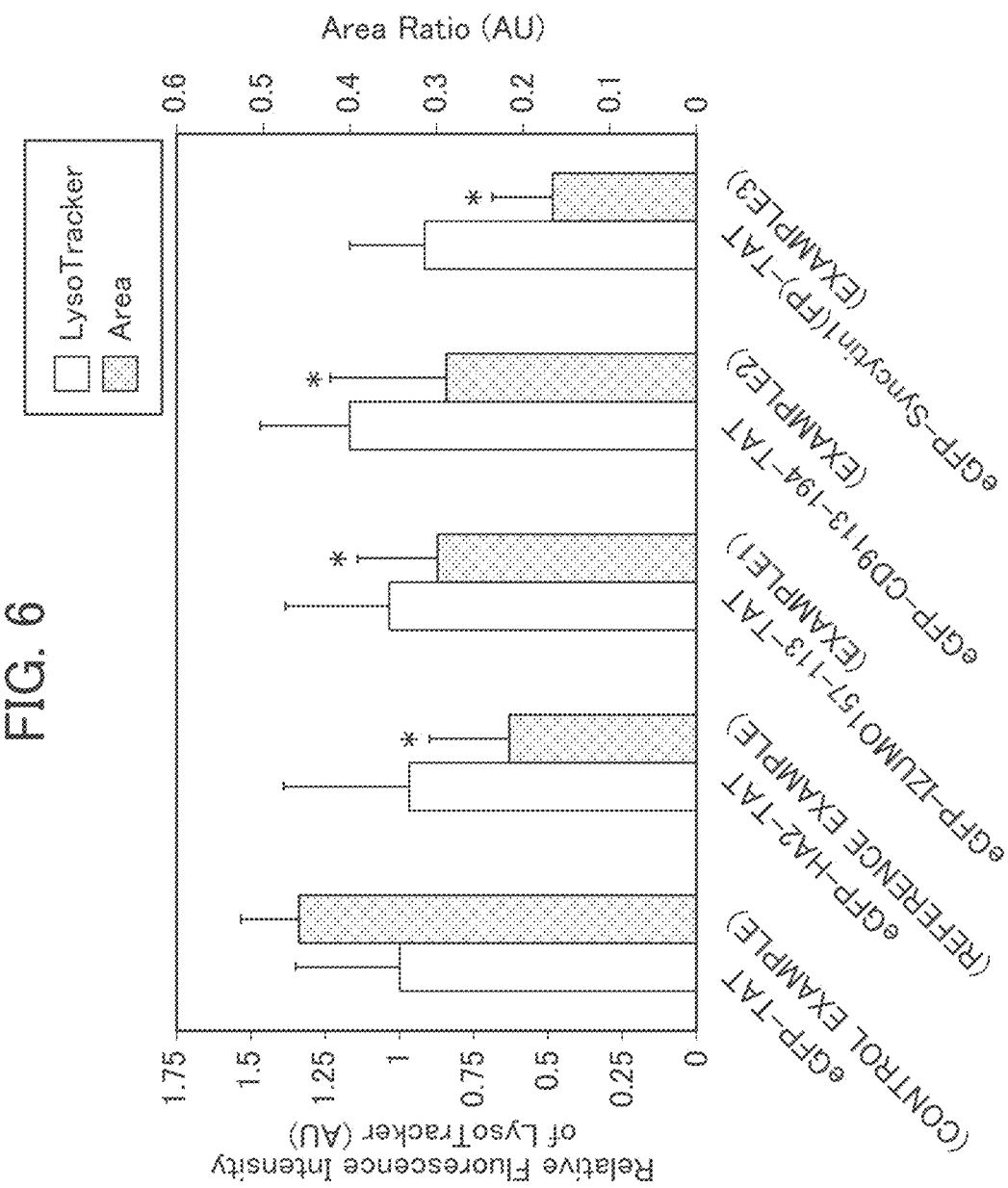
FIG. 6 shows graphs of the area ratio (right axis) of the area where the fluorescence of intercellular eGFP is co-localized with the fluorescence of LysoTracker® to the area of the fluorescence of eGFP and the fluorescence intensities of LysoTracker® (left axis) for the eGFP-TAT fusion protein, the eGFP-HA2-TAT fusion protein, the eGFP-IZUMO $1_{57-113}$-TAT fusion protein, the eGFP-CD9$_{113-194}$-TAT fusion protein, and the eGFP-Syncytin 1 (FP)-TAT fusion protein after delivery into Hela cells.

Further, after delivery of each fusion protein into HeLa cells, the region of interest (ROI) was taken per cell, and the area ratio of an area where the fluorescence of eGFP was co-localized with the fluorescence of LysoTracker® in a cell to an area of the fluorescence of eGFP (that is, the ratio of an area where each fusion protein was co-localized with endosome to an area where the fusion protein was localized); and the fluorescence intensity of LysoTracker® were quantified. Results are shown in FIG. 6. As shown in FIG. 6, the results from the quantification of the area ratio where the fluorescence of eGFP was co-localized with the fluorescence of LysoTracker® in a cell and the fluorescence intensity of LysoTracker® revealed that the eGFP-TATcontaining fusion proteins showed significantly lower ratios of co-localization with endosome, in comparison to eGFP-TAT (the right axis (Area) in FIG. 6), that is, that they had been released from endosome. In contrast, the fluorescence intensity of LysoTracker® in each cell was found not to be significantly different in every case (the left axis (LysoTracker) in FIG. 6), suggesting that endocytosis was not affected.

<Optimization of Peptide Sequence of IZUMO 1>

Figure 7:
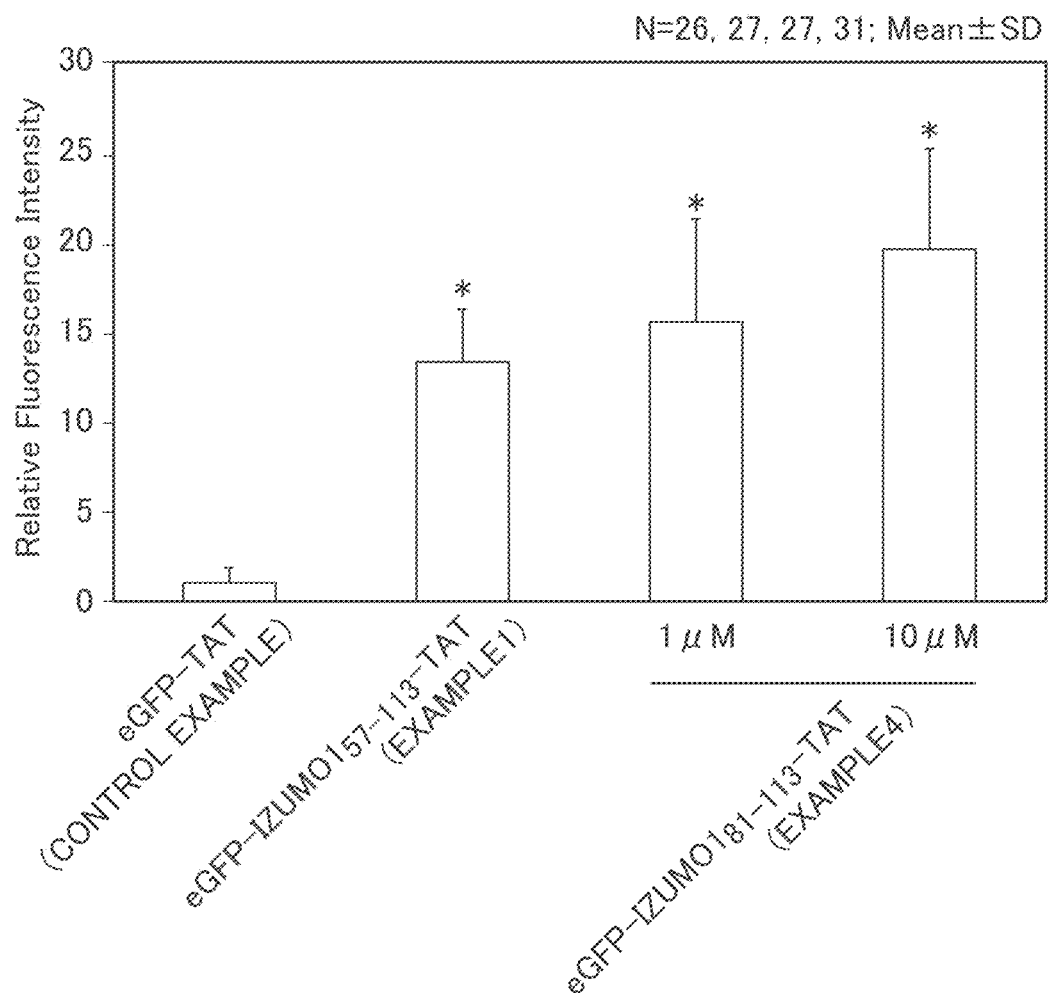
FIG. 7 shows a graph of the fluorescence intensities for the eGFP-TAT fusion protein (final concentration: 10 µM), the eGFP-IZUMO $1_{57-113}$-TAT fusion protein (final concentration: 1 µM), an eGFP-IZUMO $1_{81-113}$-TAT fusion protein (final concentration: 1 µM), and the eGFP-IZUMO $1_{81-113}$-TAT fusion protein (final concentration: 10 µM).
Figure 8:
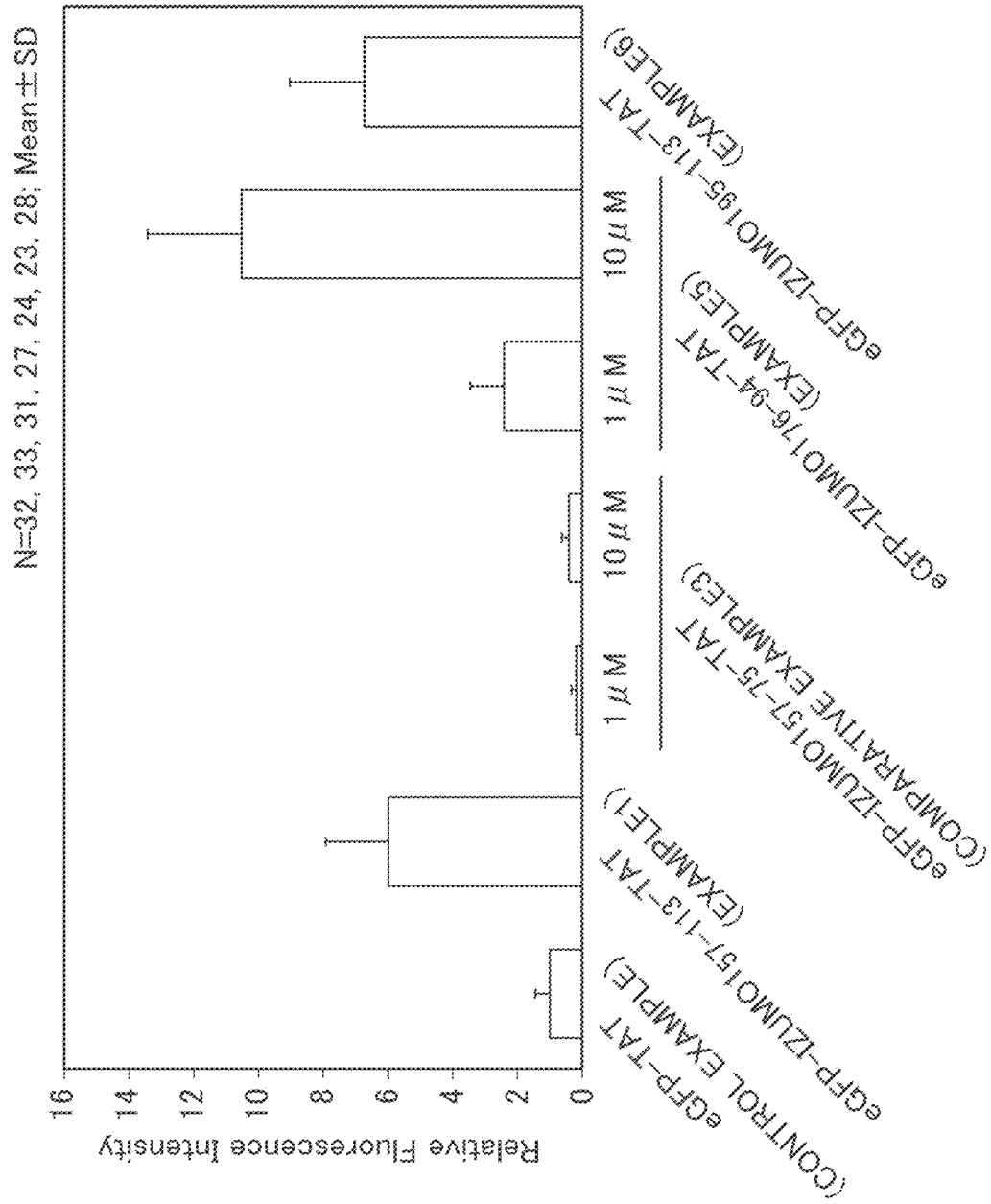
FIG. 8 shows a graph of the fluorescence intensities for the eGFP-TAT fusion protein (final concentration: 10 µM), the eGFP-IZUMO $1_{57-113}$-TAT fusion protein (final concentration: 1 µM), an eGFP-IZUMO $1_{57-75}$-TAT fusion protein (final concentration: 1 µM), the eGFP-IZUMO $1_{57-75}$-TAT fusion protein (final concentration: 10 µM), an eGFP-IZUMO $1_{76-94}$-TAT fusion protein (final concentration: 1 µM), the eGFP-IZUMO $1_{76-94}$-TAT fusion protein (final concentration: 10 µM), and an eGFP-IZUMO $1_{95-113}$-TAT fusion protein (final concentration 1 µM).

A peptide for use as a human-derived cell membrane permeation enhancing peptide is preferably shorter in view of manipulation. Therefore, for IZUMO $1_{57-75}$ (SEQ ID NO: 38), IZUMO $1_{76-94}$ (SEQ ID NO: 4), IZUMO $1_{95-113}$ (SEQ ID NO: 6), and IZUMO $1_{81-113}$ (SEQ ID NO: 5) which were further fragmented in a shorter form from IZUMO $1_{57-113}$, corresponding eGFP-TAT-containing fusion proteins were prepared in a similar way as used for the "eGFP-IZUMO $1_{57-113}$-TAT fusion protein" described in the above "Preparation of eGFP-TAT-containing fusion proteins." These fusion proteins were each delivered into HeLa cells, and the fluorescence intensity of eGFP uptaken into the cells was quantified. More specifically, the eGFP-TAT fusion protein was added to Hela cells to give a final concentration of 10 µM, and the eGFP-IZUMO $1_{57-113}$-TAT fusion protein was added to Hela cells to give a final concentration of 1 µM, and the eGFP-IZUMO $1_{95-113}$-TAT fusion protein was added to Hela cells to give a final concentration of 1 µM, and the eGFP-IZUMO $1_{57-75}$-TAT fusion protein was added to Hela cells to give a final concentration of 1 µM or 10 µM, and the eGFP-IZUMO $1_{76-94}$-TAT fusion protein was added to Hela cells to give a final concentration of 1 µM or 10 µM, and the eGFP-IZUMO $1_{81-113}$-TAT fusion protein was added to Hela cells to give a final concentration of 1 µM or 10 µM. The HeLa cells were fixed one hour after the addition, and the fluorescence on the surface of a cell membrane was quenched with trypan blue. Then observation was performed under a confocal microscope. After delivery of each fusion protein into HeLa cells, the region of interest (ROI) was taken per cell, and the fluorescence intensity of eGFP was quantified. Results are shown in FIGS. 7 and 8. It is noted that in the present description and drawings, the eGFP-IZUMO $1_{81-113}$-TAT fusion protein may be referred to as Example 4, and the eGFP-IZUMO $1_{76-94}$-TAT fusion protein may be referred to as Example 5, and the eGFP-IZUMO $1_{95-113}$-TAT fusion protein may be referred to Example 6, and the eGFP-IZUMO $1_{57-75}$-TAT fusion protein may be referred to as Comparative Example 3. Further, the eGFP-IZUMO $1_{81-113}$-TAT fusion protein (Example 4) is set forth in SEQ ID NO: 39, and the eGFP-IZUMO $1_{76-94}$-TAT fusion protein (Example 5) is set forth in SEQ ID NO: 40, and the eGFP-IZUMO $1_{95-113}$-TAT fusion protein (Example 6) is set forth in SEQ ID NO: 41, and the eGFP-IZUMO $1_{57-75}$-TAT fusion protein (Comparative Example 3) is set forth in SEQ ID NO: 42.

As shown in FIGS. 7 and 8, the eGFP-IZUMO $1_{57-75}$-TAT fusion protein (Comparative Example 3) showed a lower fluorescence intensity than the eGFP-TAT fusion protein (Control Example) while the eGFP-IZUMO $1_{81-113}$-TAT fusion protein (Example 4), the eGFP-IZUMO $1_{76-94}$-TAT fusion protein (Example 5), and the eGFP-IZUMO $1_{95-113}$-TAT fusion protein (Example 6) showed a higher fluorescence intensity than the eGFP-TAT fusion protein (Control Example). In particular, the eGFP-IZUMO $1_{81-113}$-TAT fusion protein (Example 4) showed the highest value, which was about 20 times higher than that of the eGFP-TAT fusion protein (Control Example) having no IZUMO 1 peptide. These results showed that a partial peptide of IZUMO 1 consisting of amino acid residues from position 76 to position 113 (SEQ ID NO: 1) has high endosomal escape ability and an excellent effect for enhancing cell membrane permeability.

<Secondary Structure Prediction of Peptide Sequences>

For the regions including the three types of human-derived cell membrane permeation enhancing peptides IZUMO $1_{57-113}$, CD9$_{113-194}$, Syncytin $1_{320-440}$, secondary structures such as a helix, a β-sheet, a coil, and the like were predicted using the secondary structure prediction server JPred4 (compbio.dundee.ac.uk/jpred4/). Results are shown in FIG. 9. The symbol "H" in FIG. 9 represents a portion which constitutes a helix in each peptide. As shown in FIG. 9, the prediction showed that IZUMO 1 had 2 helices, and CD9 and Syncytin 1 had 3 helices. According to the above fragmentation experiments of the peptide sequence of IZUMO 1, a fragment including a helix portion of residues 81 to 110 which corresponds to the second half of the amino acid residues of IZUMO 1, and a fragment including a helix portion of residues 321 to 334 which corresponds to the first half of the amino acid residues of Syncytin 1 showed a high efficiency of cell membrane permeation. These results suggested that these helical structures are important for interaction with a cell membrane. Further, similarly to IZUMO 1 and Syncytin 1, it was suggested that a fragment including a helix of residues 115 to 133 (SEQ ID NO: 7) or residues 138 to 151 (SEQ ID NO: 8) or residues 182 to 190 (SEQ ID NO: 9) in CD9 is important.

<Quantification of Endosomal Escape Efficiency of eGFP-TAT-Containing Fusion Proteins>

As shown in the above "Study of endosomal escape ability," the eGFP-TAT-containing fusion proteins were found to have been released from endosome. Further, the following experiments were performed in order to quantify endosomal escape efficiency of the eGFP-TAT-containing fusion proteins.

First, prepared was an eGFP-TAT-containing fusion protein having a nuclear localization signal sequence (NLS) added to the C-terminus (hereinafter, a fusion protein including eGFP and having TAT and NLS added to the C-terminus may be referred to as the "eGFP-TAT-NLS-containing fusion protein" as used herein). The schematic diagrams of the DNA constructs of the produced eGFP-TAT-NLS-containing fusion proteins are shown in FIG. 10. The terms "6×His," "FLAG," "TCS" and "(G$_4$S)$_3$" in FIG. 10 have the same meanings as those in FIG. 2. The term "FP'" in FIG. 10 represents "Syncytin $1_{372-340}$ (FP')" (SEQ ID NO: 44, Table 3) which is a peptide shortened by 2 amino acids from "Syncytin $1_{370-340}$ (FP)" (SEQ ID NO: 3). The nuclear localization signal sequence (NLS) is set forth in SEQ ID NO: 43 (Table 3). The above eGFP-TAT-NLS-containing fusion proteins were expressed under the same conditions as described in the above "Preparation of eGFP-fused proteins."

Subsequently, for the eGFP-NLS fusion protein, the eGFP-TAT-NLS fusion protein, the eGFP-HA2-TAT-NLS fusion protein, and the eGFP-Syncytin $1_{372-340}$ (FP')-TAT-NLS fusion protein, a soluble fraction was purified under the same conditions as used for "eGFP" in the above "Preparation of eGFP-fused proteins." Moreover, for the eGFP-IZUMO $1_{57-113}$-TAT-NLS fusion protein and the eGFP-Syncytin $1_{320-340}$ (FP)-TAT-NLS fusion protein, an insoluble fraction was purified under the same conditions as used for "eGFP-B55" in the above "Preparation of eGFP-fused proteins."

The resulting eGFP-TAT-NLS-containing fusion proteins were studied to estimate endosomal escape efficiency based on the number of molecules of each fusion protein which was translocated into the nucleus in accordance with the following method. This was achieved by taking advantage of the fact that only a fusion protein which had been released from endosome and localized into the cytoplasm was to be translocated into the nucleus through importin. First, one hour after adding each purified fusion protein to HeLa cells, the cells were washed 3 times with PBS, detached with a scraper, and centrifugally recovered. A portion of this was sampled to count the number of cells with a hemocytometer. The collected cells were solubilized using NE-PER nuclear and cytoplasmic extraction reagents (Thermo Fisher Scientific), and fractionated into a nuclear fraction and a non-nuclear fraction. A fusion protein remaining inside endosome is to be contained in the non-nuclear fraction. Therefore, a fusion protein contained in the nuclear fraction is likely to be a protein released from endosome. Accordingly, a fusion protein contained in the nuclear fraction was quantified by Western blotting using anti-FLAG antibody, and the result was divided by the number of cells to calculate the average number of molecules of the protein contained in the nuclear fraction per cell. Results are shown in Table 2. It is noted that in the present specification and drawings, the eGFP-IZUMO $1_{57-113}$-TAT-NLS fusion protein may be referred to Example 7, and the eGFP-Syncytin $1_{320-340}$ (FP)-TAT-NLS fusion protein may be referred to as Example 8, and the eGFP-Syncytin $1_{322-340}$ (FP')-TAT-NLS fusion protein may be referred to as Example 9.

TABLE 2

| Peptide Name | Average number of molecules per cell included in nuclear fraction Mean ± SD ($10^7$ molecules/cell) |
|---|---|
| eGFP-NLS | 0.013 ± 0.005 |
| eGFP-TAT-NLS | 0.072 ± 0.026 |
| eGFP-HA2-TAT-NLS | 0.33 ± 0.09 |
| eGFP-IZUMO1$_{57-113}$-TAT-NLS (Example 7) | 0.26 ± 0.10 |
| eGFP-Syncytin1$_{320-340}$(FP)-TAT-NLS (Example 8) | 2.5 ± 0.4 |
| eGFP-Syncytin1$_{322-340}$(FP')-TAT-NLS (Example 9) | 6.4 ± 0.25 |

As understood from Table 2, the fusion proteins including the partial peptide (IZUMO $1_{57-113}$, FP, FP') according to an embodiment of the present invention all showed a large number of molecules contained in the nuclear fraction per cell, demonstrating a high endosomal escape efficiency. In particular, the FP'-containing fusion protein showed a significantly large number of molecules, and was capable of delivering about 20 times as many molecules into the cytoplasm as compared with a conventional cell membrane permeable peptide including HA2 "eGFP-HA2-TAT-NLS," and was capable of delivering about 100 times as many molecules into the cytoplasm as compared with "eGFP-TAT-NLS."

<Delivery of eGFP-Syncytin $1_{322-340}$-TAT into Various Human Cultured Cells>

Figure 11:
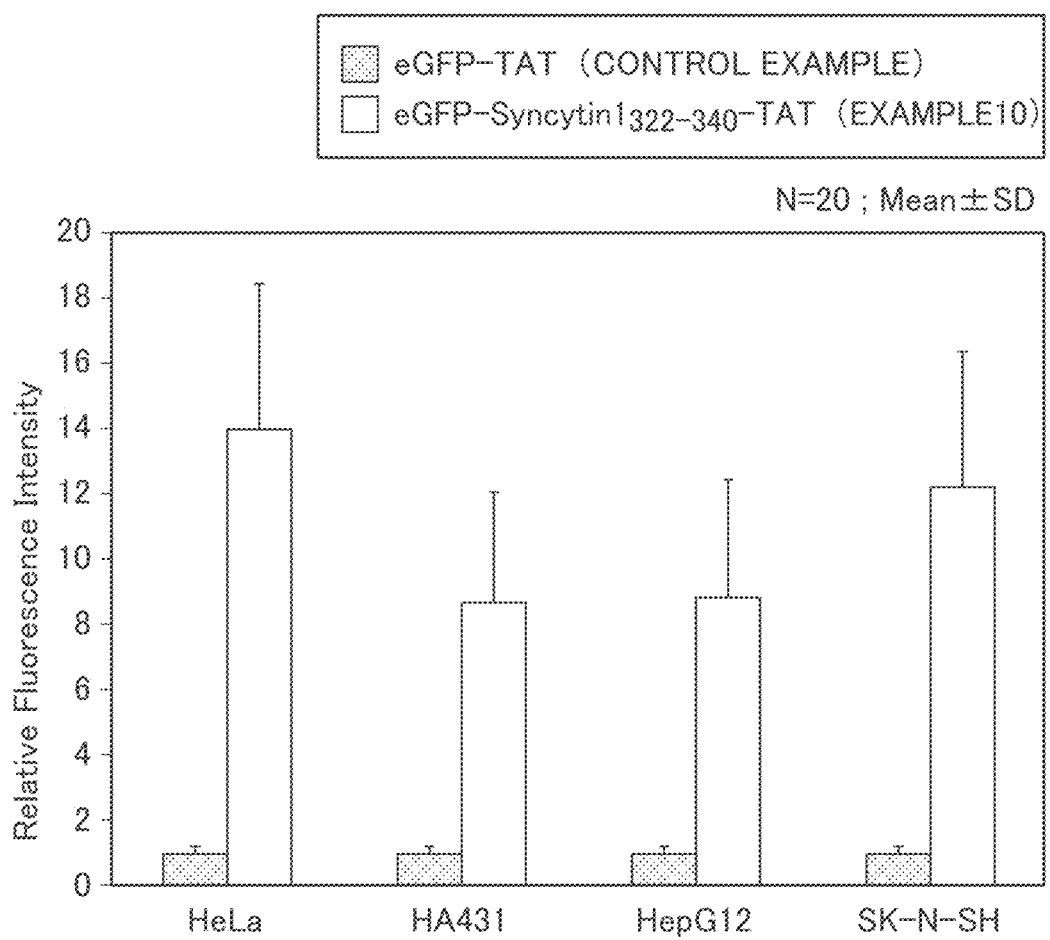
FIG. 11 shows a graph of the fluorescence intensities for an eGFP-Syncytin $1_{322-340}$-TAT fusion protein and the eGFP-TAT fusion protein when added to HeLa (human cervical cancer cells), A431 (human epidermoid carcinoma cells), HepG2 (human liver cancer cells), and SK-N-SH (human neuroblastoma cells).

The eGFP-TAT-containing fusion proteins were also found to be uptaken into human cultured cells other than HeLa cells. First, as an eGFP-TAT-containing fusion protein, eGFP-Syncytin $1_{372-340}$-TAT (SEQ ID NO: 45, Table 3) was prepared by a similar way as used for the "eGFP-IZUMO $1_{57-113}$-TAT fusion protein" in the above "Preparation of eGFP-TAT-containing fusion proteins." The resulting fusion protein was added to HeLa (human cervical cancer cells), A431 (human epidermoid carcinoma cells), HepG2 (human liver cancer cells), and SK-N-SH (human neuroblastoma cells) to give a final concentration of 5 μM. The cells were fixed one hour after the addition, and the fluorescence on the surface of a cell membrane was then quenched with trypan blue, and then observed under a confocal microscope. After delivered into each type of cells, the region of interest (ROI) was taken per cell, and the fluorescence intensity of eGFP was quantified. Results are shown in FIG. 11. It is noted that in the present description and drawings, the eGFP-Syncytin $1_{322-340}$-TAT fusion protein may be referred to as Example 10.

As shown in FIG. 11, the eGFP-Syncytin $1_{322-340}$-TAT fusion protein (Example 10) showed higher fluorescence intensity than the eGFP-TAT fusion protein (Control Example) in all of the cell types. This demonstrated that Syncytin $1_{372-340}$ (SEQ ID NO: 44) showed high endosomal escape efficiency and an excellent cell membrane permeation enhancing effect for various types of human cells.

<Intracellular Delivery of Proteins Other than eGFP>

Whether Syncytin $1_{322-340}$ (SEQ ID NO: 44) was able to promote endosomal escape of a protein other than eGFP was studied. Specifically, a SNAP tag (molecular weight 19.4 kDa) [Nat. Biotechnol. 21 (2003) 86-89] or β-galactosidase (molecular weight 116 kDa) was used instead of eGFP, and TAT fusion proteins were prepared by a similar method as used for "eGFP-IZUMO $1_{57-113}$-TAT fusion protein" in the above "Preparation of eGFP-TAT-containing fusion proteins." Each of the resulting fusion proteins was added to HeLa cells to give a final concentration of 5 μM, and the SNAP tag and β-galactosidase (β-Gal) uptaken into the cells were quantified in accordance with the following method.

Figure 12:
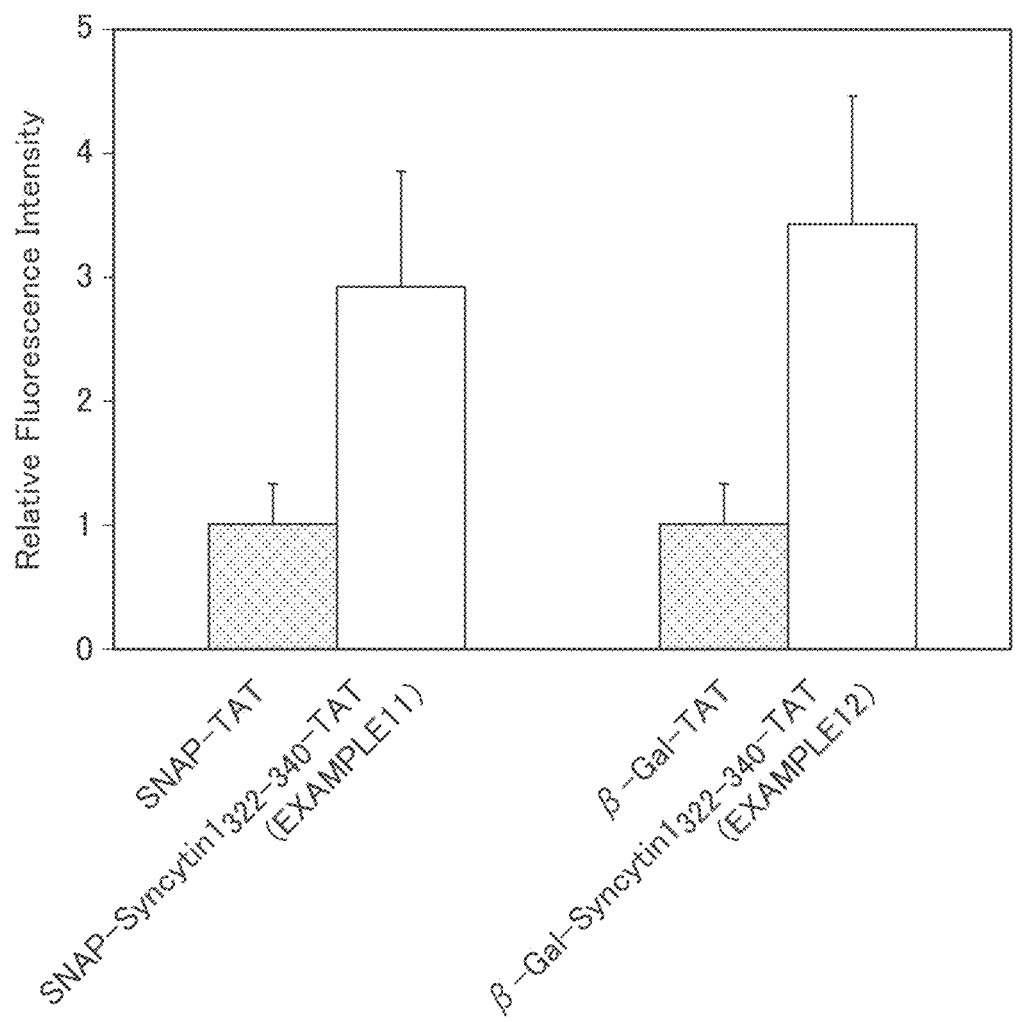
FIG. 12 shows a graph of the fluorescence intensities for a SNAP-Syncytin $1_{322-340}$-TAT fusion protein, a SNAP-TAT fusion protein, a β-Gal-Syncytin $1_{322-340}$-TAT fusion protein, and a β-Gal-TAT fusion protein.

First, the fusion protein having a SNAP tag instead of eGFP (a SNAP-Syncytin $1_{322-340}$-TAT fusion protein, SEQ ID NO: 46, Table 3) having fluorescently pre-labeled benzylguanine (BG-DY505) attached via covalent bond was delivered into HeLa cells. Then, the region of interest (ROI) was taken per cell and fluorescence intensity was quantified. For the fusion protein having β-galactosidase instead of eGFP (a β-Gal-Syncytin $1_{372-340}$-TAT fusion protein, SEQ ID NO: 47, Table 3), a substrate (C12-FDG) which shows fluorescence when decomposed due to the enzyme activity after addition to HeLa cells was added, and the fluorescence intensity thereof was quantified. Results are shown in FIG. 12. It is noted that in the present description and drawings, the SNAP-Syncytin $1_{372-340}$-TAT fusion protein may be referred to as Example 11, and the β-Gal-Syncytin $1_{372-340}$-TAT fusion protein may be referred to as Example 12.

As shown in FIG. 12, the SNAP-Syncytin $1_{322-340}$-TAT fusion protein (Example 11) and the β-Gal-Syncytin $1_{322-340}$-TAT fusion protein (Example 12) each showed a higher fluorescence intensity than the SNAP-TAT fusion protein (SEQ ID NO: 48, Table 4) and the β-Gal-TAT fusion protein (SEQ ID NO: 49, Table 4) as Control Examples which did not have the Syncytin $1_{322-340}$ peptide. These results demonstrated that Syncytin $1_{322-340}$ showed high endosomal escape efficiency and an excellent cell membrane permeation enhancing effect for proteins other than eGFP.

TABLE 3

| Peptide Name | Amino acid sequence (N→C) |
|---|---|
| NLS | RREKYGIPEPPEPKRRK |
| Syncytin1$_{322-340}$ | PFVIGAGVLGALGTGIGGI |

TABLE 3-continued

| Peptide Name | Amino acid sequence (N→C) |
|---|---|
| eGFP-Syncytin1₃₂₂₋₃₄₀-TAT | MHHHHHHDYKDDDDKLVPRGSMVSKGE ELFTGVVPILVELDGDVNGHKFSVSGE GEGDATYGKLTLKFICTTGKLPVPWPT LVTTLTYGVQCFSRYPDHMKQHDFFKS AMPEGYVQERTIFFKDDGNYKTRAEVK FEGDTLVNRIELKGIDEKEDGNILGHK LEYNYNSHNVYIMADKQKNGIKVNFKI RHNIEDGSVQLADHYQQNTPIGDGPVL LPDNHYLSTQSALSKDPNEKRDHMVLL EFVTAAGITLGMDELYKGSPFVIGAGV LGALGTGIGGIYGRKKRRQRRR |
| SNAP-Syncytin1₃₂₂₋₃₄₀-TAT | MHHHHHHDYKDDDDKLVPRGSMDKDCE MKRTTLDSPLGKLELSGCEQGLHEIIF LGKGTSAADAVEVPAPAAVLGGPEPLM QATAWLNAYFHQPEAIEEFPVPALHHP VFQQESFTRQVLWKLLKVVKFGEVISY SHLAALAGNPAATAAVKTALSGNPVPI LIPCHRVVNINGDVGGYEGGLAVKEWL LAHEGHRLGKPGLGGSPFVIGAGVLGA LGTGIGGIYGRKKRRQRRR |
| β-Gal-Syncytin1₃₂₂₋₃₄₀-TAT | MHHHHHHDYKDDDDKLVPRGSMGTMIT DSLAVVLQRRDWENPGVTQLNRLAAHP PFASWRNSEEARTDRPSQQLRSLNGEW RFAWFPAPEAVPESWLECDLPEADTVV VPSNWQMHGYDAPIYTNVTYPITVNPP FVPTENPTGCYSLTFNVDESWLQEGQT RIIFDGVNSAFHLWCNGRWVGYGQDSR LPSEFDLSAFLRAGENRLAVMVLRWSD GSYLEDQDMWRMSGIFRDVSLLHKPTT QISDFHVATRFNDDFSRAVLEAEVQMC GELRDYLRVTVSLWQGETQVASGTAPF GGEIIDERGGYADRVTLRLNVENPKLW SAEIPNLYRAVVELHTADGTLIEAEAC DVGFREVRIENGLLLLNGKPLLIRGVN RHEHHPLHGQVMDEQTMVQDILLMKQN NFNAVRCSHYPNHPLWYTLCDRYGLYV VDEANIETHGMVPMNRLTDDPRWLPAM SERVTRMVQRDRNHPSVIIWSLGNESG HGANHDALYRWIKSVDPSRPVQYEGGG ADTTATDIICPMYARVDEDQPFPAVPK WSIKKWLSLPGETRPLILCEYAHAMGN SLGGFAKYWQAFRQYPRLQGGFVWDWV DQSLIKYDENGNPWSAYGGDFGDTPND RQFCMNGLVFADRTPHPALTEAKHQQQ FFQFRLSGQTIEVTSEYLFRHSDNELL HWMVALDGKPLASGEVPLDVAPQGKQL IELPELPQPESAGQLWLTVRVVQPNAT AWSEAGHISAWQQWRLAENLSVTLPAA SHAIPHLTTSEMDFCIELGNKRWQFNR QSGFLSQMWIGDKKQLLTPLRDQFTRA PLDNDIGVSEATRIDPNAWVERWKAAG HYQAEAALLQCTADTLADAVLITTAHA WQHQGKTLFISRKTYRIDGSGQMAITV DVEVASDTPHPARIGLNCQLAQVAERV NWLGLGPQENYPDRLTAACFDRWDLPL SDMYTPYVFPSENGLRCGTRELNYGPH QWRGDFQFNISRYSQQQLMETSHRHLL HAEEGTWLNIDGFHMGIGGDDSWSPSV SAEFQLSAGRYHYQLVWCQKGSPFVIG AGVLGALGTGIGGIYGRKKRRQRRR |

TABLE 4

| Peptide Name | Amino acid sequence (N→C) |
|---|---|
| SNAP-TAT | MHHHHHHDYKDDDDKLVPRGSMDKDCEMKRTTLDSP LGKLELSGCEQGLHEIIFLGKGTSAADAVEVPAPAA VLGGPEPLMQATAWLNAYFHQPEAIEEFPVPALHHP VFQQESFTRQVLWKLLKVVKFGEVISYSHLAALAGN PAATAAVKTALSGNPVPILIPCHRVVNINGDVGGYE GGLAVKEWLLAHEGHRLGKPGLGGSYGRKKRRQRRR |
| β-Gal-TAT | MHHHHHHDYKDDDDKLVPRGSMGTMITDSLAVVLQR RDWENPGVTQLNRLAAHPPFASWRNSEEARTDRPSQ QLRSLNGEWRFAWFPAPEAVPESWLECDLPEADTVV VPSNWQMHGYDAPIYTNVTYPITVNPPFVPTENPTG CYSLTFNVDESWLQEGQTRIIFDGVNSAFHLWCNGR WVGYGQDSRLPSEFDLSAFLRAGENRLAVMVLRWSD GSYLEDQDMWRMSGIFRDVSLLHKPTTQISDFHVAT RFNDDFSRAVLEAEVQMCGELRDYLRVTVSLWQGET QVASGTAPFGGEIIDERGGYADRVTLRLNVENPKLW SAEIPNLYRAVVELHTADGTLIEAEACDVGFREVRI ENGLLLLNGKPLLIRGVNRHEHHPLHGQVMDEQTMV QDILLMKQNNFNAVRCSHYPNHPLWYTLCDRYGLYV VDEANIETHGMVPMNRLTDDPRWLPAMSERVTRMVQ RDRNHPSVIIWSLGNESGHGANHDALYRWIKSVDPS RPVQYEGGGADTTATDIICPMYARVDEDQPFPAVPK WSIKKWLSLPGETRPLILCEYAHAMGNSLGGFAKYW QAFRQYPRLQGGFVWDWVDQSLIKYDENGNPWSAYG GDFGDTPNDRQFCMNGLVFADRTPHPALTEAKHQQQ FFQFRLSGQTIEVTSEYLFRHSDNELLHWMVALDGK PLASGEVPLDVAPQGKQLIELPELPQPESAGQLWLT VRVVQPNATAWSEAGHISAWQQWRLAENLSVTLPAA SHAIPHLTTSEMDFCIELGNKRWQFNRQSGFLSQMW IGDKKQLLTPLRDQFTRAPLDNDIGVSEATRIDPNA WVERWKAAGHYQAEAALLQCTADTLADAVLITTAHA WQHQGKTLFISRKTYRIDGSGQMAITVDVEVASDTP HPARIGLNCQLAQVAERVNWLGLGPQENYPDRLTAA CFDRWDLPLSDMYTPYVFPSENGLRCGTRELNYGPH QWRGDFQFNISRYSQQQLMETSHRHLLHAEEGTWLN IDGFHMGIGGDDSWSPSVSAEFQLSAGRYHYQLVWC QKGSYGRKKRRQRRR |

---

The invention claimed is:

1. A fusion protein or conjugated protein comprising a partial peptide consisting of an amino acid sequence encoded by DNA set forth in any of (a) to (d), and
   a ligand directly attached to the partial peptide, the ligand having a binding capability to a receptor on a cell surface,
   wherein the partial peptide has cell membrane permeability and endosomal escape ability,
   (a) DNA consisting of a base sequence encoding an amino acid sequence set forth in SEQ ID NO: 1, 2, or 3,
   (b) DNA consisting of a base sequence capable of hybridizing under stringent conditions with a base sequence complementary to a base sequence encoding an amino acid sequence set forth in SEQ ID NO: 1, 2, or 3,
   (c) DNA consisting of a base sequence encoding an amino acid sequence where three or fewer amino acids are substituted, three or fewer amino acids are deleted, or three or fewer amino acids are added to an amino acid sequence set forth in SEQ ID NO: 3, and
   (d) DNA consisting of a base sequence encoding an amino acid sequence consisting of 90% or more identity with an amino acid sequence set forth in SEQ ID NO: 1, 2, or 3.

2. The fusion protein according to claim 1.

3. An intracellular delivery carrier comprising the fusion protein or conjugated protein according to claim 1.

4. DNA encoding the fusion protein according to claim 1.

5. A vector having the DNA according to claim 4.

6. The fusion protein or conjugated protein according to claim 1, wherein the ligand comprises an antibody.

7. The fusion protein according to claim 6.

8. The intracellular delivery carrier comprising the fusion protein according to claim 6.

9. DNA encoding the fusion protein according to claim 6.

10. The fusion protein or conjugated protein according to claim 1(c), wherein three or fewer amino acids having an aliphatic side chain are substituted.

11. The fusion protein or conjugated protein according to claim 10, wherein three or fewer glycine (G) residues are substituted.

12. The fusion protein or conjugated protein according to claim 11, wherein three or fewer glycine (G) residues are substituted with alanine (A) residues.

13. The fusion protein or conjugated protein according to claim 1, wherein the ligand comprises a TAT peptide.

14. The fusion protein or conjugated protein according to claim 13, wherein the TAT peptide is positioned at the N-terminus of the fusion protein or conjugated protein.

15. The fusion protein or conjugated protein according to claim 13, wherein the TAT peptide is positioned at the C-terminus of the fusion protein or conjugated protein.

16. The fusion protein or conjugated protein according to claim 13, wherein the TAT peptide comprises SEQ ID NO: 29.

17. The fusion protein or conjugated protein according to claim 1(d), wherein the DNA consists of a base sequence encoding an amino acid sequence consisting of 90% or more identity with an amino acid sequence set forth in SEQ ID NO: 1 or 2.

18. The fusion protein or conjugated protein according to claim 17, wherein three or fewer amino acids having an aliphatic side chain are substituted.

19. The fusion protein or conjugated protein according to claim 17, wherein the DNA consists of a base sequence encoding an amino acid sequence consisting of 90% or more identity with the amino acid sequence of SEQ ID NO: 2.

20. A fusion protein or conjugated protein comprising:
    a partial peptide set forth in (a) or (b) below, wherein the partial peptide has cell membrane permeability and endosomal escape ability, and
    a ligand directly attached to the partial peptide, the ligand having a binding capability to a receptor on a cell surface:
    (a) the partial peptide consisting of an amino acid sequence set forth in SEQ ID NO: 1, 2, or 3, or an amino acid sequence set forth in SEQ ID NO: 44; or
    (b) the partial peptide consisting of an amino acid sequence consisting of 90% or more identity with the amino acid sequence set forth in SEQ ID NO: 1, 2, or 3, or the amino acid sequence set forth in SEQ ID NO: 44.

* * * * *

SEQUENCE LISTING

<160> NUMBER OF SEQ ID NOS: 77

<210> SEQ ID NO 1
<211> LENGTH: 38
<212> TYPE: PRT
<213> ORGANISM: Homo sapiens

<400> SEQUENCE: 1

Ile Thr Asp Ser Asp Val Lys Gly Asp Leu Phe Val Lys Glu Leu Phe
1               5                   10                  15

Trp Met Leu His Leu Gln Lys Glu Thr Phe Ala Thr Tyr Val Ala Arg
            20                  25                  30

Phe Gln Lys Glu Ala Tyr
            35

<210> SEQ ID NO 2
<211> LENGTH: 82
<212> TYPE: PRT
<213> ORGANISM: Homo sapiens

<400> SEQUENCE: 2

His Lys Asp Glu Val Ile Lys Glu Val Gln Glu Phe Tyr Lys Asp Thr
1               5                   10                  15

Tyr Asn Lys Leu Lys Thr Lys Asp Glu Pro Gln Arg Glu Thr Leu Lys
            20                  25                  30

Ala Ile His Tyr Ala Leu Asn Cys Cys Gly Leu Ala Gly Gly Val Glu
        35                  40                  45

Gln Phe Ile Ser Asp Ile Cys Pro Lys Lys Asp Val Leu Glu Thr Phe
    50                  55                  60

Thr Val Lys Ser Cys Pro Asp Ala Ile Lys Glu Val Phe Asp Asn Lys
65                  70                  75                  80

Phe His

<210> SEQ ID NO 3
<211> LENGTH: 21
<212> TYPE: PRT
<213> ORGANISM: Homo sapiens

<400> SEQUENCE: 3

Ile Leu Pro Phe Val Ile Gly Ala Gly Val Leu Gly Ala Leu Gly Thr
1               5                   10                  15

Gly Ile Gly Gly Ile
            20

<210> SEQ ID NO 4
<211> LENGTH: 19
<212> TYPE: PRT
<213> ORGANISM: Homo sapiens

<400> SEQUENCE: 4

Ile Thr Asp Ser Asp Val Lys Gly Asp Leu Phe Val Lys Glu Leu Phe
1               5                   10                  15

Trp Met Leu

<210> SEQ ID NO 5
<211> LENGTH: 33
<212> TYPE: PRT
<213> ORGANISM: Homo sapiens

<400> SEQUENCE: 5

Val Lys Gly Asp Leu Phe Val Lys Glu Leu Phe Trp Met Leu His Leu
1               5                   10                  15

Gln Lys Glu Thr Phe Ala Thr Tyr Val Ala Arg Phe Gln Lys Glu Ala
            20                  25                  30

Tyr

<210> SEQ ID NO 6
<211> LENGTH: 19
<212> TYPE: PRT
<213> ORGANISM: Homo sapiens

<400> SEQUENCE: 6

His Leu Gln Lys Glu Thr Phe Ala Thr Tyr Val Ala Arg Phe Gln Lys
1               5                   10                  15

Glu Ala Tyr

<210> SEQ ID NO 7
<211> LENGTH: 19
<212> TYPE: PRT
<213> ORGANISM: Homo sapiens

<400> SEQUENCE: 7

Asp Glu Val Ile Lys Glu Val Gln Glu Phe Tyr Lys Asp Thr Tyr Asn
1               5                   10                  15

Lys Leu Lys

<210> SEQ ID NO 8
<211> LENGTH: 14
<212> TYPE: PRT
<213> ORGANISM: Homo sapiens

<400> SEQUENCE: 8

Pro Gln Arg Glu Thr Leu Lys Ala Ile His Tyr Ala Leu Asn
1               5                   10

<210> SEQ ID NO 9
<211> LENGTH: 9
<212> TYPE: PRT
<213> ORGANISM: Homo sapiens

<400> SEQUENCE: 9

Pro Asp Ala Ile Lys Glu Val Phe Asp
1               5

<210> SEQ ID NO 10
<211> LENGTH: 14
<212> TYPE: PRT
<213> ORGANISM: Homo sapiens

<400> SEQUENCE: 10

Leu Pro Phe Val Ile Gly Ala Gly Val Leu Gly Ala Leu Gly
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 11

Gly Gly Gly Gly Ser Gly Gly Gly Ser Gly Gly Gly Gly Ser
1               5                   10                  15

<210> SEQ ID NO 12
<211> LENGTH: 57
<212> TYPE: PRT
<213> ORGANISM: Homo sapiens

<400> SEQUENCE: 12

Val Asp Glu Ala Thr Leu Gln Lys Gly Ser Trp Ser Leu Leu Lys Asp
1               5                   10                  15

Leu Lys Arg Ile Thr Asp Ser Asp Val Lys Gly Asp Leu Phe Val Lys
                20                  25                  30

Glu Leu Phe Trp Met Leu His Leu Gln Lys Glu Thr Phe Ala Thr Tyr
            35                  40                  45

Val Ala Arg Phe Gln Lys Glu Ala Tyr
    50                  55

<210> SEQ ID NO 13
<211> LENGTH: 78
<212> TYPE: PRT
<213> ORGANISM: Homo sapiens

<400> SEQUENCE: 13

Gln Phe Tyr Tyr Lys Leu Ser Gln Glu Leu Asn Gly Asp Met Glu Arg
1               5                   10                  15

Val Ala Asp Ser Leu Val Thr Leu Gln Asp Gln Leu Asn Ser Leu Ala
            20                  25                  30

Ala Val Val Leu Gln Asn Arg Arg Ala Leu Asp Leu Leu Thr Ala Glu
        35                  40                  45

Arg Gly Gly Thr Cys Leu Phe Leu Gly Glu Glu Cys Cys Tyr Tyr Val
    50                  55                  60

Asn Gln Ser Gly Ile Val Thr Glu Lys Val Lys Glu Ile Arg
65                  70                  75

<210> SEQ ID NO 14
<211> LENGTH: 41
<212> TYPE: PRT
<213> ORGANISM: Homo sapiens

<400> SEQUENCE: 14

Gln Glu Leu Asn Gly Asp Met Glu Arg Val Ala Asp Ser Leu Val Thr
1               5                   10                  15

Leu Gln Asp Gln Leu Asn Ser Leu Ala Ala Val Val Leu Gln Asn Arg
            20                  25                  30

Arg Ala Leu Asp Leu Leu Thr Ala Glu
        35                  40

<210> SEQ ID NO 15
<211> LENGTH: 34
<212> TYPE: PRT
<213> ORGANISM: Homo sapiens

<400> SEQUENCE: 15

Tyr Val Asn Gln Ser Gly Ile Val Thr Glu Lys Val Lys Glu Ile Arg
1               5                   10                  15

Asp Arg Ile Gln Arg Arg Ala Glu Leu Arg Asn Thr Gly Pro Trp
            20                  25                  30

Gly Leu

<210> SEQ ID NO 16
<211> LENGTH: 73
<212> TYPE: PRT
<213> ORGANISM: Homo sapiens

<400> SEQUENCE: 16

Ile Leu Pro Phe Val Ile Gly Ala Gly Val Leu Gly Ala Leu Gly Thr
1               5                   10                  15

Gly Ile Gly Gly Ile Thr Thr Ser Thr Gln Phe Tyr Tyr Lys Leu Ser
            20                  25                  30

Gln Glu Leu Asn Gly Asp Met Glu Arg Val Ala Asp Ser Leu Val Thr
        35                  40                  45

Leu Gln Asp Gln Leu Asn Ser Leu Ala Ala Val Val Leu Gln Asn Arg
    50                  55                  60

```
Arg Ala Leu Asp Leu Leu Thr Ala Glu
 65                  70

<210> SEQ ID NO 17
<211> LENGTH: 89
<212> TYPE: PRT
<213> ORGANISM: Homo sapiens

<400> SEQUENCE: 17

Gln Glu Leu Asn Gly Asp Met Glu Arg Val Ala Asp Ser Leu Val Thr
  1               5                  10                  15

Leu Gln Asp Gln Leu Asn Ser Leu Ala Ala Val Val Leu Gln Asn Arg
             20                  25                  30

Arg Ala Leu Asp Leu Leu Thr Ala Glu Arg Gly Gly Thr Cys Leu Phe
         35                  40                  45

Leu Gly Glu Glu Cys Cys Tyr Tyr Val Asn Gln Ser Gly Ile Val Thr
     50                  55                  60

Glu Lys Val Lys Glu Ile Arg Asp Arg Ile Gln Arg Arg Ala Glu Glu
 65                  70                  75                  80

Leu Arg Asn Thr Gly Pro Trp Gly Leu
                 85

<210> SEQ ID NO 18
<211> LENGTH: 121
<212> TYPE: PRT
<213> ORGANISM: Homo sapiens

<400> SEQUENCE: 18

Ile Leu Pro Phe Val Ile Gly Ala Gly Val Leu Gly Ala Leu Gly Thr
  1               5                  10                  15

Gly Ile Gly Gly Ile Thr Thr Ser Thr Gln Phe Tyr Tyr Lys Leu Ser
             20                  25                  30

Gln Glu Leu Asn Gly Asp Met Glu Arg Val Ala Asp Ser Leu Val Thr
         35                  40                  45

Leu Gln Asp Gln Leu Asn Ser Leu Ala Ala Val Val Leu Gln Asn Arg
     50                  55                  60

Arg Ala Leu Asp Leu Leu Thr Ala Glu Arg Gly Gly Thr Cys Leu Phe
 65                  70                  75                  80

Leu Gly Glu Glu Cys Cys Tyr Tyr Val Asn Gln Ser Gly Ile Val Thr
                 85                  90                  95

Glu Lys Val Lys Glu Ile Arg Asp Arg Ile Gln Arg Arg Ala Glu Glu
            100                 105                 110

Leu Arg Asn Thr Gly Pro Trp Gly Leu
            115                 120

<210> SEQ ID NO 19
<211> LENGTH: 55
<212> TYPE: PRT
<213> ORGANISM: Strongylocentrotus purpuratus

<400> SEQUENCE: 19

Lys Ala Val Leu Gly Ala Thr Lys Ile Asp Leu Pro Val Asp Ile Asn
  1               5                  10                  15

Asp Pro Tyr Asp Leu Gly Leu Leu Leu Arg His Leu Arg His His Ser
             20                  25                  30

Asn Leu Leu Ala Asn Ile Gly Asp Pro Ala Val Arg Glu Gln Val Leu
         35                  40                  45

Ser Ala Met Gln Glu Glu Glu
     50                  55
```

<210> SEQ ID NO 20
<211> LENGTH: 171
<212> TYPE: DNA
<213> ORGANISM: Artificial Sequence
<220> FEATURE:
<223> OTHER INFORMATION: Synthetic polynucleotide

<400> SEQUENCE: 20
gtggatgaag ccacgttaca gaaagggtca tggtcactgc tgaaggattt gaaacgcatt        60
acggattctg atgtaaaagg ggatctgttt gtgaaagaac tgttttggat gttacatctg       120
cagaaagaaa ccttcgcgac ctatgttgcg cgcttccaga aggaagccta t                171

<210> SEQ ID NO 21
<211> LENGTH: 246
<212> TYPE: DNA
<213> ORGANISM: Artificial Sequence
<220> FEATURE:
<223> OTHER INFORMATION: Synthetic polynucleotide

<400> SEQUENCE: 21
cataaggatg aagtcatcaa agaagttcag gagttctaca agacaccta taacaaactg         60 aaaaccaaag atgaaccgca acgcgaaact tgaaagcga ttcactatgc actgaattgc        120
tgtggcttag ctggtggggt agaacagttc attagcgaca tttgcccgaa gaagatgtt        180 ctggaaacgt ttacagtgaa atcgtgtcca gatgccatca agaggtgtt tgacaacaag        240 tttcat                                                                  246

<210> SEQ ID NO 22
<211> LENGTH: 234
<212> TYPE: DNA
<213> ORGANISM: Artificial Sequence
<220> FEATURE:
<223> OTHER INFORMATION: Synthetic polynucleotide

<400> SEQUENCE: 22
cagttctact acaagctgag tcaggaactg aatggggata tggaacgcgt agcggattcg        60
ttggttacct tacaggacca actgaacagc ttagcagcgg ttgtgctgca gaatcgtcgt       120
gcccttgatc tgctgactgc tgaacgcggt ggtacctgtt tgtttctggg cgaagaatgc       180
tgctattatg tcaaccaatc cggcattgtg acggagaaag tgaaagagat ccgc             234

<210> SEQ ID NO 23
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 23
atcctgccgt tgtgatcgg tgccggtgtt ctgggcgcgt taggcactgg cattggcggg         60
att                                                                      63

<210> SEQ ID NO 24
<211> LENGTH: 123
<212> TYPE: DNA
<213> ORGANISM: Artificial Sequence
<220> FEATURE:
<223> OTHER INFORMATION: Synthetic polynucleotide

<400> SEQUENCE: 24
caggaactga atggggatat ggaacgcgta gcggattcgt tggttacctt acaggaccaa    60
ctgaacagct tagcagcggt tgtgctgcag aatcgtcgtg cccttgatct gctgactgct   120
gaa                                                                 123

<210> SEQ ID NO 25
<211> LENGTH: 102
<212> TYPE: DNA
<213> ORGANISM: Artificial Sequence
<220> FEATURE:
<223> OTHER INFORMATION: Synthetic polynucleotide

<400> SEQUENCE: 25
tatgtcaacc aatccggcat tgtgacggag aaagtgaaag agatccgcga tcgcattcag    60
cgtcgtgcgg aagagctgcg caacaccggt ccgtggggct ta                      102

<210> SEQ ID NO 26
<211> LENGTH: 219
<212> TYPE: DNA
<213> ORGANISM: Artificial Sequence
<220> FEATURE:
<223> OTHER INFORMATION: Synthetic polynucleotide

<400> SEQUENCE: 26
atcctgccgt ttgtgatcgg tgccggtgtt ctgggcgcgt taggcactgg cattggcggg    60
attacgacca gcacccagtt ctactacaag ctgagtcagg aactgaatgg ggatatggaa   120
cgcgtagcgg attcgttggt taccttacag gaccaactga acagcttagc agcggttgtg   180
ctgcagaatc gtcgtgccct tgatctgctg actgctgaa                          219

<210> SEQ ID NO 27
<211> LENGTH: 267
<212> TYPE: DNA
<213> ORGANISM: Artificial Sequence
<220> FEATURE:
<223> OTHER INFORMATION: Synthetic polynucleotide

<400> SEQUENCE: 27
caggaactga atggggatat ggaacgcgta gcggattcgt tggttacctt acaggaccaa    60
ctgaacagct tagcagcggt tgtgctgcag aatcgtcgtg cccttgatct gctgactgct   120
gaacgcggtg gtacctgttt gtttctgggc gaagaatgct gctattatgt caaccaatcc   180
ggcattgtga cggagaaagt gaaagagatc cgcgatcgca ttcagcgtcg tgcggaagag   240
ctgcgcaaca ccggtccgtg gggctta                                       267

<210> SEQ ID NO 28
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 28
atcctgccgt ttgtgatcgg tgccggtgtt ctgggcgcgt taggcactgg cattggcggg    60
attacgacca gcacccagtt ctactacaag ctgagtcagg aactgaatgg ggatatggaa   120
cgcgtagcgg attcgttggt taccttacag gaccaactga acagcttagc agcggttgtg   180
ctgcagaatc gtcgtgccct tgatctgctg actgctgaac gcggtggtac ctgtttgttt   240
ctgggcgaag aatgctgcta ttatgtcaac caatccggca ttgtgacgga gaaagtgaaa   300

-continued

```
gagatccgcg atcgcattca gcgtcgtgcg aagagctgc gcaacaccgg tccgtggggc     360
tta                                                                  363
```

<210> SEQ ID NO 29
<211> LENGTH: 11
<212> TYPE: PRT
<213> ORGANISM: Human immunodeficiency virus type 1

<400> SEQUENCE: 29

Tyr Gly Arg Lys Lys Arg Arg Gln Arg Arg Arg
1               5                   10

<210> SEQ ID NO 30
<211> LENGTH: 23
<212> TYPE: PRT
<213> ORGANISM: Influenza virus

<400> SEQUENCE: 30

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 31
<211> LENGTH: 273
<212> TYPE: PRT
<213> ORGANISM: Artificial Sequence
<220> FEATURE:
<223> OTHER INFORMATION: Synthetic polypeptide

<400> SEQUENCE: 31

Met His His His His His His Asp Tyr Lys Asp Asp Asp Asp Lys Leu
1               5                   10                  15

Val Pro Arg Gly Ser Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser

```
                210                 215                 220
Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser Tyr Gly Arg Lys Lys Arg Arg Gln Arg Arg
                260                 265                 270

Arg

<210> SEQ ID NO 32
<211> LENGTH: 296
<212> TYPE: PRT
<213> ORGANISM: Artificial Sequence
<220> FEATURE:
<223> OTHER INFORMATION: Synthetic polypeptide

<400> SEQUENCE: 32

Met His His His His His Asp Tyr Lys Asp Asp Asp Lys Leu
1               5                   10                  15

Val Pro Arg Gly Ser Met Val Ser Lys Gly Glu Glu Leu Phe Thr Gly
                20                  25                  30

Val Val Pro Ile Leu Val Glu Leu Asp Gly Asp Val Asn Gly His Lys
            35                  40                  45

Phe Ser Val Ser Gly Glu Gly Glu Gly Asp Ala Thr Tyr Gly Lys Leu
50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser Gly Leu Phe Glu Ala Ile Glu Gly Phe Ile
            260                 265                 270

Glu Asn Gly Trp Glu Gly Met Ile Asp Gly Trp Tyr Gly Tyr Gly Arg
        275                 280                 285

Lys Lys Arg Arg Gln Arg Arg Arg
    290                 295
```

<210> SEQ ID NO 33
<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 33

```
Met His His His His His His Asp Tyr Lys Asp Asp Asp Lys Leu
1               5                   10                  15

Val Pro Arg Gly Ser Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser Val Asp Glu Ala Thr Leu Gln Lys Gly Ser
            260                 265                 270

Trp Ser Leu Leu Lys Asp Leu Lys Arg Ile Thr Asp Ser Asp Val Lys
        275                 280                 285

Gly Asp Leu Phe Val Lys Glu Leu Phe Trp Met Leu His Leu Gln Lys
    290                 295                 300

Glu Thr Phe Ala Thr Tyr Val Ala Arg Phe Gln Lys Glu Ala Tyr Tyr
305                 310                 315                 320

Gly Arg Lys Lys Arg Gln Arg Arg
                325                 330
```

<210> SEQ ID NO 34
<211> LENGTH: 355
<212> TYPE: PRT
<213> ORGANISM: Artificial Sequence
<220> FEATURE:
<223> OTHER INFORMATION: Synthetic polypeptide

<400> SEQUENCE: 34

```
Met His His His His His Asp Tyr Lys Asp Asp Asp Asp Lys Leu
1               5                   10                  15

Val Pro Arg Gly Ser Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser His Lys Asp Glu Val Ile Lys Glu Val Gln
            260                 265                 270

Glu Phe Tyr Lys Asp Thr Tyr Asn Lys Leu Lys Thr Lys Asp Glu Pro
        275                 280                 285

Gln Arg Glu Thr Leu Lys Ala Ile His Tyr Ala Leu Asn Cys Cys Gly
    290                 295                 300

Leu Ala Gly Gly Val Glu Gln Phe Ile Ser Ile Cys Pro Lys Lys
305                 310                 315                 320

Asp Val Leu Glu Thr Phe Thr Val Lys Ser Cys Pro Asp Ala Ile Lys
                325                 330                 335

Glu Val Phe Asp Asn Lys Phe His Tyr Gly Arg Lys Lys Arg Arg Gln
            340                 345                 350

Arg Arg Arg
        355
```

<210> SEQ ID NO 35
<211> LENGTH: 309
<212> TYPE: PRT
<213> ORGANISM: Artificial Sequence
<220> FEATURE:
<223> OTHER INFORMATION: Synthetic polypeptide

<400> SEQUENCE: 35

Met His His His His His Asp Tyr Lys Asp Asp Asp Lys Leu
1               5                   10                  15

Val Pro Arg Gly Ser Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser Gly Gly Gly Ser Gly Gly Gly Ser
            260                 265                 270

Gly Gly Gly Gly Ser Ile Leu Pro Phe Val Ile Gly Ala Gly Val Leu
        275                 280                 285

Gly Ala Leu Gly Thr Gly Ile Gly Gly Ile Tyr Gly Arg Lys Lys Arg
    290                 295                 300

Arg Gln Arg Arg Arg
305

<210> SEQ ID NO 36
<211> LENGTH: 314
<212> TYPE: PRT
<213> ORGANISM: Artificial Sequence
<220> FEATURE:
<223> OTHER INFORMATION: Synthetic polypeptide

<400> SEQUENCE: 36

Met His His His His His His Asp Tyr Lys Asp Asp Asp Lys Leu
1               5                   10                  15

Val Pro Arg Gly Ser Met Val Ser Lys Gly Glu Glu Leu Phe Thr Gly

```
            20                  25                  30
Val Val Pro Ile Leu Val Glu Leu Asp Gly Asp Val Asn Gly His Lys
            35                  40                  45
Phe Ser Val Ser Gly Glu Gly Glu Gly Asp Ala Thr Tyr Gly Lys Leu
        50                  55                  60
Thr Leu Lys Phe Ile Cys Thr Thr Gly Lys Leu Pro Val Pro Trp Pro
 65                  70                  75                  80
Thr Leu Val Thr Thr Leu Thr Tyr Gly Val Gln Cys Phe Ser Arg Tyr
                85                  90                  95
Pro Asp His Met Lys Gln His Asp Phe Phe Lys Ser Ala Met Pro Glu
            100                 105                 110
Gly Tyr Val Gln Glu Arg Thr Ile Phe Phe Lys Asp Asp Gly Asn Tyr
            115                 120                 125
Lys Thr Arg Ala Glu Val Lys Phe Glu Gly Asp Thr Leu Val Asn Arg
        130                 135                 140
Ile Glu Leu Lys Gly Ile Asp Phe Lys Glu Asp Gly Asn Ile Leu Gly
145                 150                 155                 160
His Lys Leu Glu Tyr Asn Tyr Asn Ser His Asn Val Tyr Ile Met Ala
                165                 170                 175
Asp Lys Gln Lys Asn Gly Ile Lys Val Asn Phe Lys Ile Arg His Asn
            180                 185                 190
Ile Glu Asp Gly Ser Val Gln Leu Ala Asp His Tyr Gln Gln Asn Thr
            195                 200                 205
Pro Ile Gly Asp Gly Pro Val Leu Leu Pro Asp Asn His Tyr Leu Ser
        210                 215                 220
Thr Gln Ser Ala Leu Ser Lys Asp Pro Asn Glu Lys Arg Asp His Met
225                 230                 235                 240
Val Leu Leu Glu Phe Val Thr Ala Ala Gly Ile Thr Leu Gly Met Asp
                245                 250                 255
Glu Leu Tyr Lys Gly Ser Gln Glu Leu Asn Gly Asp Met Glu Arg Val
            260                 265                 270
Ala Asp Ser Leu Val Thr Leu Gln Asp Gln Leu Asn Ser Leu Ala Ala
            275                 280                 285
Val Val Leu Gln Asn Arg Arg Ala Leu Asp Leu Leu Thr Ala Glu Tyr
        290                 295                 300
Gly Arg Lys Lys Arg Gln Arg Arg
305                 310
```

<210> SEQ ID NO 37
<211> LENGTH: 307
<212> TYPE: PRT
<213> ORGANISM: Artificial Sequence
<220> FEATURE:
<223> OTHER INFORMATION: Synthetic polypeptide

<400> SEQUENCE: 37

```
Met His His His His His Asp Tyr Lys Asp Asp Asp Lys Leu
 1               5                  10                  15
Val Pro Arg Gly Ser Met Val Ser Lys Gly Glu Glu Leu Phe Thr Gly
            20                  25                  30
Val Val Pro Ile Leu Val Glu Leu Asp Gly Asp Val Asn Gly His Lys
            35                  40                  45
Phe Ser Val Ser Gly Glu Gly Glu Gly Asp Ala Thr Tyr Gly Lys Leu
        50                  55                  60
Thr Leu Lys Phe Ile Cys Thr Thr Gly Lys Leu Pro Val Pro Trp Pro
```

```
                65                  70                  75                  80
        Thr Leu Val Thr Thr Leu Thr Tyr Gly Val Gln Cys Phe Ser Arg Tyr
                        85                  90                  95

Pro Asp His Met Lys Gln His Asp Phe Phe Lys Ser Ala Met Pro Glu
                        100                 105                 110

Gly Tyr Val Gln Glu Arg Thr Ile Phe Phe Lys Asp Asp Gly Asn Tyr
                        115                 120                 125

Lys Thr Arg Ala Glu Val Lys Phe Glu Gly Asp Thr Leu Val Asn Arg
                        130                 135                 140

Ile Glu Leu Lys Gly Ile Asp Phe Lys Glu Asp Gly Asn Ile Leu Gly
        145                 150                 155                 160

His Lys Leu Glu Tyr Asn Tyr Asn Ser His Asn Val Tyr Ile Met Ala
                        165                 170                 175

Asp Lys Gln Lys Asn Gly Ile Lys Val Asn Phe Lys Ile Arg His Asn
                        180                 185                 190

Ile Glu Asp Gly Ser Val Gln Leu Ala Asp His Tyr Gln Gln Asn Thr
                        195                 200                 205

Pro Ile Gly Asp Gly Pro Val Leu Leu Pro Asp Asn His Tyr Leu Ser
                        210                 215                 220

Thr Gln Ser Ala Leu Ser Lys Asp Pro Asn Glu Lys Arg Asp His Met
        225                 230                 235                 240

Val Leu Leu Glu Phe Val Thr Ala Ala Gly Ile Thr Leu Gly Met Asp
                        245                 250                 255

Glu Leu Tyr Lys Gly Ser Tyr Val Asn Gln Ser Gly Ile Val Thr Glu
                        260                 265                 270

Lys Val Lys Glu Ile Arg Asp Arg Ile Gln Arg Arg Ala Glu Glu Leu
                        275                 280                 285

Arg Asn Thr Gly Pro Trp Gly Leu Tyr Gly Arg Lys Lys Arg Arg Gln
                        290                 295                 300

Arg Arg Arg
        305

<210> SEQ ID NO 38
<211> LENGTH: 19
<212> TYPE: PRT
<213> ORGANISM: Homo sapiens

<400> SEQUENCE: 38

Val Asp Glu Ala Thr Leu Gln Lys Gly Ser Trp Ser Leu Leu Lys Asp
1               5                   10                  15

Leu Lys Arg

<210> SEQ ID NO 39
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 39

Met His His His His His His Asp Tyr Lys Asp Asp Asp Asp Lys Leu
1               5                   10                  15

Val Pro Arg Gly Ser Met Val Ser Lys Gly Glu Glu Leu Phe Thr Gly
                20                  25                  30

Val Val Pro Ile Leu Val Glu Leu Asp Gly Asp Val Asn Gly His Lys
                35                  40                  45
```

Phe Ser Val Ser Gly Glu Gly Glu Gly Asp Ala Thr Tyr Gly Lys Leu
    50              55                  60

Thr Leu Lys Phe Ile Cys Thr Thr Gly Lys Leu Pro Val Pro Trp Pro
65              70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
                100                 105                 110

Gly Tyr Val Gln Glu Arg Thr Ile Phe Phe Lys Asp Asp Gly Asn Tyr
            115                 120                 125

Lys Thr Arg Ala Glu Val Lys Phe Glu Gly Asp Thr Leu Val Asn Arg
130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
                180                 185                 190

Ile Glu Asp Gly Ser Val Gln Leu Ala Asp His Tyr Gln Gln Asn Thr
            195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser Val Lys Gly Asp Leu Phe Val Lys Glu Leu
                260                 265                 270

Phe Trp Met Leu His Leu Gln Lys Glu Thr Phe Ala Thr Tyr Val Ala
            275                 280                 285

Arg Phe Gln Lys Glu Ala Tyr Tyr Gly Arg Lys Arg Arg Gln Arg
    290                 295                 300

Arg Arg
305

<210> SEQ ID NO 40
<211> LENGTH: 292
<212> TYPE: PRT
<213> ORGANISM: Artificial Sequence
<220> FEATURE:
<223> OTHER INFORMATION: Synthetic polypeptide

<400> SEQUENCE: 40

Met His His His His His Asp Tyr Lys Asp Asp Asp Lys Leu
1               5                   10                  15

Val Pro Arg Gly Ser Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65              70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
                100                 105                 110

Gly Tyr Val Gln Glu Arg Thr Ile Phe Phe Lys Asp Asp Gly Asn Tyr
            115                 120                 125

Lys Thr Arg Ala Glu Val Lys Phe Glu Gly Asp Thr Leu Val Asn Arg
130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser Ile Thr Asp Ser Asp Val Lys Gly Asp Leu
            260                 265                 270

Phe Val Lys Glu Leu Phe Trp Met Leu Tyr Gly Arg Lys Lys Arg Arg
        275                 280                 285

Gln Arg Arg Arg
    290

<210> SEQ ID NO 41
<211> LENGTH: 292
<212> TYPE: PRT
<213> ORGANISM: Artificial Sequence
<220> FEATURE:
<223> OTHER INFORMATION: Synthetic polypeptide

<400> SEQUENCE: 41

Met His His His His His Asp Tyr Lys Asp Asp Asp Lys Leu
1               5                   10                  15

Val Pro Arg Gly Ser Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

```
His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser His Leu Gln Lys Glu Thr Phe Ala Thr Tyr
            260                 265                 270

Val Ala Arg Phe Gln Lys Glu Ala Tyr Tyr Gly Arg Lys Lys Arg Arg
        275                 280                 285

Gln Arg Arg Arg
    290

<210> SEQ ID NO 42
<211> LENGTH: 292
<212> TYPE: PRT
<213> ORGANISM: Artificial Sequence
<220> FEATURE:
<223> OTHER INFORMATION: Synthetic polypeptide

<400> SEQUENCE: 42

Met His His His His His Asp Tyr Lys Asp Asp Asp Lys Leu
1               5                   10                  15

Val Pro Arg Gly Ser Met Val Ser Lys Gly Glu Glu Leu Phe Thr Gly
                20                  25                  30

Val Val Pro Ile Leu Val Glu Leu Asp Gly Asp Val Asn Gly His Lys
            35                  40                  45

Phe Ser Val Ser Gly Glu Gly Glu Gly Asp Ala Thr Tyr Gly Lys Leu
        50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220
```

-continued

```
Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
            245                 250                 255

Glu Leu Tyr Lys Gly Ser Val Asp Glu Ala Thr Leu Gln Lys Gly Ser
        260                 265                 270

Trp Ser Leu Leu Lys Asp Leu Lys Arg Tyr Gly Arg Lys Lys Arg Arg
    275                 280                 285

Gln Arg Arg Arg
    290
```

<210> SEQ ID NO 43
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 43

```
Arg Arg Glu Lys Tyr Gly Ile Pro Glu Pro Pro Glu Pro Lys Arg Arg
1               5                   10                  15

Lys
```

<210> SEQ ID NO 44
<211> LENGTH: 19
<212> TYPE: PRT
<213> ORGANISM: Homo sapiens

<400> SEQUENCE: 44

```
Pro Phe Val Ile Gly Ala Gly Val Leu Gly Ala Leu Gly Thr Gly Ile
1               5                   10                  15

Gly Gly Ile
```

<210> SEQ ID NO 45
<211> LENGTH: 292
<212> TYPE: PRT
<213> ORGANISM: Artificial Sequence
<220> FEATURE:
<223> OTHER INFORMATION: Synthetic polypeptide

<400> SEQUENCE: 45

```
Met His His His His His Asp Tyr Lys Asp Asp Asp Lys Leu
1               5                   10                  15

Val Pro Arg Gly Ser Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125

Lys Thr Arg Ala Glu Val Lys Phe Glu Gly Asp Thr Leu Val Asn Arg
    130                 135                 140
```

```
Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Gly Ser Pro Phe Val Ile Gly Ala Gly Val Leu Gly
                260                 265                 270

Ala Leu Gly Thr Gly Ile Gly Gly Ile Tyr Gly Arg Lys Lys Arg Arg
                275                 280                 285

Gln Arg Arg Arg
    290

<210> SEQ ID NO 46
<211> LENGTH: 235
<212> TYPE: PRT
<213> ORGANISM: Artificial Sequence
<220> FEATURE:
<223> OTHER INFORMATION: Synthetic polypeptide

<400> SEQUENCE: 46

Met His His His His His Asp Tyr Lys Asp Asp Asp Lys Leu
1               5                   10                  15

Val Pro Arg Gly Ser Met Asp Lys Asp Cys Glu Met Lys Arg Thr Thr
                20                  25                  30

Leu Asp Ser Pro Leu Gly Lys Leu Glu Leu Ser Gly Cys Glu Gln Gly
            35                  40                  45

Leu His Glu Ile Ile Phe Leu Gly Lys Gly Thr Ser Ala Ala Asp Ala
        50                  55                  60

Val Glu Val Pro Ala Pro Ala Ala Val Leu Gly Gly Pro Glu Pro Leu
65                  70                  75                  80

Met Gln Ala Thr Ala Trp Leu Asn Ala Tyr Phe His Gln Pro Glu Ala
                85                  90                  95

Ile Glu Glu Phe Pro Val Pro Ala Leu His His Pro Val Phe Gln Gln
            100                 105                 110

Glu Ser Phe Thr Arg Gln Val Leu Trp Lys Leu Leu Lys Val Val Lys
        115                 120                 125

Phe Gly Glu Val Ile Ser Tyr Ser His Leu Ala Ala Leu Ala Gly Asn
    130                 135                 140

Pro Ala Ala Thr Ala Ala Val Lys Thr Ala Leu Ser Gly Asn Pro Val
145                 150                 155                 160

Pro Ile Leu Ile Pro Cys His Arg Val Val Asn Ile Asn Gly Asp Val
                165                 170                 175

Gly Gly Tyr Glu Gly Gly Leu Ala Val Lys Glu Trp Leu Leu Ala His
            180                 185                 190

Glu Gly His Arg Leu Gly Lys Pro Gly Leu Gly Gly Ser Pro Phe Val
        195                 200                 205
```

```
Ile Gly Ala Gly Val Leu Gly Ala Leu Gly Thr Ile Gly Gly Ile
        210                 215                 220

Tyr Gly Arg Lys Lys Arg Gln Arg Arg
225                 230                 235

<210> SEQ ID NO 47
<211> LENGTH: 1078
<212> TYPE: PRT
<213> ORGANISM: Artificial Sequence
<220> FEATURE:
<223> OTHER INFORMATION: Synthetic polypeptide

<400> SEQUENCE: 47

Met His His His His His Asp Tyr Lys Asp Asp Asp Asp Lys Leu
1               5                   10                  15

Val Pro Arg Gly Ser Met Gly Thr Met Ile Thr Asp Ser Leu Ala Val
                20                  25                  30

Val Leu Gln Arg Arg Asp Trp Glu Asn Pro Gly Val Thr Gln Leu Asn
            35                  40                  45

Arg Leu Ala Ala His Pro Pro Phe Ala Ser Trp Arg Asn Ser Glu Glu
        50                  55                  60

Ala Arg Thr Asp Arg Pro Ser Gln Gln Leu Arg Ser Leu Asn Gly Glu
65                  70                  75                  80

Trp Arg Phe Ala Trp Phe Pro Ala Pro Glu Ala Val Pro Glu Ser Trp
                85                  90                  95

Leu Glu Cys Asp Leu Pro Glu Ala Asp Thr Val Val Val Pro Ser Asn
            100                 105                 110

Trp Gln Met His Gly Tyr Asp Ala Pro Ile Tyr Thr Asn Val Thr Tyr
        115                 120                 125

Pro Ile Thr Val Asn Pro Pro Phe Val Pro Thr Glu Asn Pro Thr Gly
    130                 135                 140

Cys Tyr Ser Leu Thr Phe Asn Val Asp Glu Ser Trp Leu Gln Glu Gly
145                 150                 155                 160

Gln Thr Arg Ile Ile Phe Asp Gly Val Asn Ser Ala Phe His Leu Trp
                165                 170                 175

Cys Asn Gly Arg Trp Val Gly Tyr Gly Gln Asp Ser Arg Leu Pro Ser
            180                 185                 190

Glu Phe Asp Leu Ser Ala Phe Leu Arg Ala Gly Glu Asn Arg Leu Ala
        195                 200                 205

Val Met Val Leu Arg Trp Ser Asp Gly Ser Tyr Leu Glu Asp Gln Asp
    210                 215                 220

Met Trp Arg Met Ser Gly Ile Phe Arg Asp Val Ser Leu Leu His Lys
225                 230                 235                 240

Pro Thr Thr Gln Ile Ser Asp Phe His Val Ala Thr Arg Phe Asn Asp
                245                 250                 255

Asp Phe Ser Arg Ala Val Leu Glu Ala Glu Val Gln Met Cys Gly Glu
            260                 265                 270

Leu Arg Asp Tyr Leu Arg Val Thr Val Ser Leu Trp Gln Gly Glu Thr
        275                 280                 285

Gln Val Ala Ser Gly Thr Ala Pro Phe Gly Gly Glu Ile Ile Asp Glu
    290                 295                 300

Arg Gly Gly Tyr Ala Asp Arg Val Thr Leu Arg Leu Asn Val Glu Asn
305                 310                 315                 320

Pro Lys Leu Trp Ser Ala Glu Ile Pro Asn Leu Tyr Arg Ala Val Val
                325                 330                 335
```

-continued

Glu Leu His Thr Ala Asp Gly Thr Leu Ile Glu Ala Glu Ala Cys Asp
            340                 345                 350

Val Gly Phe Arg Glu Val Arg Ile Glu Asn Gly Leu Leu Leu Leu Asn
            355                 360                 365

Gly Lys Pro Leu Leu Ile Arg Gly Val Asn Arg His Glu His His Pro
        370                 375                 380

Leu His Gly Gln Val Met Asp Glu Gln Thr Met Val Gln Asp Ile Leu
385                 390                 395                 400

Leu Met Lys Gln Asn Asn Phe Asn Ala Val Arg Cys Ser His Tyr Pro
                405                 410                 415

Asn His Pro Leu Trp Tyr Thr Leu Cys Asp Arg Tyr Gly Leu Tyr Val
            420                 425                 430

Val Asp Glu Ala Asn Ile Glu Thr His Gly Met Val Pro Met Asn Arg
            435                 440                 445

Leu Thr Asp Asp Pro Arg Trp Leu Pro Ala Met Ser Glu Arg Val Thr
        450                 455                 460

Arg Met Val Gln Arg Asp Arg Asn His Pro Ser Val Ile Ile Trp Ser
465                 470                 475                 480

Leu Gly Asn Glu Ser Gly His Gly Ala Asn His Asp Ala Leu Tyr Arg
                485                 490                 495

Trp Ile Lys Ser Val Asp Pro Ser Arg Pro Val Gln Tyr Glu Gly Gly
            500                 505                 510

Gly Ala Asp Thr Thr Ala Thr Asp Ile Ile Cys Pro Met Tyr Ala Arg
            515                 520                 525

Val Asp Glu Asp Gln Pro Phe Pro Ala Val Pro Lys Trp Ser Ile Lys
            530                 535                 540

Lys Trp Leu Ser Leu Pro Gly Glu Thr Arg Pro Leu Ile Leu Cys Glu
545                 550                 555                 560

Tyr Ala His Ala Met Gly Asn Ser Leu Gly Gly Phe Ala Lys Tyr Trp
                565                 570                 575

Gln Ala Phe Arg Gln Tyr Pro Arg Leu Gln Gly Gly Phe Val Trp Asp
            580                 585                 590

Trp Val Asp Gln Ser Leu Ile Lys Tyr Asp Glu Asn Gly Asn Pro Trp
        595                 600                 605

Ser Ala Tyr Gly Gly Asp Phe Gly Asp Thr Pro Asn Asp Arg Gln Phe
        610                 615                 620

Cys Met Asn Gly Leu Val Phe Ala Asp Arg Thr Pro His Pro Ala Leu
625                 630                 635                 640

Thr Glu Ala Lys His Gln Gln Gln Phe Phe Gln Phe Arg Leu Ser Gly
                645                 650                 655

Gln Thr Ile Glu Val Thr Ser Glu Tyr Leu Phe Arg His Ser Asp Asn
            660                 665                 670

Glu Leu Leu His Trp Met Val Ala Leu Asp Gly Lys Pro Leu Ala Ser
            675                 680                 685

Gly Glu Val Pro Leu Asp Val Ala Pro Gln Gly Lys Gln Leu Ile Glu
        690                 695                 700

Leu Pro Glu Leu Pro Gln Pro Glu Ser Ala Gly Gln Leu Trp Leu Thr
705                 710                 715                 720

Val Arg Val Val Gln Pro Asn Ala Thr Ala Trp Ser Glu Ala Gly His
                725                 730                 735

Ile Ser Ala Trp Gln Gln Trp Arg Leu Ala Glu Asn Leu Ser Val Thr
            740                 745                 750

-continued

```
Leu Pro Ala Ala Ser His Ala Ile Pro His Leu Thr Ser Glu Met
        755                 760                 765

Asp Phe Cys Ile Glu Leu Gly Asn Lys Arg Trp Gln Phe Asn Arg Gln
770                 775                 780

Ser Gly Phe Leu Ser Gln Met Trp Ile Gly Asp Lys Lys Gln Leu Leu
785                 790                 795                 800

Thr Pro Leu Arg Asp Gln Phe Thr Arg Ala Pro Leu Asp Asn Asp Ile
            805                 810                 815

Gly Val Ser Glu Ala Thr Arg Ile Asp Pro Asn Ala Trp Val Glu Arg
        820                 825                 830

Trp Lys Ala Ala Gly His Tyr Gln Ala Glu Ala Ala Leu Leu Gln Cys
835                 840                 845

Thr Ala Asp Thr Leu Ala Asp Ala Val Leu Ile Thr Thr Ala His Ala
    850                 855                 860

Trp Gln His Gln Gly Lys Thr Leu Phe Ile Ser Arg Lys Thr Tyr Arg
865                 870                 875                 880

Ile Asp Gly Ser Gly Gln Met Ala Ile Thr Val Asp Val Glu Val Ala
            885                 890                 895

Ser Asp Thr Pro His Pro Ala Arg Ile Gly Leu Asn Cys Gln Leu Ala
        900                 905                 910

Gln Val Ala Glu Arg Val Asn Trp Leu Gly Leu Gly Pro Gln Glu Asn
    915                 920                 925

Tyr Pro Asp Arg Leu Thr Ala Ala Cys Phe Asp Arg Trp Asp Leu Pro
930                 935                 940

Leu Ser Asp Met Tyr Thr Pro Tyr Val Phe Pro Ser Glu Asn Gly Leu
945                 950                 955                 960

Arg Cys Gly Thr Arg Glu Leu Asn Tyr Gly Pro His Gln Trp Arg Gly
            965                 970                 975

Asp Phe Gln Phe Asn Ile Ser Arg Tyr Ser Gln Gln Gln Leu Met Glu
        980                 985                 990

Thr Ser His Arg His Leu Leu His Ala Glu Glu Gly Thr Trp Leu Asn
    995                 1000                1005

Ile Asp Gly Phe His Met Gly Ile Gly Gly Asp Ser Trp Ser
    1010                1015                1020

Pro Ser Val Ser Ala Glu Phe Gln Leu Ser Ala Gly Arg Tyr His
    1025                1030                1035

Tyr Gln Leu Val Trp Cys Gln Lys Gly Ser Pro Phe Val Ile Gly
    1040                1045                1050

Ala Gly Val Leu Gly Ala Leu Gly Thr Gly Ile Gly Gly Ile Tyr
    1055                1060                1065

Gly Arg Lys Lys Arg Arg Gln Arg Arg Arg
    1070                1075
```

<210> SEQ ID NO 48
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 48

```
Met His His His His His His Asp Tyr Lys Asp Asp Asp Lys Leu
1               5                   10                  15

Val Pro Arg Gly Ser Met Asp Lys Asp Cys Glu Met Lys Arg Thr Thr
                20                  25                  30
```

Leu Asp Ser Pro Leu Gly Lys Leu Glu Leu Ser Gly Cys Glu Gln Gly
    35                  40                  45

Leu His Glu Ile Ile Phe Leu Gly Lys Gly Thr Ser Ala Ala Asp Ala
 50                  55                  60

Val Glu Val Pro Ala Pro Ala Ala Val Leu Gly Gly Pro Glu Pro Leu
65                  70                  75                  80

Met Gln Ala Thr Ala Trp Leu Asn Ala Tyr Phe His Gln Pro Glu Ala
                85                  90                  95

Ile Glu Glu Phe Pro Val Pro Ala Leu His His Pro Val Phe Gln Gln
                100                 105                 110

Glu Ser Phe Thr Arg Gln Val Leu Trp Lys Leu Leu Lys Val Val Lys
            115                 120                 125

Phe Gly Glu Val Ile Ser Tyr Ser His Leu Ala Ala Leu Ala Gly Asn
130                 135                 140

Pro Ala Ala Thr Ala Ala Val Lys Thr Ala Leu Ser Gly Asn Pro Val
145                 150                 155                 160

Pro Ile Leu Ile Pro Cys His Arg Val Val Asn Ile Asn Gly Asp Val
                165                 170                 175

Gly Gly Tyr Glu Gly Gly Leu Ala Val Lys Glu Trp Leu Leu Ala His
            180                 185                 190

Glu Gly His Arg Leu Gly Lys Pro Gly Leu Gly Gly Ser Tyr Gly Arg
        195                 200                 205

Lys Lys Arg Arg Gln Arg Arg
        210                 215

<210> SEQ ID NO 49
<211> LENGTH: 1059
<212> TYPE: PRT
<213> ORGANISM: Artificial Sequence
<220> FEATURE:
<223> OTHER INFORMATION: Synthetic polypeptide

<400> SEQUENCE: 49

Met His His His His His Asp Tyr Lys Asp Asp Asp Lys Leu
1               5                   10                  15

Val Pro Arg Gly Ser Met Gly Thr Met Ile Thr Asp Ser Leu Ala Val
            20                  25                  30

Val Leu Gln Arg Arg Asp Trp Glu Asn Pro Gly Val Thr Gln Leu Asn
        35                  40                  45

Arg Leu Ala Ala His Pro Pro Phe Ala Ser Trp Arg Asn Ser Glu Glu
 50                  55                  60

Ala Arg Thr Asp Arg Pro Ser Gln Gln Leu Arg Ser Leu Asn Gly Glu
65                  70                  75                  80

Trp Arg Phe Ala Trp Phe Pro Ala Pro Glu Ala Val Pro Glu Ser Trp
                85                  90                  95

Leu Glu Cys Asp Leu Pro Glu Ala Asp Thr Val Val Val Pro Ser Asn
                100                 105                 110

Trp Gln Met His Gly Tyr Asp Ala Pro Ile Tyr Thr Asn Val Thr Tyr
            115                 120                 125

Pro Ile Thr Val Asn Pro Pro Phe Val Pro Thr Glu Asn Pro Thr Gly
130                 135                 140

Cys Tyr Ser Leu Thr Phe Asn Val Asp Glu Ser Trp Leu Gln Glu Gly
145                 150                 155                 160

Gln Thr Arg Ile Ile Phe Asp Gly Val Asn Ser Ala Phe His Leu Trp
                165                 170                 175

```
Cys Asn Gly Arg Trp Val Gly Tyr Gly Gln Asp Ser Arg Leu Pro Ser
            180                 185                 190

Glu Phe Asp Leu Ser Ala Phe Leu Arg Ala Gly Glu Asn Arg Leu Ala
        195                 200                 205

Val Met Val Leu Arg Trp Ser Asp Gly Ser Tyr Leu Glu Asp Gln Asp
    210                 215                 220

Met Trp Arg Met Ser Gly Ile Phe Arg Asp Val Ser Leu Leu His Lys
225                 230                 235                 240

Pro Thr Thr Gln Ile Ser Asp Phe His Val Ala Thr Arg Phe Asn Asp
                245                 250                 255

Asp Phe Ser Arg Ala Val Leu Glu Ala Glu Val Gln Met Cys Gly Glu
            260                 265                 270

Leu Arg Asp Tyr Leu Arg Val Thr Val Ser Leu Trp Gln Gly Glu Thr
        275                 280                 285

Gln Val Ala Ser Gly Thr Ala Pro Phe Gly Gly Glu Ile Ile Asp Glu
    290                 295                 300

Arg Gly Gly Tyr Ala Asp Arg Val Thr Leu Arg Leu Asn Val Glu Asn
305                 310                 315                 320

Pro Lys Leu Trp Ser Ala Glu Ile Pro Asn Leu Tyr Arg Ala Val Val
                325                 330                 335

Glu Leu His Thr Ala Asp Gly Thr Leu Ile Glu Ala Glu Ala Cys Asp
            340                 345                 350

Val Gly Phe Arg Glu Val Arg Ile Glu Asn Gly Leu Leu Leu Leu Asn
        355                 360                 365

Gly Lys Pro Leu Leu Ile Arg Gly Val Asn Arg His Glu His His Pro
370                 375                 380

Leu His Gly Gln Val Met Asp Glu Gln Thr Met Val Gln Asp Ile Leu
385                 390                 395                 400

Leu Met Lys Gln Asn Asn Phe Asn Ala Val Arg Cys Ser His Tyr Pro
                405                 410                 415

Asn His Pro Leu Trp Tyr Thr Leu Cys Asp Arg Tyr Gly Leu Tyr Val
            420                 425                 430

Val Asp Glu Ala Asn Ile Glu Thr His Gly Met Val Pro Met Asn Arg
        435                 440                 445

Leu Thr Asp Asp Pro Arg Trp Leu Pro Ala Met Ser Glu Arg Val Thr
    450                 455                 460

Arg Met Val Gln Arg Asp Arg Asn His Pro Ser Val Ile Ile Trp Ser
465                 470                 475                 480

Leu Gly Asn Glu Ser Gly His Gly Ala Asn His Asp Ala Leu Tyr Arg
                485                 490                 495

Trp Ile Lys Ser Val Asp Pro Ser Arg Pro Val Gln Tyr Glu Gly Gly
            500                 505                 510

Gly Ala Asp Thr Thr Ala Thr Asp Ile Ile Cys Pro Met Tyr Ala Arg
        515                 520                 525

Val Asp Glu Asp Gln Pro Phe Pro Ala Val Pro Lys Trp Ser Ile Lys
    530                 535                 540

Lys Trp Leu Ser Leu Pro Gly Glu Thr Arg Pro Leu Ile Leu Cys Glu
545                 550                 555                 560

Tyr Ala His Ala Met Gly Asn Ser Leu Gly Gly Phe Ala Lys Tyr Trp
                565                 570                 575

Gln Ala Phe Arg Gln Tyr Pro Arg Leu Gln Gly Gly Phe Val Trp Asp
            580                 585                 590

Trp Val Asp Gln Ser Leu Ile Lys Tyr Asp Glu Asn Gly Asn Pro Trp
```

-continued

```
             595                 600                 605
Ser Ala Tyr Gly Gly Asp Phe Gly Asp Thr Pro Asn Asp Arg Gln Phe
610                 615                 620

Cys Met Asn Gly Leu Val Phe Ala Asp Arg Thr Pro His Pro Ala Leu
625                 630                 635                 640

Thr Glu Ala Lys His Gln Gln Gln Phe Phe Gln Phe Arg Leu Ser Gly
                645                 650                 655

Gln Thr Ile Glu Val Thr Ser Glu Tyr Leu Phe Arg His Ser Asp Asn
                660                 665                 670

Glu Leu Leu His Trp Met Val Ala Leu Asp Gly Lys Pro Leu Ala Ser
                675                 680                 685

Gly Glu Val Pro Leu Asp Val Ala Pro Gln Gly Lys Gln Leu Ile Glu
690                 695                 700

Leu Pro Glu Leu Pro Gln Pro Glu Ser Ala Gly Gln Leu Trp Leu Thr
705                 710                 715                 720

Val Arg Val Val Gln Pro Asn Ala Thr Ala Trp Ser Glu Ala Gly His
                725                 730                 735

Ile Ser Ala Trp Gln Gln Trp Arg Leu Ala Glu Asn Leu Ser Val Thr
                740                 745                 750

Leu Pro Ala Ala Ser His Ala Ile Pro His Leu Thr Thr Ser Glu Met
                755                 760                 765

Asp Phe Cys Ile Glu Leu Gly Asn Lys Arg Trp Gln Phe Asn Arg Gln
770                 775                 780

Ser Gly Phe Leu Ser Gln Met Trp Ile Gly Asp Lys Lys Gln Leu Leu
785                 790                 795                 800

Thr Pro Leu Arg Asp Gln Phe Thr Arg Ala Pro Leu Asp Asn Asp Ile
                805                 810                 815

Gly Val Ser Glu Ala Thr Arg Ile Asp Pro Asn Ala Trp Val Glu Arg
                820                 825                 830

Trp Lys Ala Ala Gly His Tyr Gln Ala Glu Ala Ala Leu Leu Gln Cys
                835                 840                 845

Thr Ala Asp Thr Leu Ala Asp Ala Val Leu Ile Thr Thr Ala His Ala
                850                 855                 860

Trp Gln His Gln Gly Lys Thr Leu Phe Ile Ser Arg Lys Thr Tyr Arg
865                 870                 875                 880

Ile Asp Gly Ser Gly Gln Met Ala Ile Thr Val Asp Val Glu Val Ala
                885                 890                 895

Ser Asp Thr Pro His Pro Ala Arg Ile Gly Leu Asn Cys Gln Leu Ala
                900                 905                 910

Gln Val Ala Glu Arg Val Asn Trp Leu Gly Leu Gly Pro Gln Glu Asn
                915                 920                 925

Tyr Pro Asp Arg Leu Thr Ala Ala Cys Phe Asp Arg Trp Asp Leu Pro
                930                 935                 940

Leu Ser Asp Met Tyr Thr Pro Tyr Val Phe Pro Ser Glu Asn Gly Leu
945                 950                 955                 960

Arg Cys Gly Thr Arg Glu Leu Asn Tyr Gly Pro His Gln Trp Arg Gly
                965                 970                 975

Asp Phe Gln Phe Asn Ile Ser Arg Tyr Ser Gln Gln Gln Leu Met Glu
                980                 985                 990

Thr Ser His Arg His Leu Leu His Ala Glu Glu Gly Thr Trp Leu Asn
                995                1000                1005

Ile Asp Gly Phe His Met Gly Ile Gly Gly Asp Asp Ser Trp Ser
                1010               1015                1020
```

```
Pro Ser Val Ser Ala Glu Phe Gln Leu Ser Ala Gly Arg Tyr His
    1025                1030                1035

Tyr Gln Leu Val Trp Cys Gln Lys Gly Ser Tyr Gly Arg Lys Lys
    1040                1045                1050

Arg Arg Gln Arg Arg Arg
    1055

<210> SEQ ID NO 50
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 50

Val Asp Glu Ala His His His His His His His His His His His
1               5                   10                  15

His His His His His His Ser Asp Val Lys Gly His His His His
            20                  25                  30

His His His His His His His His His His His His His His His
        35                  40                  45

His His His His His Glu Ala Tyr
    50                  55

<210> SEQ ID NO 51
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 51

Val Asp Glu His His His His His His His His His His His His
1               5                   10                  15

His His His His His His Ser Asp Val Lys Gly His His His His
            20                  25                  30

His His His His His His His His His His His His His His His
        35                  40                  45

His His His His His His Glu Ala Tyr
    50                  55

<210> SEQ ID NO 52
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 52

Val Asp Glu Ala His His His His His His His His His His His
1               5                   10                  15

His His His His His His Ser Asp His His His His His His His
            20                  25                  30

His His His His His His His His His His His His His His His
        35                  40                  45

His His His His His Glu Ala Tyr
    50                  55

<210> SEQ ID NO 53
<211> LENGTH: 57
```

```
<212> TYPE: PRT
<213> ORGANISM: Artificial Sequence
<220> FEATURE:
<223> OTHER INFORMATION: Synthetic Polypeptide

<400> SEQUENCE: 53

Val Asp Glu Ala Asx Asx Gln Lys Asx Asx Asx Ser Asx Asx Lys Asp
1               5                   10                  15

Asx Lys Arg Asx Thr Asp Ser Asp Asx Lys Gly Asp Leu Asx Asx Lys
            20                  25                  30

Glu Asx Asx Asx Asx Asx His Leu Asx Asx Glu Thr Asx Ala Thr Asx
        35                  40                  45

Asx Ala Arg Asx Gln Lys Glu Ala Tyr
    50                  55

<210> SEQ ID NO 54
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 54

Val Asp Glu Ala Thr Leu Gln Lys Gly Asx Trp Ser Asx Leu Lys Asp
1               5                   10                  15

Asx Lys Arg Asx Thr Asp Ser Asp Val Lys Gly Asp Leu Asx Val Lys
            20                  25                  30

Glu Asx Phe Trp Met Asx His Leu Gln Lys Glu Thr Asx Ala Thr Tyr
        35                  40                  45

Asx Ala Arg Phe Gln Lys Glu Ala Tyr
    50                  55

<210> SEQ ID NO 55
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 55

Val Asp Glu Ala Thr Leu Gln Lys Gly Asx Trp Ser Leu Leu Lys Asp
1               5                   10                  15

Leu Lys Arg Ile Thr Asp Ser Asp Val Lys Gly Asp Leu Phe Val Lys
            20                  25                  30

Glu Asx Phe Trp Met Leu His Leu Gln Lys Glu Thr Phe Ala Thr Tyr
        35                  40                  45

Val Ala Arg Phe Gln Lys Glu Ala Tyr
    50                  55

<210> SEQ ID NO 56
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 56

His Lys Asp His His His His His His His His His His His His His
1               5                   10                  15

His His His His Lys Thr Lys Asp Glu His His His His His His
            20                  25                  30
```

His His His His His His His Cys Cys Gly Leu Ala Gly Gly Val Glu
            35                  40                  45

Gln Phe Ile Ser Asp Ile Cys Pro Lys Lys Asp Val Leu Glu Thr Phe
    50                  55                  60

Thr Val Lys Ser Cys His His His His His His His His Asn Lys
65                  70                  75                  80

Phe His

<210> SEQ ID NO 57
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 57

His Lys Asp His His His His His His His His His His His His
1               5                   10                  15

His His His His Lys Thr Lys Asp Glu His His His His His His
            20                  25                  30

His His His His His His Asn Cys Cys Gly Leu Ala Gly Gly Val Glu
            35                  40                  45

Gln Phe Ile Ser Asp Ile Cys Pro Lys Lys Asp Val Leu Glu Thr Phe
    50                  55                  60

Thr Val Lys Ser Cys His His His His His His His His Asn Lys
65                  70                  75                  80

Phe His

<210> SEQ ID NO 58
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 58

His Lys His His His His His His His His His His His His His
1               5                   10                  15

His His His His His Thr Lys Asp Glu Pro His His His His His
            20                  25                  30

His His His His His His Cys Cys Gly Leu Ala Gly Gly Val Glu
            35                  40                  45

Gln Phe Ile Ser Asp Ile Cys Pro Lys Lys Asp Val Leu Glu Thr Phe
    50                  55                  60

Thr Val Lys Ser Cys His His His His His His His Asp Asn Lys
65                  70                  75                  80

Phe His

<210> SEQ ID NO 59
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 59

His Lys Asp Glu Asx Asx Lys Glu Asx Gln Glu Asx Asx Lys Asp Asx
1               5                   10                  15

Asx Asn Lys Asx Lys Thr Lys Asp Glu Pro Asx Arg Asx Asx Asx Lys

```
                20                  25                  30
Asx Asx Asx Tyr Asx Asx Asn Asx Asx Gly Leu Ala Gly Gly Val Glu
            35                  40                  45

Gln Asx Asx Ser Asp Asx Asx Lys Lys Asp Asx Asx Glu Thr Asx
    50                  55                  60

Thr Val Lys Ser Asx Pro Asp Ala Asx Lys Glu Asx Asx Asp Asn Lys
 65                  70                  75                  80

Asx His

<210> SEQ ID NO 60
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 60

His Lys Asp Glu Asx Ile Lys Glu Asx Gln Glu Phe Asx Lys Asp Thr
 1               5                  10                  15

Tyr Asn Lys Leu Lys Thr Lys Asp Glu Pro Gln Arg Glu Asx Asx Lys
            20                  25                  30

Ala Asx His Tyr Asx Asx Asn Asx Cys Gly Leu Ala Gly Gly Val Glu
            35                  40                  45

Gln Phe Ile Ser Asp Ile Cys Pro Lys Lys Asp Val Leu Glu Thr Phe
    50                  55                  60

Thr Val Lys Ser Cys Pro Asp Ala Asx Lys Glu Asx Asx Asp Asn Lys
 65                  70                  75                  80

Phe His

<210> SEQ ID NO 61
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 61

His Lys Asp Glu Val Ile Lys Glu Val Gln Glu Phe Tyr Lys Asx Thr
 1               5                  10                  15

Tyr Asn Lys Leu Lys Thr Lys Asp Glu Pro Gln Arg Glu Thr Asx Lys
            20                  25                  30

Ala Ile His Tyr Ala Leu Asn Cys Cys Gly Leu Ala Gly Gly Val Glu
            35                  40                  45

Gln Phe Ile Ser Asp Ile Cys Pro Lys Lys Asp Val Leu Glu Thr Phe
    50                  55                  60

Thr Val Lys Ser Cys Pro Asp Ala Ile Lys Glu Val Phe Asp Asn Lys
 65                  70                  75                  80

Phe His

<210> SEQ ID NO 62
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 62

Ile Leu His His His His His His His His His His His His Thr
 1               5                  10                  15
```

```
Gly Ile Gly His His His His His His His His His His His
            20                  25                  30

His His His His His His His His His His His His His His
        35                  40                  45

His His His His His His His His His His His His His His
    50                  55                  60

His His Leu Asp Leu Leu Thr Ala Glu Arg Gly Gly Thr Cys Leu Phe
65                  70                  75                  80

Leu Gly Glu Glu Cys Cys Tyr Tyr Val Asn Gln Ser Gly Ile Val Thr
                85                  90                  95

Glu Lys Val Lys Glu Ile Arg Asp Arg Ile Gln Arg Arg Ala Glu Glu
            100                 105                 110

Leu Arg Asn Thr Gly Pro Trp Gly Leu
        115                 120
```

<210> SEQ ID NO 63
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 63

```
Ile His His His His His His His His His His His His His His Thr
1               5                   10                  15

Gly Ile Gly His His His Ser His His His His His His His
            20                  25                  30

His His His His His His His His His His His His His His
        35                  40                  45

His His His His His His His His His His His His His His
    50                  55                  60

His His Leu Asp His His His Glu Arg Gly Gly His His His His
65                  70                  75                  80

His Gly Glu Glu His His His Val Asn Gln Ser Gly Ile His His
                85                  90                  95

His His His His His His His His His His His His His Glu Glu
            100                 105                 110

Leu Arg Asn Thr Gly Pro Trp Gly Leu
        115                 120
```

<210> SEQ ID NO 64
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 64

```
Ile Leu His His His His His His His His His His His Gly Thr
1               5                   10                  15

Gly Ile Gly His His His His His His His His His His His
            20                  25                  30

His His His His His His His His His His His His His His
        35                  40                  45

Leu Gln Asp Gln His His His His His His Leu Gln Asn Arg
    50                  55                  60

Arg Glu Glu Asp Leu Leu Thr Ala Glu Arg Gly Gly Glu Glu Glu Glu
```

Glu Gly Glu Glu Glu Glu Glu Glu Asn Gln Ser Gly Ile His His
                65                  70                  75                  80

His His His His His His His His His His His His His His His
                    85                  90                  95

His His Asn Thr Gly Pro Trp Gly Leu
            100                 105                 110

His His Asn Thr Gly Pro Trp Gly Leu
                            115                 120

<210> SEQ ID NO 65
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 65

Ile Leu Pro Phe Val Ile Gly Ala Gly Val Leu Gly Ala Leu Gly Thr
1               5                   10                  15

Gly Ile Gly Gly Ile Thr Thr Ser Thr Gln Phe Tyr Tyr Lys Leu Ser
                20                  25                  30

Gln Glu Leu Asn Gly Asp Met Glu Arg Val Ala Asp Ser Cys Cys Cys
            35                  40                  45

Cys Cys Cys Cys Cys Cys Cys Cys Cys Val Leu Gln Asn Arg
        50                  55                  60

Arg Ala Leu Asp Leu Leu Thr Ala Glu Arg Gly Gly Thr Cys Leu Phe
65                  70                  75                  80

Leu Gly Glu Glu Cys Cys Tyr Tyr Val Asn Gln Ser Gly Ile Val Thr
                85                  90                  95

Glu Lys Val Lys Glu Ile Arg Asp Arg Ile Gln Arg Arg Ala Glu Glu
                100                 105                 110

Leu Arg Asn Thr Gly Pro Trp Gly Leu
            115                 120

<210> SEQ ID NO 66
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 66

Ile Leu Pro Phe Val Ile Gly Ala Gly Val Leu Gly Ala Leu Gly Thr
1               5                   10                  15

Gly Ile Gly Gly Ile Thr Thr Ser Thr Gln Phe Tyr Tyr Lys Leu Ser
                20                  25                  30

Gln Glu Leu Asn Gly Asp Cys Cys Cys Cys Cys Cys Cys Cys Cys
            35                  40                  45

Cys Cys Cys Cys Cys Cys Cys Cys Cys Val Leu Gln Asn Arg
        50                  55                  60

Arg Ala Leu Asp Leu Leu Thr Ala Glu Arg Gly Gly Thr Cys Leu Phe
65                  70                  75                  80

Leu Gly Glu Glu Cys Cys Tyr Tyr Val Asn Gln Ser Gly Ile Val Thr
                85                  90                  95

Glu Lys Val Lys Glu Ile Arg Asp Arg Ile Gln Arg Arg Ala Glu Glu
                100                 105                 110

Leu Arg Asn Thr Gly Pro Trp Gly Leu
            115                 120

```
<210> SEQ ID NO 67
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 67

Ile Leu Pro Phe Val Ile Gly Ala Gly Val Leu Gly Ala Leu Gly Thr
1               5                   10                  15

Gly Ile Gly Gly Ile Thr Thr Ser Thr Gln Phe Tyr Tyr Lys Leu Cys
            20                  25                  30

Cys Cys Cys Cys Cys Cys Cys Cys Cys Cys Cys Cys Cys Cys Cys Cys
        35                  40                  45

Cys Cys Cys Cys Cys Cys Cys Cys Cys Cys Cys Cys Cys Cys Cys Cys
    50                  55                  60

Cys Cys Cys Cys Cys Cys Cys Cys Cys Arg Gly Gly Thr Cys Leu Phe
65                  70                  75                  80

Leu Gly Glu Glu Cys Cys Tyr Tyr Val Asn Gln Ser Gly Ile Val Thr
                85                  90                  95

Glu Lys Val Lys Glu Ile Arg Asp Arg Ile Gln Arg Arg Ala Glu Glu
            100                 105                 110

Leu Arg Asn Thr Gly Pro Trp Gly Leu
        115                 120

<210> SEQ ID NO 68
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 68

Ile Leu Pro Asx Val Ile Gly Asx Gly Asx Asx Asx Asx Leu Asx Asx
1               5                   10                  15

Gly Asx Asx Asx Asx Asx Asx Asx Asx Gln Asx Asx Tyr Lys Asx Asx
            20                  25                  30

Gln Asx Asx Asn Gly Asx Asx Glu Arg Asx Asx Asp Asx Asx Val Thr
        35                  40                  45

Asx Gln Asp Gln Asx Asn Ser Asx Asx Ala Asx Asx Asx Gln Asx Arg
    50                  55                  60

Asx Asx Asx Asx Asx Asx Asx Asx Glu Arg Gly Asx Asx Asx Asx Asx
65                  70                  75                  80

Asx Gly Glu Glu Asx Asx Asx Asx Asx Asn Gln Ser Gly Ile Asx Thr
                85                  90                  95

Glu Asx Asx Lys Glu Asx Arg Asp Asx Asx Gln Arg Asx Ala Glu Glu
            100                 105                 110

Leu Arg Asn Thr Gly Pro Asx Gly Leu
        115                 120

<210> SEQ ID NO 69
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 69

Ile Leu Pro Phe Val Ile Gly Ala Gly Val Leu Asx Ala Leu Gly Thr
```

```
Gly Ile Gly Gly Asx Thr Thr Ser Thr Gln Phe Asx Tyr Lys Asx Ser
            20                  25                  30

Gln Glu Asx Asn Gly Asp Asx Glu Arg Val Ala Asp Asx Leu Val Thr
            35                  40                  45

Leu Gln Asp Gln Leu Asn Ser Asx Ala Ala Val Asx Asx Gln Asn Arg
        50                  55                  60

Arg Asx Leu Asp Asx Leu Thr Ala Glu Arg Gly Gly Asx Asx Leu Phe
 65                  70                  75                  80

Asx Gly Glu Glu Asx Asx Asx Tyr Asx Asn Gln Ser Gly Ile Val Thr
                85                  90                  95

Glu Lys Asx Lys Glu Asx Arg Asp Arg Asx Gln Arg Arg Ala Glu Glu
            100                 105                 110

Leu Arg Asn Thr Gly Pro Trp Gly Leu
            115                 120

<210> SEQ ID NO 70
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 70

Ile Leu Pro Phe Val Ile Gly Ala Gly Val Leu Gly Ala Leu Gly Thr
 1               5                  10                  15

Gly Ile Gly Gly Ile Thr Thr Ser Thr Gln Phe Tyr Tyr Lys Leu Ser
            20                  25                  30

Gln Glu Leu Asn Gly Asp Met Glu Arg Val Ala Asp Ser Leu Val Thr
            35                  40                  45

Leu Gln Asp Gln Leu Asn Ser Leu Ala Ala Val Val Leu Gln Asn Arg
        50                  55                  60

Arg Ala Leu Asp Leu Leu Thr Ala Glu Arg Gly Gly Thr Cys Leu Phe
 65                  70                  75                  80

Leu Gly Glu Glu Asx Cys Tyr Tyr Val Asn Gln Ser Gly Ile Val Thr
                85                  90                  95

Glu Lys Val Lys Glu Asx Arg Asp Arg Ile Gln Arg Arg Ala Glu Glu
            100                 105                 110

Leu Arg Asn Thr Gly Pro Trp Gly Leu
            115                 120

<210> SEQ ID NO 71
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 71

His His His His His His
 1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 72
```

```
Asp Tyr Lys Asp Asp Asp Lys
1               5
```

<210> SEQ ID NO 73
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 73

```
Leu Val Pro Arg Gly Ser
1               5
```

<210> SEQ ID NO 74
<211> LENGTH: 241
<212> TYPE: PRT
<213> ORGANISM: Artificial Sequence
<220> FEATURE:
<223> OTHER INFORMATION: Synthetic Polypeptide

<400> SEQUENCE: 74

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gly
225                 230                 235                 240

Ser
```

<210> SEQ ID NO 75
<211> LENGTH: 291
<212> TYPE: PRT
<213> ORGANISM: Artificial Sequence
<220> FEATURE:
<223> OTHER INFORMATION: Synthetic Polypeptide

<400> SEQUENCE: 75

```
Met His His His His His Asp Tyr Lys Asp Asp Asp Lys Leu Val
1               5                   10                  15

Pro Arg Gly Ser Met Val Ser Lys Glu Glu Leu Phe Thr Gly Val
            20                  25                  30

Val Pro Ile Leu Val Glu Leu Asp Gly Asp Val Asn Gly His Lys Phe
        35                  40                  45

Ser Val Ser Gly Glu Gly Glu Gly Asp Ala Thr Tyr Gly Lys Leu Thr
50                  55                  60

Leu Lys Phe Ile Cys Thr Thr Gly Lys Leu Pro Val Pro Trp Pro Thr
65                  70                  75                  80

Leu Val Thr Thr Leu Thr Tyr Gly Val Gln Cys Phe Ser Arg Tyr Pro
                85                  90                  95

Asp His Met Lys Gln His Asp Phe Phe Lys Ser Ala Met Pro Glu Gly
            100                 105                 110

Tyr Val Gln Glu Arg Thr Ile Phe Phe Lys Asp Asp Gly Asn Tyr Lys
        115                 120                 125

Thr Arg Ala Glu Val Lys Phe Glu Gly Asp Thr Leu Val Asn Arg Ile
130                 135                 140

Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
                165                 170                 175

Lys Gln Lys Asn Gly Ile Lys Val Asn Phe Lys Ile Arg His Asn Ile
            180                 185                 190

Glu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
210                 215                 220

Gln Ser Ala Leu Ser Lys Asp Pro Asn Glu Lys Arg Asp His Met Val
225                 230                 235                 240

Leu Leu Glu Phe Val Thr Ala Ala Gly Ile Thr Leu Gly Met Asp Glu
                245                 250                 255

Leu Tyr Lys Gly Ser Pro Phe Val Ile Gly Ala Gly Val Leu Gly Ala
            260                 265                 270

Leu Gly Thr Gly Ile Gly Gly Ile Tyr Gly Arg Lys Lys Arg Arg Gln
        275                 280                 285

Arg Arg Arg
290
```

<210> SEQ ID NO 76
<211> LENGTH: 1077
<212> TYPE: PRT
<213> ORGANISM: Artificial Sequence
<220> FEATURE:
<223> OTHER INFORMATION: Synthetic Polypeptide

<400> SEQUENCE: 76

```
Met His His His His His His Asp Tyr Lys Asp Asp Asp Lys Leu
1               5                   10                  15

Val Pro Arg Gly Met Gly Thr Met Ile Thr Asp Ser Leu Ala Val Val
            20                  25                  30

Leu Gln Arg Arg Asp Trp Glu Asn Pro Gly Val Thr Gln Leu Asn Arg
```

```
            35                  40                  45
Leu Ala Ala His Pro Pro Phe Ala Ser Trp Arg Asn Ser Glu Glu Ala
 50                  55                  60

Arg Thr Asp Arg Pro Ser Gln Gln Leu Arg Ser Leu Asn Gly Glu Trp
 65                  70                  75                  80

Arg Phe Ala Trp Phe Pro Ala Pro Glu Ala Val Pro Glu Ser Trp Leu
                 85                  90                  95

Glu Cys Asp Leu Pro Glu Ala Asp Thr Val Val Pro Ser Asn Trp
            100                 105                 110

Gln Met His Gly Tyr Asp Ala Pro Ile Tyr Thr Asn Val Thr Tyr Pro
            115                 120                 125

Ile Thr Val Asn Pro Pro Phe Val Pro Thr Glu Asn Pro Thr Gly Cys
130                 135                 140

Tyr Ser Leu Thr Phe Asn Val Asp Glu Ser Trp Leu Gly Glu Gly Gln
145                 150                 155                 160

Thr Arg Ile Ile Phe Asp Gly Val Asn Ser Ala Phe His Leu Trp Cys
                165                 170                 175

Asn Gly Arg Trp Val Gly Tyr Gly Gln Asp Ser Arg Leu Pro Ser Glu
            180                 185                 190

Phe Asp Leu Ser Ala Phe Leu Arg Ala Gly Glu Asn Arg Leu Ala Val
            195                 200                 205

Met Val Leu Arg Trp Ser Asp Gly Ser Tyr Leu Glu Asp Gln Asp Met
210                 215                 220

Trp Arg Met Ser Gly Ile Phe Arg Asp Val Ser Leu Leu His Lys Pro
225                 230                 235                 240

Thr Thr Gln Ile Ser Asp Phe His Val Ala Thr Arg Phe Asn Asp Asp
                245                 250                 255

Phe Ser Arg Ala Val Leu Glu Ala Glu Val Gln Met Cys Gly Glu Leu
            260                 265                 270

Arg Asp Tyr Leu Arg Val Thr Val Ser Leu Trp Gln Gly Glu Thr Gln
            275                 280                 285

Val Ala Ser Gly Thr Ala Pro Phe Gly Gly Glu Ile Ile Asp Glu Arg
290                 295                 300

Gly Gly Tyr Ala Asp Arg Val Thr Leu Arg Leu Asn Val Glu Asn Pro
305                 310                 315                 320

Lys Leu Trp Ser Ala Glu Ile Pro Asn Leu Tyr Arg Ala Val Val Glu
                325                 330                 335

Leu His Thr Ala Asp Gly Thr Leu Ile Glu Ala Glu Ala Cys Asp Val
            340                 345                 350

Gly Phe Arg Glu Val Arg Ile Glu Asn Gly Leu Leu Leu Leu Asn Gly
            355                 360                 365

Lys Pro Leu Leu Ile Arg Gly Val Asn Arg His Glu His His Pro Leu
370                 375                 380

His Gly Gln Val Met Asp Glu Gln Thr Met Val Gln Asp Ile Leu Leu
385                 390                 395                 400

Met Lys Gln Asn Asn Phe Asn Ala Val Arg Cys Ser His Tyr Pro Asn
                405                 410                 415

His Pro Leu Trp Tyr Thr Leu Cys Asp Arg Tyr Gly Leu Tyr Val Val
            420                 425                 430

Asp Glu Ala Asn Ile Glu Thr His Gly Met Val Pro Met Asn Arg Leu
            435                 440                 445

Thr Asp Asp Pro Arg Trp Leu Pro Ala Met Ser Glu Arg Val Thr Arg
450                 455                 460
```

```
Met Val Gln Arg Asp Arg Asn His Pro Ser Val Ile Ile Trp Ser Leu
465                 470                 475                 480

Gly Asn Glu Ser Gly His Gly Ala Asn His Asp Ala Leu Tyr Arg Trp
            485                 490                 495

Ile Lys Ser Val Asp Pro Ser Arg Pro Val Gln Tyr Glu Gly Gly Gly
        500                 505                 510

Ala Asp Thr Thr Ala Thr Asp Ile Ile Cys Pro Met Tyr Ala Arg Val
        515                 520                 525

Asp Glu Asp Gln Pro Phe Pro Ala Val Pro Lys Trp Ser Ile Lys Lys
        530                 535                 540

Trp Leu Ser Leu Pro Gly Glu Thr Arg Pro Leu Ile Leu Cys Glu Tyr
545                 550                 555                 560

Ala His Ala Met Gly Asn Ser Leu Gly Gly Phe Ala Lys Tyr Trp Gln
            565                 570                 575

Ala Phe Arg Gln Tyr Pro Arg Leu Gln Gly Gly Phe Val Trp Asp Trp
        580                 585                 590

Val Asp Gln Ser Leu Ile Lys Tyr Asp Glu Asn Gly Asn Pro Trp Ser
        595                 600                 605

Ala Tyr Gly Gly Asp Phe Gly Asp Thr Pro Asn Asp Arg Gln Phe Cys
610                 615                 620

Met Asn Gly Leu Val Phe Ala Asp Arg Thr Pro His Pro Ala Leu Thr
625                 630                 635                 640

Glu Ala Lys His Gln Gln Phe Phe Gln Phe Arg Leu Ser Gly Gln
            645                 650                 655

Thr Ile Glu Val Thr Ser Glu Tyr Leu Phe Arg His Ser Asp Asn Glu
            660                 665                 670

Leu Leu His Trp Met Val Ala Leu Asp Gly Lys Pro Leu Ala Ser Gly
        675                 680                 685

Glu Val Pro Leu Asp Val Ala Pro Gln Gly Lys Gln Leu Ile Glu Leu
    690                 695                 700

Pro Glu Leu Pro Gln Pro Glu Ser Ala Gly Gln Leu Trp Leu Thr Val
705                 710                 715                 720

Arg Val Val Gln Pro Asn Ala Thr Ala Trp Ser Glu Ala Gly His Ile
                725                 730                 735

Ser Ala Trp Gln Gln Trp Arg Leu Ala Glu Asn Leu Ser Val Thr Leu
                740                 745                 750

Pro Ala Ala Ser His Ala Ile Pro His Leu Thr Thr Ser Glu Met Asp
            755                 760                 765

Phe Cys Ile Glu Leu Gly Asn Lys Arg Trp Gln Phe Asn Arg Gln Ser
        770                 775                 780

Gly Phe Leu Ser Gln Met Trp Ile Gly Asp Lys Lys Gln Leu Leu Thr
785                 790                 795                 800

Pro Leu Arg Asp Gln Phe Thr Arg Ala Pro Leu Asp Asn Asp Ile Gly
            805                 810                 815

Val Ser Glu Ala Thr Arg Ile Asp Pro Asn Ala Trp Val Glu Arg Trp
            820                 825                 830

Lys Ala Ala Gly His Tyr Gln Ala Glu Ala Leu Leu Gln Cys Thr
            835                 840                 845

Ala Asp Thr Leu Ala Asp Ala Val Leu Ile Thr Thr Ala His Ala Trp
        850                 855                 860

Gln His Gln Gly Lys Thr Leu Phe Ile Ser Arg Lys Thr Tyr Arg Ile
865                 870                 875                 880
```

Asp Gly Ser Gly Gln Met Ala Ile Thr Val Asp Val Glu Val Ala Ser
                885                 890                 895

Asp Thr Pro His Pro Ala Arg Ile Gly Leu Asn Cys Gln Leu Ala Gln
            900                 905                 910

Val Ala Glu Arg Val Asn Trp Leu Gly Leu Gly Pro Gln Glu Asn Tyr
            915                 920                 925

Pro Asp Arg Leu Thr Ala Ala Cys Phe Asp Arg Trp Asp Leu Pro Leu
            930                 935                 940

Ser Asp Met Tyr Thr Pro Tyr Val Phe Pro Ser Glu Asn Gly Leu Arg
945                 950                 955                 960

Cys Gly Thr Arg Glu Leu Asn Tyr Gly Pro His Gln Trp Arg Gly Asp
                965                 970                 975

Phe Gln Phe Asn Ile Ser Arg Tyr Ser Gln Gln Gln Leu Met Glu Thr
                980                 985                 990

Ser His Arg His Leu Leu His Ala Glu Glu Gly Thr Trp Leu Asn Ile
            995                 1000                1005

Asp Gly Phe His Met Gly Ile Gly Gly Asp Asp Ser Trp Ser Pro
    1010                1015                1020

Ser Val Ser Ala Glu Phe Gln Leu Ser Ala Gly Arg Tyr His Tyr
    1025                1030                1035

Gln Leu Val Trp Cys Gln Lys Gly Ser Pro Phe Val Ile Gly Ala
    1040                1045                1050

Gly Val Leu Gly Ala Leu Gly Thr Gly Ile Gly Gly Ile Tyr Gly
    1055                1060                1065

Arg Lys Lys Arg Arg Gln Arg Arg
    1070                1075

<210> SEQ ID NO 77
<211> LENGTH: 1058
<212> TYPE: PRT
<213> ORGANISM: Artificial Sequence
<220> FEATURE:
<223> OTHER INFORMATION: Synthetic Polypeptide

<400> SEQUENCE: 77

Met His His His His His Asp Tyr Lys Asp Asp Asp Lys Leu
1               5                   10                  15

Val Pro Arg Gly Met Gly Thr Met Ile Thr Asp Ser Leu Ala Val Val
            20                  25                  30

Leu Gln Arg Arg Asp Trp Glu Asn Pro Gly Val Thr Gln Leu Asn Arg
        35                  40                  45

Leu Ala Ala His Pro Pro Phe Ala Ser Trp Arg Asn Ser Glu Glu Ala
    50                  55                  60

Arg Thr Asp Arg Pro Ser Gln Gln Leu Arg Ser Leu Asn Gly Glu Trp
65                  70                  75                  80

Arg Phe Ala Trp Phe Pro Ala Pro Glu Ala Val Pro Glu Ser Trp Leu
                85                  90                  95

Glu Cys Asp Leu Pro Glu Ala Asp Thr Val Val Val Pro Ser Asn Trp
            100                 105                 110

Gln Met His Gly Tyr Asp Ala Pro Ile Tyr Thr Asn Val Thr Tyr Pro
        115                 120                 125

Ile Thr Val Asn Pro Pro Phe Val Pro Thr Glu Asn Pro Thr Gly Cys
    130                 135                 140

Tyr Ser Leu Thr Phe Asn Val Asp Glu Ser Trp Leu Gly Glu Gly Gln
145                 150                 155                 160

-continued

Thr Arg Ile Ile Phe Asp Gly Val Asn Ser Ala Phe His Leu Trp Cys
            165                 170                 175

Asn Gly Arg Trp Val Gly Tyr Gly Gln Asp Ser Arg Leu Pro Ser Glu
        180                 185                 190

Phe Asp Leu Ser Ala Phe Leu Arg Ala Gly Glu Asn Arg Leu Ala Val
            195                 200                 205

Met Val Leu Arg Trp Ser Asp Gly Ser Tyr Leu Glu Asp Gln Asp Met
        210                 215                 220

Trp Arg Met Ser Gly Ile Phe Arg Asp Val Ser Leu Leu His Lys Pro
225                 230                 235                 240

Thr Thr Gln Ile Ser Asp Phe His Val Ala Thr Arg Phe Asn Asp Asp
            245                 250                 255

Phe Ser Arg Ala Val Leu Glu Ala Glu Val Gln Met Cys Gly Glu Leu
        260                 265                 270

Arg Asp Tyr Leu Arg Val Thr Val Ser Leu Trp Gln Gly Glu Thr Gln
            275                 280                 285

Val Ala Ser Gly Thr Ala Pro Phe Gly Gly Glu Ile Ile Asp Glu Arg
        290                 295                 300

Gly Gly Tyr Ala Asp Arg Val Thr Leu Arg Leu Asn Val Glu Asn Pro
305                 310                 315                 320

Lys Leu Trp Ser Ala Glu Ile Pro Asn Leu Tyr Arg Ala Val Val Glu
            325                 330                 335

Leu His Thr Ala Asp Gly Thr Leu Ile Glu Ala Glu Ala Cys Asp Val
        340                 345                 350

Gly Phe Arg Glu Val Arg Ile Glu Asn Gly Leu Leu Leu Leu Asn Gly
            355                 360                 365

Lys Pro Leu Leu Ile Arg Gly Val Asn Arg His Glu His His Pro Leu
        370                 375                 380

His Gly Gln Val Met Asp Glu Gln Thr Met Val Gln Asp Ile Leu Leu
385                 390                 395                 400

Met Lys Gln Asn Asn Phe Asn Ala Val Arg Cys Ser His Tyr Pro Asn
            405                 410                 415

His Pro Leu Trp Tyr Thr Leu Cys Asp Arg Tyr Gly Leu Tyr Val Val
        420                 425                 430

Asp Glu Ala Asn Ile Glu Thr His Gly Met Val Pro Met Asn Arg Leu
            435                 440                 445

Thr Asp Asp Pro Arg Trp Leu Pro Ala Met Ser Glu Arg Val Thr Arg
        450                 455                 460

Met Val Gln Arg Asp Arg Asn His Pro Ser Val Ile Ile Trp Ser Leu
465                 470                 475                 480

Gly Asn Glu Ser Gly His Gly Ala Asn His Asp Ala Leu Tyr Arg Trp
            485                 490                 495

Ile Lys Ser Val Asp Pro Ser Arg Pro Val Gln Tyr Glu Gly Gly Gly
        500                 505                 510

Ala Asp Thr Thr Ala Thr Asp Ile Ile Cys Pro Met Tyr Ala Arg Val
            515                 520                 525

Asp Glu Asp Gln Pro Phe Pro Ala Val Pro Lys Trp Ser Ile Lys Lys
        530                 535                 540

Trp Leu Ser Leu Pro Gly Glu Thr Arg Pro Leu Ile Leu Cys Glu Tyr
545                 550                 555                 560

Ala His Ala Met Gly Asn Ser Leu Gly Gly Phe Ala Lys Tyr Trp Gln
            565                 570                 575

Ala Phe Arg Gln Tyr Pro Arg Leu Gln Gly Gly Phe Val Trp Asp Trp

```
            580                 585                 590
Val Asp Gln Ser Leu Ile Lys Tyr Asp Glu Asn Gly Asn Pro Trp Ser
            595                 600                 605

Ala Tyr Gly Gly Asp Phe Gly Asp Thr Pro Asn Asp Arg Gln Phe Cys
            610                 615                 620

Met Asn Gly Leu Val Phe Ala Asp Arg Thr Pro His Pro Ala Leu Thr
625                 630                 635                 640

Glu Ala Lys His Gln Gln Gln Phe Phe Gln Phe Arg Leu Ser Gly Gln
                    645                 650                 655

Thr Ile Glu Val Thr Ser Glu Tyr Leu Phe Arg His Ser Asp Asn Glu
                    660                 665                 670

Leu Leu His Trp Met Val Ala Leu Asp Gly Lys Pro Leu Ala Ser Gly
                    675                 680                 685

Glu Val Pro Leu Asp Val Ala Pro Gln Gly Lys Gln Leu Ile Glu Leu
            690                 695                 700

Pro Glu Leu Pro Gln Pro Glu Ser Ala Gly Gln Leu Trp Leu Thr Val
705                 710                 715                 720

Arg Val Val Gln Pro Asn Ala Thr Ala Trp Ser Glu Ala Gly His Ile
                    725                 730                 735

Ser Ala Trp Gln Gln Trp Arg Leu Ala Glu Asn Leu Ser Val Thr Leu
                    740                 745                 750

Pro Ala Ala Ser His Ala Ile Pro His Leu Thr Thr Ser Glu Met Asp
            755                 760                 765

Phe Cys Ile Glu Leu Gly Asn Lys Arg Trp Gln Phe Asn Arg Gln Ser
770                 775                 780

Gly Phe Leu Ser Gln Met Trp Ile Gly Asp Lys Lys Gln Leu Leu Thr
785                 790                 795                 800

Pro Leu Arg Asp Gln Phe Thr Arg Ala Pro Leu Asp Asn Asp Ile Gly
                    805                 810                 815

Val Ser Glu Ala Thr Arg Ile Asp Pro Asn Ala Trp Val Glu Arg Trp
            820                 825                 830

Lys Ala Ala Gly His Tyr Gln Ala Glu Ala Ala Leu Leu Gln Cys Thr
            835                 840                 845

Ala Asp Thr Leu Ala Asp Ala Val Leu Ile Thr Thr Ala His Ala Trp
            850                 855                 860

Gln His Gln Gly Lys Thr Leu Phe Ile Ser Arg Lys Thr Tyr Arg Ile
865                 870                 875                 880

Asp Gly Ser Gly Gln Met Ala Ile Thr Val Asp Val Glu Val Ala Ser
                    885                 890                 895

Asp Thr Pro His Pro Ala Arg Ile Gly Leu Asn Cys Gln Leu Ala Gln
            900                 905                 910

Val Ala Glu Arg Val Asn Trp Leu Gly Leu Gly Pro Gln Glu Asn Tyr
            915                 920                 925

Pro Asp Arg Leu Thr Ala Ala Cys Phe Asp Arg Trp Asp Leu Pro Leu
            930                 935                 940

Ser Asp Met Tyr Thr Pro Tyr Val Phe Pro Ser Glu Asn Gly Leu Arg
945                 950                 955                 960

Cys Gly Thr Arg Glu Leu Asn Tyr Gly Pro His Gln Trp Arg Gly Asp
                    965                 970                 975

Phe Gln Phe Asn Ile Ser Arg Tyr Ser Gln Gln Gln Leu Met Glu Thr
            980                 985                 990

Ser His Arg His Leu Leu His Ala  Glu Glu Gly Thr Trp  Leu Asn Ile
            995                 1000                1005
```

-continued

```
Asp Gly Phe His Met Gly Ile Gly Gly Asp Asp Ser Trp Ser Pro
    1010            1015            1020

Ser Val Ser Ala Glu Phe Gln Leu Ser Ala Gly Arg Tyr His Tyr
    1025            1030            1035

Gln Leu Val Trp Cys Gln Lys Gly Ser Tyr Gly Arg Lys Lys Arg
    1040            1045            1050

Arg Gln Arg Arg Arg
    1055
```